United States Patent
Matsuoka

(10) Patent No.: US 9,458,491 B2
(45) Date of Patent: Oct. 4, 2016

(54) METHOD AND REAGENT FOR MEASURING MEVALONIC ACID, 3-HYDROXYMETHYLGLUTARYL COENZYME A, AND COENZYME A

(75) Inventor: Takeshi Matsuoka, Tokyo (JP)

(73) Assignee: ASAHI KASEI PHARMA CORPORATION, Tokyo (JP)

(*) Notice: Subject to any disclaimer, the term of this patent is extended or adjusted under 35 U.S.C. 154(b) by 1154 days.

(21) Appl. No.: 13/144,710

(22) PCT Filed: Jan. 19, 2010

(86) PCT No.: PCT/JP2010/050565
§ 371 (c)(1),
(2), (4) Date: Jul. 15, 2011

(87) PCT Pub. No.: WO2010/082665
PCT Pub. Date: Jul. 22, 2010

(65) Prior Publication Data
US 2012/0040387 A1 Feb. 16, 2012

(30) Foreign Application Priority Data
Jan. 19, 2009 (JP) .............................. 2009-009177

(51) Int. Cl.
| | | |
|---|---|---|
| C12Q 1/26 | (2006.01) | |
| C12Q 1/48 | (2006.01) | |
| C12N 9/02 | (2006.01) | |
| C12N 9/04 | (2006.01) | |
| C12N 9/12 | (2006.01) | |
| C07K 1/00 | (2006.01) | |
| C07H 21/02 | (2006.01) | |
| C12Q 1/00 | (2006.01) | |
| C12R 1/01 | (2006.01) | |
| C12R 1/38 | (2006.01) | |
| G01N 33/53 | (2006.01) | |
| C12N 1/20 | (2006.01) | |

(52) U.S. Cl.
CPC .............. C12Q 1/26 (2013.01); C12N 9/001 (2013.01); C12N 9/0006 (2013.01); C12N 9/1205 (2013.01); C12Q 1/008 (2013.01); C12R 1/01 (2013.01); C12R 1/38 (2013.01); G01N 33/5308 (2013.01)

(58) Field of Classification Search
USPC ............ 435/15, 25, 189, 190, 194; 530/350; 536/23.1
See application file for complete search history.

(56) References Cited

U.S. PATENT DOCUMENTS

| | | |
|---|---|---|
| 5,470,956 A | 11/1995 | Hayashi et al. |
| 5,633,143 A | 5/1997 | Ueda et al. |
| 5,780,256 A | 7/1998 | Ueda et al. |
| 5,804,451 A | 9/1998 | Wang et al. |
| 2006/0035345 A1 | 2/2006 | Nakamatsu et al. |
| 2007/0275432 A1* | 11/2007 | Baux et al. ............. 435/25 |

FOREIGN PATENT DOCUMENTS

| | | |
|---|---|---|
| EP | 0 575 610 A1 | 12/1993 |
| EP | 0 608 117 A2 | 7/1994 |
| EP | 0 632 133 A1 | 1/1995 |
| EP | 0 639 646 A1 | 2/1995 |
| EP | 0 801 301 A2 | 10/1997 |
| JP | 1-144976 A | 6/1989 |
| JP | 3-224498 A | 10/1991 |
| JP | 4-158799 A | 6/1992 |
| JP | 4-278099 A | 10/1992 |
| JP | 4-335898 A | 11/1992 |
| JP | 4-349898 A | 12/1992 |
| JP | 7-159400 A | 6/1995 |
| JP | 9-322800 A | 12/1997 |
| JP | 2007-306821 A | 11/2007 |

OTHER PUBLICATIONS

Alberts et al. (Mevinolin: a highly potent competitive inhibitor of hydroxymethylglutaryl-coenzyme A reductase and a cholesterol lowering agent, 1980, PNAS, vol. 77, pp. 3957-3961).*
Naoumova et al. (Plasma mevalonic acid, an index of cholstrerol synthesis in vivo, and responsiveness to HMG-CoA reductase inhibitors in familial hypercholesterolaemia, 1996, Atherosclerosis, vol. 119, pp. 203-213).*
Extended European Search Report issued with respect to counterpart European Application No. 10731334.8, dated Jan. 15, 2013.
M. Hedl et al: "Class II 3-Hydroxy-3-Methylglutaryl Coenzyme A Reductases", Journal of Bacteriology, vol. 186, No. 7, Mar. 17, 2004, pp. 1927-1932, XP055047561.
G. S. Saini: "Validation of the LC-MS/MS method for the quantification of mevalonic acid in human plasma and determination of the matrix effect", The Journal of Lipid Research, vol. 47, No. 10, Jul. 1, 2006, pp. 2340-2345, XP055047616.

(Continued)

*Primary Examiner* — Sharmila G. Landau
*Assistant Examiner* — Shannon Janssen
(74) *Attorney, Agent, or Firm* — Greenblum & Bernstein, P.L.C.

(57) ABSTRACT

The present invention provides a method for measuring the concentration of an analyte in a test solution wherein the analyte is mevalonic acid and/or 3-hydroxymethylglutaryl coenzyme A, comprising the following steps (p) and (q): (p) a step of allowing an enzyme that catalyzes a reaction represented by Reaction Formula 1 and an enzyme that catalyzes a reaction represented by Reaction Formula 2 to act on a test solution containing mevalonic acid and/or 3-hydroxymethylglutaryl coenzyme A in the presence of a hydrogen acceptor X, a hydrogen donor Y, and coenzyme A; and (q) a step of measuring an amount of: a reduced hydrogen acceptor X that is produced; or an oxidized hydrogen donor Y that is produced; or a hydrogen acceptor X that is decreased; or a hydrogen donor Y that is decreased, wherein the hydrogen donor Y and the reduced hydrogen acceptor X are not the same.

21 Claims, 3 Drawing Sheets

(56) References Cited

OTHER PUBLICATIONS

Woollen B H et al: "Determination of mevalonic acid in human urine as mevalonic acid lactone by gas chromatography-mass spectrometry", Journal of Chromatography B: Biomedical Sciences & Applications, Elsevier, Amsterdam, NL, vol. 760, No. 1, Aug. 25, 2001, pp. 179-184, XP004274003.
Lowry O H: "Amplification by enzymatic cycling.", Molecular and Cellular Biochemistry Nov. 20, 1980, vol. 32, No. 3, Nov. 20, 1980, pp. 135-146, XP009165660.
Matsuoka Takeshi et al: "An ultrasensitive enzymatic method for measuring mevalonic acid in serum.", Journal of Lipid Research, Sep. 2012, vol. 53, No. 9, Sep. 2012, pp. 1987-1992, XP009165622.
Parker et al., "Mevalonic Acid in Human Plasma: Relationship of Concentration and Circadian Rhythm to Cholesterol Synthesis Rates in Man ", Proc. Natl. Acad. Sci. USA. vol. 79, No. 9, (1982), pp. 3037-3041.
Popjak et al., "Determination of Mevalonate in Blood Plasma in Man and Rat. Mevalonate "tolerance" Tests in Man", Journal of Lipid Research, vol. 20, No. 6, (1979), pp. 716-728.
Scoppola et al., "Quantitation of Plasma mevalonic acid using gas chromatography-electron capture mass spectrometry ", Journal of Lipid Research, vol. 32, No. 6, (1991), pp. 1057-1060.
Saini et al., "Validation of the LC-MS/MS Method for the Quantification of Mevalonic Acid in Human Plasma and Determination of the Matrix Effect.", Journal of Lipid Research, vol. 47, No. 10, (2006), pp. 2340-2345.
Hiramatsu et al., "Enzyme Immunoassay of Urinary Mevalonic Acid and its Clinical Application", Clinical Chemistry, vol. 44, No. 10, (1998), pp. 2152-2157.
Jemal et al., "Liquid Chromatography/tandem Mass Spectrometry Methods for Quantitation of Mevalonic Acid in Human Plasma and Urine: Method Validation, Demonstration of Using a Surrogate Analyte . . . ", Rapid Communications in Mass Spectrometry (RCM), vol. 17, No. 15, (2003), pp. 1723-1734.
Yamakoshi et al., "Determination of Urinary myo-inositol Concentration by an Improved Enzymatic Cycling Method Using myo-inositol Dehydrogenase from *Flavobacterium* sp.", Clinica Chimica Acta, vol. 328, No. 1-2, (2003), pp. 163-171.
Takahashi et al., "Carnitine Determination by an Enzymatic Cycling Method with Carnitine Dehydrogenase", Clinical Chemistry, vol. 40, No. 5, (1994), pp. 817-821.
Kishi et al., "Highly Sensitive Cholesterol Assay with Enzymatic Cycling Applied to Measurement of Remnant Lipoprotein-Cholesterol in Serum.", Clinical Chemistry, vol. 48, No. 5, (2002), pp. 737-741.
Kishimoto et al., "A Novel Colorimetric Assay for the Determination of lysophosphatidic Acid in Plasma Using an Enzymatic Cycling Method", Clinica Chimica Acta, vol. 333, No. 1, (2003), pp. 59-67.

Verhille et al., "*Pseudomonas gessardii* sp. nov. and *Pseudornonas migulae* sp. nov., Two New Species Isolated from Natural Mineral Waters ", International Journal of Systematic Bacteriology, vol. 49, No. 4, (1999), pp. 1559-1572.
Wen et al., "Phylogenetic Relationships Among Members of the Comamonadaceae, and description of Delftia Acidovorans (den Dooren de Jong 1926 and Tamaoka et al. 1987) gen. nov., comb. nov. ", International Journal of Systematic Bacteriology, vol. 49, No. 2, (1999), pp. 567-576.
Khan et al., "Insolation and Characterization of a New Poly(3-hydroxybutyrate)-degrading, Denitrifying Bacterium from Activated Sludge", FEMS Microbiolgy Letters, vol. 205, No. 2, (2001), pp. 253-257.
Beach et al., "Cloning, Sequencing, and Overexpression of mvaA, Which Encodes Pseudomonas Mevalonii 3-Hydroxy-3-Methylglutaryl Coenzyme A Reductase ", Journal of Bacteriology, vol. 171, No. 6, (1989), Jun. 1989, pp. 2994- 3001.
Friesen et al., "The 3-hydroxy-3-methylglutaryl Coenzyme-A (HMG-CoA) Reductases", Genome Biology, vol. 5, No. 11, Article 248, (2004), pp. 248.1-248.7.
Asakura, "Hydroxymethylglutaryl-CoA reductase 1.1.1.88 ", Enzyme Handbook, (1992), pp. 1-5.
Asakura, "Hydroxymethylglutaryl-CoA Reductase (NADPH) 1.1.1.34", Enzyme Handbook, (1992), pp. 1-5.
Oulmouden et al., "Nucleotide Sequence of the ERG12 Gene of *Saccharomyces cerevisiae* Encoding Mevalonate Kinase", Current Genetics, vol. 19, No. 1, (1991), pp. 9-14.
Anderson et al., "Nucleotide Sequence and Expression in *Esherichia coli* of the 3-Hydroxy-3-Methylglutaryl Coenzyme A Lyase Gene of Pseudomonas mevalonii", Journal of Bacteriology, vol. 171, No. 12, (1989), pp. 6468-6472.
Kim et al., "Dual Coenzyme Specificity of Archaeoglobus Fulgidus HMG-CoA Reductase", Protein Science, vol. 9, No. 6, (2000), pp. 1226-1234.
Stackebrandt et al., "Taxonomic Parameters Revisited: Tarnished Gold Standards", Microbiology Today, vol. 33, (2006), pp. 152-155.
Vesper et al., "Traceability in Laboratory Medicine", Clinical Chemistry, vol. 55, No. 6, (2009), pp. 1067-1075.
Wilson et al., "Determination of the Enantiomeric Purity of Mevalonolactone via NMR Using a Chiral Lanthanide Shift Reagent. ", Journal of Lipid Research, vol. 23, No. 4, (1982), pp. 645-652.
Clayton, "Methods in Enzymology", Steroids and Terpenoids, vol. 15, (1969), 1969, pp. 393-454.
Search report from International Application No. PCT/JP2010/050565, mail date is Mar. 23, 2010.
International Preliminary Report on Patentability for International Application No. PCT/JP2010/050565, mail date is Aug. 25, 2011.

\* cited by examiner

METHOD AND REAGENT FOR MEASURING MEVALONIC ACID, 3-HYDROXYMETHYLGLUTARYL COENZYME A, AND COENZYME A

SEQUENCE LISTING

The instant application contains a Sequence Listing which has been submitted in ASCII format via EFS-Web and is hereby incorporated by reference in its entirety. Said ASCII copy, created on Aug. 16, 2011, is named P40419.txt and is 36,641 bytes in size.

TECHNICAL FIELD

The present invention relates to a method and a reagent for measuring mevalonic acid, 3-hydroxymethylglutaryl coenzyme A, and coenzyme A.

BACKGROUND ART

To keep track of the amount of a cholesterol synthesized in the body is very important for diagnoses of various pathological conditions and the like. In the body, a cholesterol is synthesized by the mevalonate pathway from acetyl coenzyme A via 3-hydroxymethylglutaryl coenzyme A (hereinafter also referred to as HMG-CoA), mevalonic acid (hereinafter also referred to as MVA), and the like. As the conversion of HMG-CoA to MVA catalyzed by hydroxymethylglutaryl coenzyme A reductase is a rate-determining step in this mevalonate pathway, the amount of a cholesterol synthesized in the body can be estimated by measuring the amount of mevalonic acid (Non Patent Literature 1). So far, MVA in a biological sample has been measured by a radioenzyme assay (Non Patent Literature 2), gas chromatography-mass spectrometry (GC-MS) (Non Patent Literature 3), liquid chromatography-mass spectrometry (LC-MS) (Non Patent Literature 4), an assay using antibody (Non Patent Literature 5), and the like. As shown in the above-mentioned documents, however, serum MVA concentrations are very low (63 to 200 nM [Non Patent Literature 1], 20 to 75 nM [Non Patent Literature 2], 18 nM [Non Patent Literature 3], 7.7 to 86.2 nM [Non Patent Literature 6]), and measurement of serum MVA concentrations by a colorimetric assay using an enzyme has not been reported so far. As in the case of MVA, HMG-CoA is also thought to be important as an indicator for the cholesterol metabolism in the body, but measurement of HMG-CoA concentrations by a colorimetric assay using an enzyme has not been reported so far.

Mevalonic acid has two optical isomers, which are expressed as D-mevalonic acid and L-mevalonic acid by the D/L notation and as R-mevalonic acid and S-mevalonic acid by the R/S notation. While D-mevalonic acid (may be expressed as R-mevalonic acid) is metabolized and it can serve as a substrate of mevalonate kinase and hydroxymethylglutaryl coenzyme A reductase in the body, L-mevalonic acid (may be expressed as S-mevalonic acid) is not metabolized in the body.

In the present specification, a term "D,L-mevalonic acid" or "D,L-MVA" represents racemic mevalonic acid, which is a mixture of the D form and the L form. When a term "mevalonic acid" or "MVA" is simply used in the present specification, the term represents D-mevalonic acid or R-mevalonic acid.

Similarly, 3-hydroxymethylglutaryl coenzyme A also has two optical isomers, which are expressed as D-3-hydroxymethylglutaryl coenzyme A and L-3-hydroxymethylglutaryl coenzyme A by the D/L notation and as R-3-hydroxymethylglutaryl coenzyme A and S-3-hydroxymethylglutaryl coenzyme A by the R/S notation. While D-3-hydroxymethylglutaryl coenzyme A (may be expressed as S-3-hydroxymethylglutaryl coenzyme A) is metabolized (can serve as a substrate of hydroxymethylglutaryl coenzyme A reductase) in the body, L-3-hydroxymethylglutaryl coenzyme A (may be expressed as R-3-hydroxymethylglutaryl coenzyme A) is not metabolized in the body.

In the present specification, a term "D,L-3-hydroxymethylglutaryl coenzyme A" or "D,L-HMG-CoA" represents racemic 3-hydroxymethylglutaryl coenzyme A, which is a mixture of the D form and the L form. When a term "3-hydroxymethylglutaryl coenzyme A" or "HMG-CoA" is simply used, the term represents D-3-hydroxymethylglutaryl coenzyme A or S-3-hydroxymethylglutaryl coenzyme A.

Furthermore, coenzyme A (hereinafter also referred to as CoA) is thought to be important as an indicator or the like of lipid metabolism in the body. However, convenient measurement of CoA concentrations by a colorimetric assay using an enzyme has not been reported so far.

An enzyme cycling Method has been reported as a method for measuring the concentration of an analyte with high sensitivity by a colorimetric assay using an enzyme. The enzyme cycling method is a method of amplifying a signal derived from an analyte A by an enzyme cycling reaction involving a hydrogen acceptor X and a hydrogen donor Y (here, the hydrogen donor Y and the reduced hydrogen acceptor X are not the same substance). The outline of the enzyme cycling method is represented by a combination of the following Reaction Formula 3:

[Formula 1]

(Reaction Formula 3)

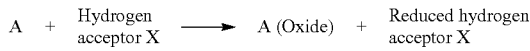

and Reaction Formula 4:

[Formula 2]

(Reaction Formula 4)

Here, A is an analyte, the hydrogen donor Y and the reduced hydrogen acceptor X are not the same substance, and an enzyme that catalyzes Reaction Formulas 3 and 4, a hydrogen acceptor X, and a hydrogen donor Y are added to a test solution containing the analyte A to bring about the above-mentioned enzymatic reactions. The analyte A is cycled between A and A (oxide) during the reaction, and the reduced hydrogen acceptor X and the oxidized hydrogen donor Y are produced depending on the number of cycles. A signal derived from the analyte A is therefore amplified, and the analyte A can be measured with high sensitivity by colorimetrically measuring the amount of the reduced hydrogen acceptor X, the oxidized hydrogen donor Y, the decreased hydrogen acceptor X, or the decreased hydrogen donor Y.

In general, when the amount of an enzyme added to a reaction mixture is increased in an enzyme cycling reaction, the number of enzyme cycling reactions per unit time is increased, thereby improving sensitivity. However, it is impossible to add an enzyme to a reaction mixture in a certain amount or more, or to improve measurement sensitivity due to: 1) the reaction rate constant (kcat) of an enzyme involved in a reaction; 2) the amount of an enzyme that can be dissolved in a reaction mixture; 3) purity of the enzyme used; and the like. Therefore, the enzyme cycling reaction has a lower limit of the measurable concentration of an analyte. When the hydrogen acceptor X is oxidized thio-nicotinamide-adenine-dinucleotide (hereinafter also referred to as T-NAD) or oxidized thio-nicotinamide-adenine-dinucleotide phosphate (hereinafter also referred to as T-NADP), and the hydrogen donor Y is reduced nicotinamide adenine dinucleotide (hereinafter also referred to as NADH) or reduced nicotinamide adenine dinucleotide phosphate (hereinafter also referred to as NADPH) in the above-mentioned enzyme cycling method, the lower limit of the measurable concentration of an analyte is usually approximately 1 to 10 µM (Patent Literatures 1 and 2 and Non Patent Literatures 7 and 8).

Examples of the lower limit of the measurable concentration in a highly sensitive assay using the enzyme cycling method include: 0.2 µM when the analyte A is cholic acid, and the enzyme that catalyzes the enzyme cycling reaction is 3α-steroid dehydrogenase (Patent Literature 3); 0.2 µM when the analyte A is glucose-6-phosphate, and the enzyme that catalyzes the enzyme cycling reaction is glucose-6-phosphate dehydrogenase (Patent Literature 4); and 0.1 µM when the analyte A is a cholesterol and the enzyme that catalyzes the enzyme cycling reaction is cholesterol dehydrogenase (Non Patent Literature 9). Further, when the hydrogen acceptor X is oxygen and the hydrogen donor Y is NADH or reduced NADPH, concentrations to the lower limit of 0.03 µM could be measured by using glycerol-3-phosphate as an analyte, which is obtained by degrading lysophosphatidic acid with lysophosphatidic acid lipase, and using glycerol-3-phosphate oxidase and glycerol-3-phosphate dehydrogenase as enzymes catalyzing a cycling reaction and detecting hydrogen peroxide, which is a reduced hydrogen acceptor X, with peroxidase, 4-aminoantipyrine, and TOOS (Non Patent Literature 10).

In particular, known enzyme cycling reactions in which the hydrogen acceptor X is T-NAD or T-NADP and the hydrogen donor Y is NADH or NADPH are, for example: a reaction represented by a combination of the following Reaction Formula 5:

[Formula 3]

(Reaction Formula 5)

and the following Reaction Formula 6:

[Formula 4]

(Reaction Formula 6)

using a dehydrogenase for the analyte A (Patent Literatures 1, 3, and 4 and Non Patent Literatures 7 and 8); a reaction represented by a combination of the following Reaction Formula 7:

[Formula 5]

(Reaction Formula 7)

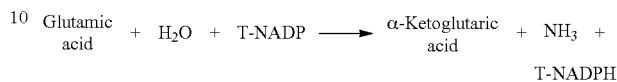

and the following Reaction Formula 8:

[Formula 6]

(Reaction Formula 8)

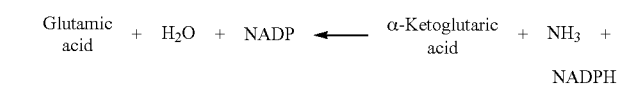

wherein the analyte is glutamic acid, α-ketoglutaric acid, or ammonia, and a glutamate dehydrogenase is used for these analytes (Patent Literature 2); or a reaction represented by a combination of the following Reaction Formula 9:

[Formula 7]

(Reaction Formula 9)

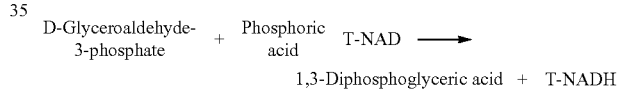

and the following Reaction Formula 10:

[Formula 8]

(Reaction Formula 10)

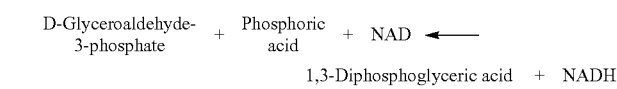

wherein the analyte is D-glyceroaldehyde-3-phosphate, inorganic phosphorus, or 1,3-diphosphoglyceric acid, and a D-glyceroaldehyde-3-phosphate dehydrogenase is used for these analytes (Patent Literature 5), and the like. Furthermore, it has been reported in Patent Literature 2 that the lower limit of the ammonium chloride that can be measured is 40 µM, the lower limit of the L-glutamic acid that can be measured is 40 µM, and the lower limit of L-leucine that can be measured is 4 µM in an enzyme cycling reaction in which leucine dehydrogenase was used instead of glutamate dehydrogenase, and glutamic acid was replaced with leucine and α-ketoglutaric acid was replaced with 2-oxoisocaproate in Reaction Formulas 7 and 8. It has been reported in Patent Literature 4 that the lower limit of the phosphoric acid that can be measured is 10 µM, and that the lower limit was 0.2 µM when measurement was performed using 3-phosphoglycerate kinase after 3-phosphoglyceric acid was converted into 1,3-diphosphoglyceric acid.

CITATION LIST

Patent Literatures

Patent Literature 1: Japanese Patent Laid-Open No. 04-158799
Patent Literature 2: Japanese Patent Laid-Open No. 04-278099
Patent Literature 3: Japanese Patent Laid-Open No. 03-224498
Patent Literature 4: Japanese Patent Laid-Open No. 04-335898
Patent Literature 5: Japanese Patent Laid-Open No. 04-349898
Patent Literature 6: Japanese Patent Laid-Open No. 01-144976

Non Patent Literatures

Non Patent Literature 1: Proc Natl Acad Sci USA. 1982 May; 79(9): 3037-41
Non Patent Literature 2: J Lipid Res. 1979 August; 20(6): 716-28
Non Patent Literature 3: J Lipid Res. 1991 June; 32(6): 1057-60
Non Patent Literature 4: J Lipid Res. 2006 October; 47(10): 2340-5
Non Patent Literature 5: Clin Chem. 1998 October; 44(10): 2152-7
Non Patent Literature 6: Rapid Commun Mass Spectrom. 2003; 17(15): 1723-34
Non Patent Literature 7: Clin Chim Acta. 2003 February; 328 (1-2): 163-71
Non Patent Literature 8: Clin Chem. 1994 May; 40(5): 817-21
Non Patent Literature 9: Clin Chem. 2002 May; 48(5): 737-41
Non Patent Literature 10: Clin Chim Acta. 2003 Jul. 1; 333(1): 59-67

SUMMARY OF INVENTION

Technical Problem

Of conventional techniques to measure MVA in a biological sample as an indicator of the amount of a cholesterol synthesized in the body, for example, a radioenzyme assay uses a radioactive isotope, GC-MS and LC-MS require special devices, and an assay using an antibody uses an antigen-antibody reaction, and therefore, these methods can not treat many specimens or measure substances conveniently with ultrahigh-sensitivity and high precision. As in the case of MVA, for HMG-CoA, which is thought to be important as an indicator of the metabolism of a cholesterol in the body, and for CoA, which is thought to be important as an indicator of lipid metabolism in the body, a method that can treat many specimens conveniently with ultrahigh-sensitivity and high precision was not known so far.

Furthermore, even when an enzyme cycling method is used, the detection limit of an analyte in a test solution is thought to be approximately 0.03 µM from the previous reports. Therefore, when the concentration of an analyte in a test solution is lower than 30 nM, for example, 20, 10, 1, 0.5, or 0.25 nM, the substance could not be measured with high sensitivity or high precision even when an enzyme cycling method was used. In particular, in an enzyme cycling reaction represented by a combination of Reaction Formula 5 and Reaction Formula 6 in which the hydrogen acceptor X is T-NAD or T-NADP and the hydrogen donor Y is NADH or NADPH, when the concentration of an analyte in a test solution is lower than 100 nM, for example, 50, 25, 20, 10, 1, 0.5, or 0.25 nM, the substance could not be measured with high sensitivity and high precision.

Furthermore, as described above, as to an enzyme cycling reaction in which the hydrogen acceptor X is T-NAD or T-NADP, and the hydrogen donor Y is NADH or NADPH, although: a reaction system in which only a hydrogen acceptor X, a hydrogen donor Y, and an analyte A alone are involved; a reaction system in which phosphoric acid is involved in addition to a hydrogen acceptor X, a hydrogen donor Y, and an analyte A; or a reaction system in which water and ammonia are involved in addition to a hydrogen acceptor X, a hydrogen donor Y, and an analyte A has been carried out, an enzyme cycling reaction using a reaction system in which coenzyme A is involved in addition to a hydrogen acceptor X, a hydrogen donor Y, and an analyte A has not been carried out. Furthermore, as shown in combinations of Reaction Formulas 3 and 4, Reaction Formulas 5 and 6, Reaction Formulas 7 and 8, and Reaction Formulas 9 and 10, these reactions are one-step reactions involving hydrogen transfer between a one-molecule substrate and a one-molecule hydrogen acceptor or a one-molecule substrate and a one-molecule hydrogen donor. For example, an enzyme cycling method comprising a three-step reaction including a two reaction steps of a hydrogen transfer between a one-molecule substrate and a two-molecule hydrogen acceptor or a one-molecule substrate and a two-molecule hydrogen donor is unknown so far.

An object of the present invention is to provide a method for measuring MVA and HMG-CoA which are indicators of the amount of a cholesterol synthesized in the body and coenzyme A which is an indicator of lipid metabolism in the body in a biological sample conveniently with ultrahigh-sensitivity and high precision, as well as a measuring reagent used for the measurement.

Solution to Problem

The inventor conducted various researches to achieve the foregoing object. As a result, the inventor found a convenient method for colorimetrically measuring mevalonic acid, 3-hydroxymethylglutaryl coenzyme A, or coenzyme A in a test solution by an enzyme cycling method using hydroxymethylglutaryl coenzyme A reductase with ultrahigh-sensitivity and high precision, and thus accomplished the present invention.

Mevalonic acid dehydrogenase that catalyzes the reaction in which the analyte A is mevalonic acid in the above-mentioned Reaction Formulas 5 and 6 has not been reported so far. Hydroxymethylglutaryl coenzyme A reductase (EC1.1.1.34 and/or EC1.1.1.88: hereinafter also referred to as HMGR. "Enzyme Handbook: Asakura Publishing Co., Ltd. 1982") is known as an enzyme that acts on mevalonic acid. A reaction catalyzed by HMGR is a two-step reaction involving hydrogen transfer between a one-molecule mevalonic acid and a two-molecule hydrogen acceptor or a one-molecule HMG-CoA and a two-molecule hydrogen donor as shown in Reaction Formula 11:

[Formula 9]

(Reaction Formula 11)

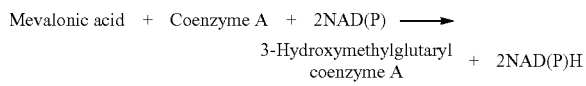

and Reaction Formula 12:

[Formula 10]

(Reaction Formula 12)

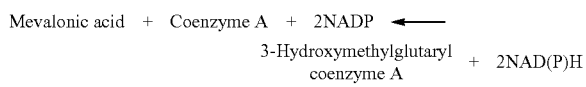

Genome Biol. 2004; 5(11): 248 and Protein Sci. 2000 June; 9(6):12, 26-34 suggest that the above Reaction Formulas 11 and 12 are composed of a three-step reaction including two reaction steps of a hydrogen transfer as shown in the following Reaction Formula 13:

(Reaction Formula 13)

[Formula 11]

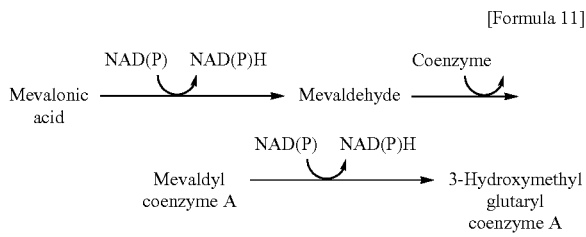

and Reaction Formula 14:

(Reaction Formula 14)

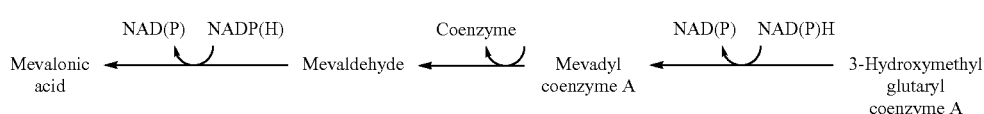

Accordingly, when only the portion of the reaction of mevalonic acid and mevaldehyde in Reaction Formulas 13 and 14, i.e., an enzyme cycling reaction as a one-step reaction involving hydrogen transfer represented by a combination of the following Reaction Formula 15:

(Reaction Formula 15)

[Formula 13]

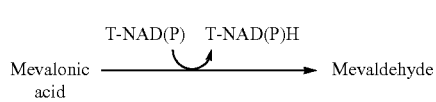

and Reaction Formula 16:

(Reaction Formula 16)

[Formula 14]

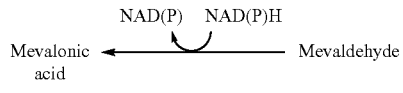

is carried out using HMGR in the absence of coenzyme A, a one-molecule T-NAD(P)H is produced by a one-step reaction. Mevalonic acid may be therefore measured with high sensitivity because the T-NAD(P)H production efficiency is increased as compared with production of a two-molecule T-NAD(P)H by a three-step reaction. Furthermore, when only the portion of the reaction of mevadyl coenzyme A and HMG-CoA in Reaction Formulas 13 and 14, i.e., an enzyme cycling reaction as a one-step reaction involving hydrogen transfer represented by a combination of the following Reaction Formula 17:

(Reaction Formula 17)

[Formula 15]

and Reaction Formula 18:

(Reaction Formula 18)

[Formula 16]

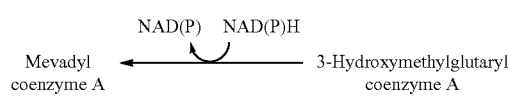

is carried out using HMGR in the absence of coenzyme A, HMG-CoA may be similarly measured with high sensitivity. Contrary to expectations, however, it was found that an enzyme cycling reaction represented by a combination of the above-mentioned Reaction Formulas 15 and 16 does not progress when the concentration of MVA is low, for example, 45 nM or lower in a reaction mixture (90 nM or lower in case of D,L-MVA) or 9 nM or lower (18 nM or lower in case of D,L-MVA), thereby preventing measurement of mevalonic acid with high sensitivity. Furthermore, an enzyme cycling reaction represented by a combination of

[Formula 12]

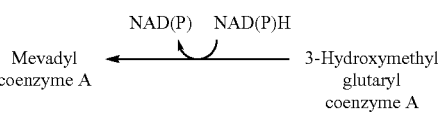

the above-mentioned Reaction Formulas 17 and 18 similarly does not progress when the concentration of HMG-CoA is low, for example, 9 nM or lower in a reaction mixture (18 nM or lower in case of D,L-HMG-CoA), thereby preventing measurement of HMG-CoA with high sensitivity.

On the other hand, because an enzyme cycling reaction comprising a three-step reaction including two reaction steps of a hydrogen transfer represented by a combination of the following Reaction Formula 19:

(Reaction Formula 19)

[Formula 17]

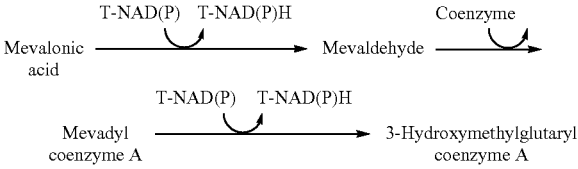

and Reaction Formula 20:

(Reaction Formula 20)

[Formula 18]

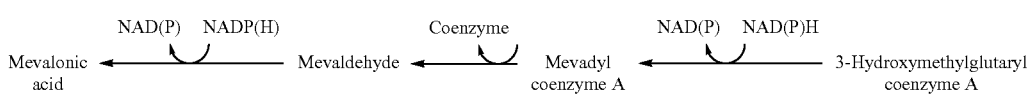

is a multistep reaction, it has been thought that the enzyme cycling reaction does not progress, or the reaction efficiency is very low as compared with the previously reported enzyme cycling reaction comprising a one-step reaction. Surprisingly, the inventor found that this enzyme cycling reaction efficiently progresses, enabling measurement of mevalonic acid or HMG-CoA in the test solution with ultrahigh-sensitivity that has never been achieved.

In other words, the inventor found that: 1) that an enzyme cycling reaction involving coenzyme A that has not been known can be brought about; 2) an enzyme cycling reaction represented by a combination of Reaction Formulas 11 and 12 which comprises a three-step reaction including two reaction steps of a hydrogen transfer can be brought about using enzyme HMGR; and, further, 3) even when the concentration of MVA, HMG-CoA and/or coenzyme A in a test solution is lower than 100 nM, for example, a concentration such as 50, 25, 20, 10, 1, 0.5, or 0.25 nM, MVA, HMG-CoA, and/or coenzyme A can be colorimetrically measured by the above-mentioned enzyme cycling reaction of 2) with ultra high sensitivity that has never been achieved, and thus accomplished the present invention.

Specifically, the present invention relates to the following.

A method for measuring a concentration of an analyte in a test solution wherein the analyte is mevalonic acid and/or 3-hydroxymethylglutaryl coenzyme A, comprising the following steps (p) and (q): (p) a step of allowing an enzyme that catalyzes a reaction represented by Reaction Formula 1:

[Formula 19]

(Reaction Formula 1)

Mevalonic acid + Coenzyme A + 2 Hydrogen acceptor X ⟶ 3-Hydroxymethylglutaryl coenzyme A + 2 Reduced hydrogen acceptor X and an enzyme that catalyzes a reaction represented by Reaction Formula 2:

[Formula 20]

(Reaction Formula 2)

Mevalonic acid + Coenzyme A + 2 Oxidized hydrogen donor Y ⟵ 3-Hydroxymethylglutaryl coenzyme A + 2 Hydrogen donor Y to act on the test solution containing mevalonic acid and/or 3-hydroxymethylglutaryl coenzyme A in the presence of a hydrogen acceptor X, a hydrogen donor Y, and coenzyme A; and (q) a step of measuring an amount of: a reduced hydrogen acceptor X that is produced; or an oxidized hydrogen donor Y that is produced; or a hydrogen acceptor X that is decreased; or a hydrogen donor Y that is decreased, wherein the hydrogen donor Y and the reduced hydrogen acceptor X are not the same.

A method for measuring a concentration of an analyte in a test solution wherein the analyte is coenzyme A, comprising the following steps (p') and (q'): (p') a step of allowing an enzyme that catalyzes a reaction represented by Reaction Formula 1:

[Formula 21]

(Reaction Formula 1)

Mevalonic acid + Coenzyme A + 2 Hydrogen acceptor X ⟶ 3-Hydroxymethylglutaryl coenzyme A + 2 Reduced hydrogen acceptor X and an enzyme that catalyzes a reaction represented by Reaction Formula 2:

(Reaction Formula 2)

Mevalonic acid + Coenzyme A + 2 Oxidized hydrogen donor Y ⟵ 3-Hydroxymethylglutaryl coenzyme A + 2 Hydrogen donor Y to act on the test solution containing coenzyme A in the presence of a hydrogen acceptor X, a hydrogen donor Y, and mevalonic acid; and (q') a step of measuring the amount of: a reduced hydrogen acceptor X that is produced; or an oxidized hydrogen donor Y that is produced; or a hydrogen acceptor X that is decreased; or a hydrogen donor Y that is decreased, wherein the hydrogen donor Y and the reduced hydrogen acceptor X are not the same.

The above-mentioned measuring method, wherein the concentration of the analyte is lower than 30 nM, and the step of measuring the amount of: the reduced hydrogen acceptor X that is produced; or the oxidized hydrogen donor Y that is produced; or the hydrogen acceptor X that is decreased; or the hydrogen donor Y that is decreased is performed by a colorimetric analysis.

The above-mentioned measuring method, wherein the hydrogen acceptor X is selected from a group of oxidized nicotinamide adenine dinucleotides.

The above-mentioned measuring method, wherein the hydrogen donor Y is selected from a group of reduced nicotinamide adenine dinucleotides.

The above-mentioned measuring method, wherein the oxidized nicotinamide adenine dinucleotides are selected from the group consisting of an oxidized nicotinamide adenine dinucleotide, an oxidized nicotinamide adenine dinucleotide phosphate, an oxidized thionicotinamide adenine dinucleotide, an oxidized thionicotinamide adenine dinucleotide phosphate, an oxidized acetyl nicotinamide adenine dinucleotide, and an oxidized acetyl nicotinamide adenine dinucleotide phosphate, and combinations thereof.

The above-mentioned measuring method, wherein the reduced nicotinamide adenine dinucleotides are selected from the group consisting of a reduced nicotinamide adenine dinucleotide, a reduced nicotinamide adenine dinucleotide phosphate, a reduced thionicotinamide adenine dinucleotide, a reduced thionicotinamide adenine dinucleotide phosphate, a reduced acetyl nicotinamide adenine dinucleotide, and a reduced acetyl nicotinamide adenine dinucleotide phosphate, and combinations thereof.

The above-mentioned measuring method, wherein: the concentration of the analyte is lower than 100 nM; the hydrogen acceptor X is an oxidized thionicotinamide adenine dinucleotide or an oxidized thionicotinamide adenine dinucleotide phosphate; the hydrogen donor Y is a reduced nicotinamide adenine dinucleotide or a reduced nicotinamide adenine dinucleotide phosphate; and the step of measuring the amount of: the reduced hydrogen acceptor X that is produced; or the oxidized hydrogen donor Y that is produced; or the hydrogen acceptor X that is decreased; or the hydrogen donor Y that is decreased is performed by a colorimetric analysis.

The above-mentioned measuring method, wherein the enzyme that catalyzes the reaction represented by Reaction Formula 1 is hydroxymethylglutaryl coenzyme A reductase.

The above-mentioned measuring method, wherein the enzyme that catalyzes the reaction represented by Reaction Formula 2 is hydroxymethylglutaryl coenzyme A reductase.

The above-mentioned measuring method, wherein the hydroxymethylglutaryl coenzyme A reductase is derived from the genus of *Pseudomonas*, *Variovorax*, *Delftia*, *Comamonas*, or *Archaeoglobus*.

The above-mentioned measuring method, wherein the enzyme that catalyzes the reaction(s) represented by Reaction Formula 1 and/or Reaction Formula 2 is: (i) a protein having an amino acid sequence represented by any of SEQ ID NOS: 1 to 3; or (ii) a protein having an amino acid sequence which includes deletion, addition, and/or substitution of one or several amino acids in the amino acid sequence represented by any of SEQ ID NOS: 1 to 3 and having an activity of catalyzing the reaction(s) represented by Reaction Formula 1 and/or Reaction Formula 2.

The above-mentioned measuring method, wherein the test solution contains mevalonic acid and 3-hydroxymethylglutaryl coenzyme A, the analyte is 3-hydroxymethylglutaryl coenzyme A, and the method further comprises the following step (o) before the step (p): (o) a step of removing mevalonic acid from the test solution.

The above-mentioned measuring method, wherein the step (o) is performed by an enzymatic reaction, preferably a mevalonate kinase reaction.

The above-mentioned measuring method, characterized in that the step (o) is performed by a mevalonate kinase reaction, and then the step (p) is performed without performing an isolation procedure.

The above-mentioned measuring method, wherein the above-mentioned mevalonate kinase is: (i) a protein having an amino acid sequence encoded by a nucleotide sequence of SEQ ID NO: 5; or (ii) a protein having an amino acid sequence which includes deletion, addition, and/or substitution one or several amino acids in the amino acid sequence encoded by a nucleotide sequence of SEQ ID NO: 5 and having an activity of catalyzing a reaction represented by Reaction Formula 21:

[Formula 23]

(Reaction Formula 21)

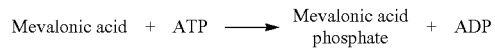

The above-mentioned measuring method, wherein the test solution contains mevalonic acid and 3-hydroxymethylglutaryl coenzyme A, the analyte is mevalonic acid, and the method further comprises the following step (o') before the step (p): (o') a step of removing 3-hydroxymethylglutaryl coenzyme A from the test solution.

The above-mentioned measuring method, wherein the step (o') is performed by an enzymatic reaction.

The above-mentioned measuring method, wherein the enzymatic reaction is a hydroxymethylglutaryl coenzyme A lyase reaction.

The above-mentioned measuring method, wherein the step (o') is performed by a hydroxymethylglutaryl coenzyme A lyase reaction, and then the step (p) is performed without performing the isolation procedure.

The above-mentioned measuring method, wherein the hydroxymethylglutaryl coenzyme A lyase is: (i) a protein having an amino acid sequence of SEQ ID NO: 7; or (ii) a protein having an amino acid sequence which includes deletion, addition, and/or substitution of one or several amino acids in the amino acid sequence of SEQ ID NO: 7 and having an activity of catalyzing a reaction represented by the Reaction Formula 22.

[Formula 24]

(Reaction Formula 22)

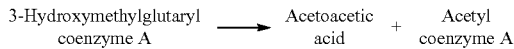

The present invention also relates to the following.

A reagent for measuring mevalonic acid and/or 3-hydroxymethylglutaryl coenzyme A, comprising a hydroxymethylglutaryl coenzyme A reductase, a coenzyme A, an oxidized thionicotinamide adenine dinucleotide (phosphate), and a reduced nicotinamide adenine dinucleotide (phosphate).

The above-mentioned measuring reagent, wherein the mevalonic acid is not substantially contained in the reagent.

A method for producing a reagent for measuring mevalonic acid and/or 3-hydroxymethylglutaryl coenzyme A comprising a hydroxymethylglutaryl coenzyme A reductase, a coenzyme A, an oxidized thionicotinamide adenine dinucleotide (phosphate), and a reduced nicotinamide adenine dinucleotide (phosphate), wherein the method comprises a step of removing contained mevalonic acid using mevalonate kinase.

The above-mentioned measuring reagent, wherein the 3-hydroxymethylglutaryl coenzyme A is not substantially contained in the reagent.

A method for producing a reagent for measuring mevalonic acid and/or 3-hydroxymethylglutaryl coenzyme A comprising a hydroxymethylglutaryl coenzyme A reductase, a coenzyme A, an oxidized thionicotinamide adenine dinucleotide (phosphoric acid), and a reduced nicotinamide adenine dinucleotide (phosphate), wherein the method comprises a step of removing 3-hydroxymethylglutaryl coenzyme A using a 3-hydroxymethylglutaryl coenzyme A lyase.

A reagent for measuring coenzyme A, comprising a hydroxymethylglutaryl coenzyme A reductase, a mevalonic acid, an oxidized thionicotinamide adenine dinucleotide (phosphate), and a reduced nicotinamide adenine dinucleotide (phosphate).

A reagent for measuring 3-hydroxymethylglutaryl coenzyme A, comprising a hydroxymethylglutaryl coenzyme A reductase, a mevalonate kinase, a coenzyme A, a phosphate donor, an oxidized thionicotinamide adenine dinucleotide (phosphate), and a reduced nicotinamide adenine dinucleotide (phosphate).

A reagent for measuring mevalonic acid, comprising a hydroxymethylglutaryl coenzyme A reductase, a hydroxymethylglutaryl coenzyme A lyase, a coenzyme A, an oxidized thionicotinamide adenine dinucleotide (phosphate), and a reduced nicotinamide adenine dinucleotide (phosphate).

A bacterial strain *Pseudomonas* sp. 1-MV (FERM BP-11063) or a mutant thereof which has a 16S rDNA sequence having 97% or higher homology to a sequence of SEQ ID NO: 8 and an ability to produce a protein having an activity of catalyzing the reaction represented by Reaction Formula 1 or 2.

A bacterial strain *Variovorax* sp. 5-MV (FERM BP-11064) or a mutant thereof which has a 16S rDNA sequence having 97% or higher homology to a sequence of SEQ ID NO: 9 and an ability to produce a protein having an activity of catalyzing the reaction represented by Reaction Formula 1 or 2.

A bacterial strain *Delftia* sp. 12-MV (FERM BP-11065) or a mutant thereof which has a 16S rDNA sequence having 97% or higher homology to a sequence of SEQ ID NO: 10 and an ability to produce a protein having an activity of catalyzing the reaction represented by Reaction Formula 1 or 2.

A bacterial strain *Comamonas* sp. 25-MV (FERM BP-11066) or a mutant thereof which has a 16S rDNA sequence having 97% or higher homology to a sequence of SEQ ID NO: 11 and an ability to produce a protein having an activity of catalyzing the reaction represented by Reaction Formula 1 or 2.

A protein according to any of the following (A) to (C): (A) a protein having an amino acid sequence of SEQ ID NO: 1; (B) a protein having an amino acid sequence which has deletion, addition, and/or substitution of one or several amino acids in the amino acid sequence of SEQ ID NO: 1 and an activity of catalyzing a reaction represented by Reaction Formula 1 or 2; and (C) a protein which has an amino acid sequence having 90% or higher homology to an amino acid sequence of SEQ ID NO: 1 and an activity of catalyzing a reaction represented by Reaction Formula 1 or 2.

A standard mevalonic method for accurately measuring an amount of mevalonic acid in a sample, the method comprising at least the following steps (i) to (iv):

(i) a step of allowing a mevalonate kinase to act on the mevalonic acid in the sample in the presence of ATP thereby converting mevalonic acid and ATP to mevalonic acid phosphate and ADP;

(ii) a step of allowing a ADP-dependent hexokinase to act on the ADP produced in the step (i) in the presence of glucose, thereby producing glucose-6-phosphate and AMP;

(iii) a step of allowing a glucose-6-phosphate dehydrogenase to act on the glucose-6-phosphate produced in the step (ii) in the presence of an oxidized nicotinamide adenine dinucleotide (phosphate) thereby producing 6-phosphogluconolactone and a reduced nicotinamide adenine dinucleotide (phosphate); and (iv) a step of measuring the reduced nicotinamide adenine dinucleotide (phosphate) produced in the step (iii) using absorbance.

A standard mevalonic acid measuring method for accurately measuring mevalonic acid in a sample, comprising at least the following steps (i) and (ii):

(i) a step of allowing a hydroxymethylglutaryl coenzyme A reductase to act on the mevalonic acid in the sample in the presence of an oxidized nicotinamide adenine dinucleotide (phosphate) and coenzyme A, thereby producing 3-hydroxymethylglutaryl coenzyme A and a reduced nicotinamide adenine dinucleotide (phosphate); and (ii) a step of measuring the reduced nicotinamide adenine dinucleotide (phosphate) produced in the step (i) using absorbance.

A mevalonic acid reference material with an accurate value of mevalonic acid concentration assigned by the above-mentioned standard measuring method.

Advantageous Effect of Invention

According to the present invention, MVA and/or HMG-CoA in a biological sample which is an indicator of the amount of a cholesterol synthesized in the body or CoA in a biological sample which is an indicator of lipid metabolism in the body can be measured conveniently with ultra-high-sensitivity and high precision. The above-mentioned measurement can be performed for many specimens using a general-purpose automated analyzer. Therefore, many specimens can be measured accurately in routine clinical tests and the like, which is useful for diagnoses of pathological conditions and the like.

DESCRIPTION OF EMBODIMENTS

Figure 1:
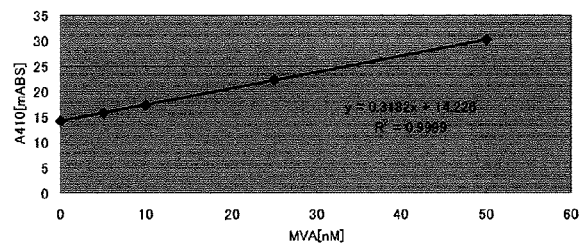
FIG. 1 is a graph showing results of the measurement of MVA using the enzyme cycling reaction in Example 21.

The present invention relates to a method for measuring an analyte in a test solution using an enzyme cycling reaction represented by a combination of Reaction Formula 1:

[Formula 25]

(Reaction Formula 1)

Mevalonic acid + Coenzyme A + 2 Hydrogen acceptor X → 3-Hydroxymethylglutaryl coenzyme A + 2 Reduced hydrogen acceptor X and Reaction Formula 2:

[Formula 26]

(Reaction Formula 2)

Mevalonic acid + Coenzyme A + 2 Oxidized hydrogen donor Y ← 3-Hydroxymethylglutaryl coenzyme A + 2 Hydrogen donor Y In the present specification, the term "test solution" means a solution in which MVA, HMG-CoA and/or coenzyme A, analytes in the measuring method of the present invention, are dissolved. It can be a solution containing water, acids, bases, metal ions, saccharides, alcohols, amino acids, proteins, salts, buffer components, surfactants, chelating agents, and other organic compounds. Examples of test solutions of food include beers, juices, liquid extracts from solid food, and diluted aqueous solutions thereof. Examples of test solutions of biological samples include blood, plasma, serum, intracellular fluids of blood cells and the like, urine, saliva, tear, tissue extracts, and diluted aqueous solutions thereof. Examples also include solutions obtained by adding additives such as acids, bases, metal ions, saccharides, alcohols, amino acids, proteins, salts, buffer components, surfactants, chelating agents, and other organic compounds to above-mentioned test solutions in order to improve stability of an analyte, decrease attachment to a container, improve measurement sensitivity, and the like.

When a test solution is urine, as an indicator of the concentration of the urine, the concentration of a substance in urine, for example, the creatinine concentration, is measured, and the value obtained by dividing the concentration of MVA, HMG-CoA, or CoA in urine by the creatinine concentration can also be used as the indicator.

In the present specification, the term "hydrogen acceptor" means a substance that receives an electron in an oxidation reaction of a substrate by an enzyme in a broad sense. More specifically, it means the substance that receives a hydrogen atom extracted from a substrate. Examples of hydrogen acceptors include oxidized nicotinamide adenine dinucleotides, oxidized quinones, flavins, indophenols, tetrazolium compounds, oxygen molecules, compounds having an SH group, such as cysteine, ferredoxin, cytochrome c3, and cytochrome c6. Examples of oxidized nicotinamide adenine dinucleotides include oxidized nicotinamide adenine dinucleotide (hereinafter also referred to as NAD), oxidized nicotinamide adenine dinucleotide phosphate (hereinafter also referred to as NADP), oxidized thionicotinamide adenine dinucleotide (hereinafter also referred to as T-NAD), oxidized thionicotinamide adenine dinucleotide phosphate (hereinafter also referred to as T-NADP), oxidized acetyl nicotinamide adenine dinucleotide, and oxidized acetyl nicotinamide adenine dinucleotide phosphate. Examples of flavins include FAD, FMN, and riboflavin. Examples of indophenols include 2,6-dichlorophenolindophenol. Examples of tetrazolium compounds include Nitrotetrazolium Blue, WST-1, WST-3, and WST-8.

In the present specification, the term "hydrogen donor" means a substance that gives an electron in a reduction reaction of a substrate by an enzyme in a broad sense. More specifically, it means the substance that provides a hydrogen atom to a substrate. Examples of hydrogen donors include reduced nicotinamide adenine dinucleotides, reduced quinones, reduced riboflavins, and compounds having an S—S bond, such as glutathione. Examples of reduced nicotinamide adenine dinucleotides include reduced nicotinamide adenine dinucleotide (hereinafter also referred to as NADH), reduced nicotinamide adenine dinucleotide phosphate (hereinafter also referred to as NADPH), reduced thionicotinamide adenine dinucleotide (hereinafter also referred to as T-NADH), reduced thionicotinamide adenine dinucleotide phosphate (hereinafter also referred to as T-NADPH), reduced acetyl nicotinamide adenine dinucleotide, and reduced acetyl nicotinamide adenine dinucleotide phosphate.

The hydrogen acceptor in the present specification may also be generally referred to as an electron acceptor, which represents a condition in which an electron of an electron carrier is easily accepted (oxidized). Meanwhile, the hydrogen donor in the present specification may also be commonly referred to as an electron donor, which represents a condition in which an electron of an electron carrier is easily released (reduced). Here, the electron carrier is a generic name of compounds responsible for an electron transfer reaction and may be referred to as a hydrogen carrier.

Examples of the hydrogen acceptor X in the above-mentioned Reaction Formula 1, include oxygen, oxidized quinones, and oxidized nicotinamide adenine dinucleotides.

When the enzyme that catalyzes the reaction represented by Reaction Formula 1 is HMGR, the hydrogen acceptor X is preferably selected from a group of oxidized nicotinamide adenine dinucleotides. Specific examples thereof include NAD, NADP, T-NAD, T-NADP, oxidized acetyl nicotinamide adenine dinucleotide, and oxidized acetyl nicotinamide adenine dinucleotide phosphate.

Examples of the hydrogen donor Y in the above-mentioned Reaction Formula 2 include reduced quinones and reduced nicotinamide adenine dinucleotides. When the enzyme that catalyzes the reaction represented by Reaction Formula 2 is HMGR, the hydrogen donor Y is preferably selected from a group of reduced nicotinamide adenine dinucleotides. Specific examples thereof include NADH, NADPH, T-NADH, T-NADPH, reduced acetyl nicotinamide adenine dinucleotide, and reduced acetyl nicotinamide adenine dinucleotide phosphate.

A combination of T-NAD and NADH, T-NAD and NADPH, T-NADP and NADH, or T-NADP and NADPH is preferably used as a combination of a hydrogen acceptor X and a hydrogen donor Y in a measuring method using an enzyme cycling reaction represented by a combination of Reaction Formulas 1 and 2 catalyzed by an enzyme such as HMGR in which an analyte is MVA and/or HMG-CoA or CoA, since the amount of T-NADH or T-NADPH produced by the enzyme cycling reaction can be measured by absorbance at wavelength of 380 to 430 nm. A suitable combination can be selected depending on the reactivity of an enzyme used, such as HMGR. For example, when HMGR derived from the genus *Pseudomonas, Variovorax, Delftia, Comamonas*, or *Archaeoglobus* is used as the enzyme, a combination of T-NAD and NADH is preferred.

The measuring method of the present invention comprises the step of allowing an enzyme that catalyzes the above-mentioned reactions represented by the Reaction Formulas 1 and 2 to act on the test solution. Such enzymes are not particularly limited so long as the enzymes catalyze the reactions represented by Reaction Formulas 1 and 2 and bring about an enzyme cycling reaction by a combination thereof. Representative examples of such enzymes include a hydroxymethylglutaryl coenzyme A reductase (HMGR).

HMGR is an enzyme that catalyzes the reactions represented by Reaction Formulas 1 and 2, more specifically, the reaction represented by Reaction Formulas 11 and the reaction represented by 12, which is a reverse reaction of the reaction represented by Reaction Formulas 11. Therefore, all previously reported HMGRs, such as HMGRs present in mammals such as humans, mice, and rats, yeasts, archaea, eubacteria, and the like, can be used in the measuring method of the present invention. Furthermore, as with the measuring method in Example 1 described later, the HMGR activity can be determined using Measuring Reagent A. As the presence or absence of HMGR in an extract of a tissue, a cell, or the like can be easily confirmed by this measurement, a novel HMGR can be discovered, and the novel HMGR can be used as the HMGR of the present invention. As novel HMGRs, the inventor discovered HMGRs derived from the genera of *Pseudomonas, Variovorax, Delftia, Comamonas*, and *Archaeoglobus*, more specifically, HMGRs derived from *Pseudomonas* sp. 1-MV (FERM BP-11063), *Variovorax* sp. 5-MV (FERM BP-11064), *Delftia* sp. 12-MV (FERM BP-11065), and *Comamonas* sp. 25-MV (FERM BP-11066).

Specifically, the present invention provides the above-mentioned bacterial strains, *Pseudomonas* sp. 1-MV (FERM BP-11063), *Variovorax* sp. 5-MV (FERM BP-11064), *Delftia* sp. 12-MV (FERM BP-11065), and *Comamonas* sp. 25-MV (FERM BP-11066) and mutants of these bacterial strains whose 16S rDNA sequence has 95% or higher, preferably 97% or higher, more preferably 98% or higher, further preferably 98.5% or higher, particularly preferably 98.7% or higher homology to that of any of these bacterial strains and which have an ability to produce a protein having an activity of catalyzing the reaction of Reaction Formula 1 or 2. It is generally known that bacterial strains having a 16S rDNA sequence of 97% or higher, in particular, 98.7% or higher homology are very likely to belong to the same species (Microbiology Today 2006; 33: 152-155).

Furthermore, as an enzyme that catalyzes the reactions represented by Reaction Formulas 1 and 2, a protein which has an amino acid sequence (if HMGR has a transmembrane domain, preferably an amino acid sequence excluding a sequence for the portion of the transmembrane domain) having 60% or higher, preferably 75% or higher, more preferably 90% or higher homology to that of a known HMGR (for example, HMGR shown in Table 1 of Genome Biol. 2004; 5(11): 248) and catalyzes the reactions represented by Reaction Formulas 1 and 2 can also be used. For example, proteins having an amino acid sequence of any of SEQ ID NOS: 1 to 3 have the HMGR activity and therefore, these proteins can be used. Furthermore, enzymes catalyzing the reactions represented by Reaction Formulas 1 and 2 which have an amino acid sequence including deletion, addition, and/or substitution of one or several (for example, one to nine, more preferably one to five) amino acids in an amino acid sequence obtained by modifying a nucleotide sequence or an amino acid sequence of HMGR, or any of such an amino acid sequence to which another protein or peptide is fused to improve performances such as reactivity, stability, productivity, and purification efficiency can also be used. Enzymes catalyzing the reactions represented by Reaction Formulas 1 and 2 which are obtained by chemically modifying HMGR with PEG or the like or polymerizing HMGR to improve performances such as reactivity and stability can also be used. When a human HMGR inhibitor, such as a statin drug, is contained in a test solution, HMGR that is not inhibited by the inhibitor or is inhibited to a minimal extent (for example, HMGR which is not derived from humans, altered HMGR, modified HMGR, or the like) can be used, or a high concentration of HMGR can be used so that a reaction is not affected by the inhibitor. For example, HMGR derived from *Pseudomonas* sp. 1-MV (FERM BP-11063) can be used because this HMGR is not inhibited by mevastatin or mevinolin.

When HMGR is used as an enzyme that catalyzes the reactions represented by Reaction Formulas 1 and 2, HMGR can be produced according to techniques known to those skilled in the art as described below. For example, yeasts, archaea, eubacteria, and the like that produce HMGR are cultured to accumulate HMGR in the cells or to secrete HMGR into the culture broth, and then the HMGR can be purified according to an enzyme purification method. The yeasts, fungi, archaea, eubacteria, and the like that produce HMGR can be cultured in a medium suitable for increasing the amount of HMGR produced (a medium wherein yeast extracts, nitrogen sources such as ammonium chloride, carbon sources such as glucose, salts, and the like are added in combination, and additives which may increase the production of HMGR, such as mevalonic acid, are added if necessary) under appropriate culture conditions (appropriate pH, temperature, amount of dissolved oxygen, and culture time are set). Genetically-modified organisms that produce HMGR efficiently can be prepared by preparing a fragment in which the HMGR gene is positioned downstream of an appropriate promoter, linking the fragment to an autonomously replicating plasmid, and introducing the plasmid into a bacterium such as *Escherichia coli*, a yeast, a fungus, an insect cell, a mammal cell, and the like or incorporating the fragment into chromosomal DNA of a bacterium such as *Escherichia coli*, a yeast, a fungus, an insect cell, or a mammal cell. The HMGR genes and promoters can be obtained by cloning genomic DNA or cDNA of organisms which have these genes and promoters by employing known methods or chemically synthesizing these genes and promoters based on sequence information. For example, HMGR can be expressed in a recombinant *Escherichia coli* by preparing a fragment in which the HMGR gene is linked downstream of inducible promoters, such as lac promoter, trp promoter, PL promoter, and T7 promoter, or non-inducible promoters, such as pyruvate oxidase promoter (hereinafter also referred to as POP promoter. See SEQ ID NO: 4 and Patent Literature 6), incorporating the fragment into autonomously replicating multicopy plasmids, such as pUC18 and pHSG396, and introducing the plasmids into *Escherichia coli*. To purify the HMGR accumulated in cells, microbial cells are isolated from a culture broth by filtration, centrifugation, or the like, suspended in a buffer with appropriate pH (for example, pH 5.0 to 8.0 for phosphate buffer or pH 7.0 to 10.0 for Tris buffer), with the addition of surfactants, metal salts, saccharides, amino acids, polyols, chelating agents, and the like, if necessary, and disrupted with lysozyme, osmotic pressure, ultrasonication, glass beads, French press, homogenization, or the like, and insoluble matters are then removed by filtration, centrifugation, or the like to obtain a crude HMGR-containing solution. To purify HMGR secreted in a culture broth, microbial cells are removed from a culture broth by filtration, centrifugation, or the like to obtain a crude HMGR-containing solution. Purified HMGR can be obtained by treating the obtained crude HMGR-containing solution with known measures for purifying proteins and enzymes. For example, HMGR can be purified by suitably selecting and using in combination common enzyme purification methods, such as fractional precipitation using organic solvents such as acetone and ethanol, salting out using ammonium sulfate or the like, heat treatment, ion exchange chromatography, hydrophobic chromatography, affinity chromatography, hydroxyapatite chromatography, and gel filtration. A solution obtained by adding salts, surfactants, metal salts, saccharides, amino acids, polyols, chelating agents, coenzymes, and the like to a buffer with appropriate pH can be used as required during the purification process. The purified HMGR can be stored as a solution, a frozen product, a lyophilized product, or the like with the addition of one or more of stabilizers, such as, for example, salts, buffer components, surfactants, metal salts, saccharides, amino acids, polyols, chelating agents, coenzymes, and the like in combination, if necessary.

When an analyte in a test solution is MVA and/or HMG-CoA, in a step of allowing an enzyme that catalyzes the reactions represented by Reaction Formulas 1 and 2 to act, coenzyme A, oxidized nicotinamide adenine dinucleotides, reduced nicotinamide adenine dinucleotides, acids, alkalis, buffer components, salts, surfactants, chelating agents, metal ions, saccharides, amino acids, peptides, proteins, nucleic acids, dyes, alcohols, polyols, organic solvents, preservatives, and the like can be suitably selected and appropriate amounts of these components can be added as components of a reaction mixture used to allow the enzyme to act, so that an enzyme cycling reaction represented by a combination of the reactions represented by Reaction Formulas 1 and 2 should appropriately progress, and that influences of impurities derived from raw materials constituting the test solution or the reaction mixture can be avoided.

More specific examples of substances that can be added to the above-mentioned reaction mixture are listed below, but such substances are not limited to these examples. Examples of oxidized nicotinamide adenine dinucleotides and reduced nicotinamide adenine dinucleotides include the substances already mentioned above. Examples of acids include hydrochloric acid, sulfuric acid, nitric acid, phosphoric acid, citric acid, and acetic acid. Examples of alkalis include sodium hydroxide, potassium hydroxide, ammonia, ethanolamine, and ethylenediamine. Examples of buffer components include acetate buffers, citrate buffers, phosphate buffers, carbonate buffers, borate buffers, ethanolamine buffers, amino acid buffers such as glycine buffer, Tris buffers, and Good's buffers such as HEPES, PIPES, CAPS, and CAPSO. Examples of salts include inorganic and organic sodium salts such as sodium chloride, sodium sulfate, sodium carbonate, sodium bicarbonate, sodium acetate, and sodium nitrate and similar potassium salts, ammonium salts, and lithium salts. Buffer components and salts comprising carbonate ions and hydrogencarbonate ions are preferred to avoid influences of carbon dioxide in the atmosphere when the liquid reagent has high pH (for example, pH 8.5 or higher or pH 9.0 or higher). Examples of surfactants include anionic surfactants such as SDS and SLS, cationic surfactants such as DTAC, ampholytic surfactants such as palmitoyl lysolecithin, CHAPS, and CHAPSO, nonionic surfactants such as Triton and Tween, surfactants having a steroid skeleton such as DOC, surfactants having a sugar skeleton such as n-decyl-β-D-maltoside or n-octyl-β-D-glucoside, and surfactants such as N-acylamino acid salts and alkylether carboxylates. Examples of chelating agents include EDTA, EGTA, IDA, NTPO, and TPEN. Examples of metal ions include ions of metals such as sodium, potassium, lithium, magnesium, calcium, zinc, iron, gold, silver, and copper. Examples of saccharides include monosaccharides and polysaccharides, such as glucose, fructose, xylose, inositol, sorbitol, sucrose, and trehalose. Examples of amino acids include D- and L-amino acids, such as glycine, alanine, ornithine, and norleucine. Examples of peptides include peptides having a length of about two to 10 amino acids, such as, for example, dipeptides, tripeptides, and protein hydrolysate obtained by proteases. Examples of proteins include lysozyme, albumin, sericin, casein, catalase, and peroxidase. Examples of nucleic acids include various deoxyribonucleotides and ribonucleotides. Examples of dyes include chlorophyll, chlorophyllin, tartrazine, methylene blue, methyl red, and phenolphthalein. Examples of alcohols include methanol, ethanol, and octanol. Examples of polyols include ethylene glycol, glycerol, and propylene glycol. Examples of organic solvents include dimethyl sulfoxide, dimethyl formamide, and phenol. Examples of preservatives include antibacterial substances such as sodium azide, Kathon CG, and ProClin, bacteriostatic substances, and antibiotics such as kanamycin.

When an analyte in a test solution is MVA and/or HMG-CoA, in the step of allowing an enzyme that catalyzes a reaction represented by Reaction Formulas 1 and 2 to act, the reaction conditions of the enzyme can be suitably adjusted. For example, 20° C. to 55° C., preferably 25° C. to 45° C., more preferably 30° C. to 40° C. can be used as a reaction temperature, one minute to two hours, preferably three minutes to 35 minutes, more preferably five minutes to 31 minutes can be used as reaction time, and pH 6.0 to 11.0, preferably pH 7.0 to 11.0, more preferably pH 7.5 to 11.0, further preferably pH 8.5 to 10.5 can be used as pH.

Furthermore, the concentration of a buffer component based on a total volume of a reaction mixture can be 5 to 500 mM, preferably 10 to 200 mM, more preferably 20 to 100 mM, for example, when Tris buffer, HEPES buffer, phosphate buffer, carbonate buffer, glycine buffer, CAPS buffer, or CAPSO buffer is used. The concentration of coenzyme A can be 0.001 to 20 mM, preferably 0.01 to 10 mM, more preferably 0.1 to 5 mM.

When an analyte in a test solution is MVA and/or HMG-CoA, and the hydrogen acceptor X is T-NAD(P), the concentration of the hydrogen acceptor X based on the total volume of the reaction mixture is 0.01 to 20 mM, preferably 0.1 to 10 mM, more preferably 0.2 to 4 mM, preferably 0.5 to 8 mM in the step of allowing an enzyme that catalyzes the reactions represented by Reaction Formulas 1 and 2 to act. When a hydrogen donor Y is NAD(P)H, the concentration of the hydrogen donor Y is 0.001 to 5 mM, preferably 0.01 to 2 mM, more preferably 0.02 to 1 mM. When the enzyme that catalyzes the reactions represented by Reaction Formulas 1 and 2 is HMGR, the concentration of the enzyme based on the total volume of the reaction mixture can be adjusted to achieve appropriate sensitivity, and is 1 to 1000 U/mL, preferably 10 to 500 U/mL, more preferably 20 to 200 U/mL, for example. Here, one unit of enzyme activity is defined as the amount of an enzyme required to produce one micromole of NADH per minute at 37° C. in the presence of MVA, CoA and NAD.

Examples of methods for measuring the amount of a reduced hydrogen acceptor X or an oxidized hydrogen donor Y that is produced in the step of allowing the enzyme to act, or the amount of a hydrogen acceptor X or a hydrogen donor Y that is decreased by the step include methods using colorimetric analysis, fluorescence, chemiluminescence, or bioluminescence, methods for measuring a voltage or a current using electrodes, such as voltametry or amperometry, and a method using colorimetric analysis is desirable in view of convenient measurement. For example, when a reduced hydrogen acceptor X is T-NADH or T-NADPH, colorimetric analysis of absorbance at a wavelength of 380 to 430 nm is desirable. In the present specification, the term "colorimetric analysis" is also called absorption spectrometry or absorption photometry and is a method of measuring absorbance by passing a light having a particular wavelength (for example, a light having a wavelength of 340±5 nm) through an analyte solution and determining the concentration of a substance present in the analyte solution from the obtained absorbance according to the Lambert-Beer law.

Even when the concentration of an analyte in a test solution is very low, the concentration can be measured with ultrahigh-sensitivity and high precision in the measuring method of the present invention. For example, when an analyte in a test solution is MVA and/or HMG-CoA, the concentration of MVA and/or HMG-CoA in the test solution is at least the minimum detection limit concentration and 1000 nM or lower, preferably 500 nM or lower, more preferably 250 nM or lower, further preferably 100 nM or lower, and further more preferably 50 nM or lower. Here, the minimum detection limit concentration of MVA and/or HMG-CoA in a test solution is 20 nM or lower, preferably 10 nM or lower, more preferably 5 nM or lower, further preferably 2.5 nM or lower, further more preferably 0.5 nM or lower. The term "minimum detection limit concentration" used herein represents the minimum concentration at which the range of the mean±3 SD obtained by plural measurements of test solutions having several concentration series does not overlap the range of mean±3 SD obtained by measurement of the test solution having a concentration of 0 using the same technique. Here, SD refers to standard deviation.

When an analyte in a test solution is CoA, in the step of allowing an enzyme that catalyzes the reactions represented by Reaction Formulas 1 and 2 to act, the above-mentioned reaction mixture in which the analyte is MVA and/or HMG-CoA can be used as the reaction mixture for enzyme action by replacing CoA with MVA. Here, the concentration of MVA can be 0.0005 to 10 mM, preferably 0.005 to 2.5 mM, more preferably 0.05 to 0.5 mM. Although D,L-MVA can be used, the concentration of the D,L-MVA is about twice the above-mentioned MVA concentration, which is an indicator used in the present invention.

Furthermore, the concentration of an analyte in a test solution can be measured with ultrahigh-sensitivity and high precision in the measuring method of the present invention. When the analyte in the test solution is CoA, the concentration of CoA in the test solution is therefore at least the minimum detection limit concentration and 10 μM or lower, preferably 5000 nM or lower, more preferably 1000 nM or lower, further preferably 500 nM or lower. Here, the minimum detection limit concentration in the test solution is 100 nM or lower, preferably 50 nM or lower. The term "minimum detection limit concentration" used herein represents the minimum concentration at which the range of the mean±3 SD obtained by plural measurements of test solutions having several concentration series does not overlap the range of mean±3 SD obtained by measurement of the test solution having a concentration of 0 using the same technique.

In the measuring method according to the present invention, when an analyte in a test solution is MVA or HMG-CoA, and both MVA and HMG-CoA are present in the test solution, the sum of concentrations of both the substances is obtained by the measurement, but the concentration of either MVA or HMG-CoA alone cannot be obtained. Accordingly, when both MVA and HMG-CoA are present in a test solution, and the concentration of HMG-CoA alone is to be measured, it is desirable that: 1) two samples, i.e., a sample from which HMG-CoA in the test solution is removed and a sample from which HMG-CoA is not removed, are prepared, and an enzyme that catalyzes the reactions represented by Reaction Formulas 1 and 2 is allowed to act on either sample, and the concentration of HMG-CoA in the test solution is calculated from the difference between these measurements; or that 2) the step of removing MVA from the test solution is performed before the step of allowing an enzyme that catalyzes the reactions represented by Reaction Formulas 1 and 2 to act on the test solution. The above 1) can be performed by preparing a sample obtained by removing HMG-CoA from the test solution by the step of removing HMG-CoA from a test solution described later. The step of removing MVA from the test solution for the above 2) is not particularly limited so long as MVA can be removed without removing HMG-CoA, which is the analyte. For example, a method of treating a test solution with an adsorbent specific to MVA or a membrane selective to MVA, a method of converting MVA to a substance that is not involved in the reaction represented by Reaction Formula 1, and the like can be employed. Examples of the method of converting MVA to a substance that is not involved in the reaction represented by Reaction Formula 1 include methods using an enzymatic reaction. For example, as shown in the following Reaction Formula 21:

[Formula 27]

(Reaction Formula 21)

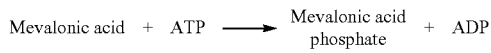

Mevalonic acid + ATP ⟶ Mevalonic acid phosphate + ADP

MVA can be converted to mevalonic acid phosphate, which is not involved in the reaction represented by Reaction Formula 1, using an enzyme in the presence of a phosphate donor such as ATP and a magnesium ion or a manganese ion. Examples of the enzyme include mevalonate kinase (EC2.7.1.36: hereinafter referred to as MVK). In the step of removing MVA by an enzymatic reaction, pH, buffer, salt concentration, and the like of the reaction mixture can be optimized. Furthermore, phosphomevalonate kinase (EC2.7.4.2), which further phosphorylates mevalonic acid phosphate produced by Reaction Formula 21, phosphoenolpyruvate and pyruvate kinase for removing ADP, or glucose and ADP-dependent hexokinase can be added as required.

When the step of removing MVA in a test solution using an enzymatic (for example, MVK) reaction is performed as described above, and the test solution is subjected as it is to an enzyme cycling reaction represented by a combination of Reaction Formulas 1 and 2, the above-mentioned enzyme (for example, MVK) acts on MVA, which is converted from HMG-CoA by Reaction Formula 2. After the step of removing MVA from the test solution using an enzymatic reaction, it is therefore desirable to remove the used enzyme or terminate the reaction of the enzyme. For example, the enzyme can be removed by ultrafiltration using a membrane. When the enzyme is MVK, for example, MVK can be removed without removing HMG-CoA by ultrafiltration using a membrane having a molecular weight cut off of 5000 to 30,000. Furthermore, to terminate the reaction of the enzyme, methods for inactivating a required enzyme without degrading HMG-CoA, such as heat treatment, acid treatment, alkali treatment, and addition of a substance that inactivates the enzyme, methods of adding a substance that inhibits the activity of an intended enzyme (for example, MVK) but does not inhibit the activity of an enzyme that catalyzes the reactions of Reaction Formula 1 and 2 (for example, HMGR) to the reaction mixture, and the like can be employed. Examples of a substance that inhibits a reaction of MVK but does not inhibit an enzyme cycling reaction of HMGR include chelating agents that forms a chelate with a magnesium ion (for example, EDTA, EGTA, and NTA). Of the above-mentioned methods of removing an enzyme or methods of terminating the reaction of the enzyme, the methods using alkali treatment and the methods of adding a chelating agent are preferred because an isolation procedure is not required, and a series of procedures can be performed in the same reaction vessel using an automated analyzer. The term "isolation procedure" used herein refers to a column chromatography procedure, a membrane filtration procedure, an adsorption isolation procedure, an extraction isolation procedure, a precipitation isolation procedure, and the like that are performed during a series of steps of measuring HMG-CoA in a test solution.

The enzyme that can be used in the step of removing MVA is not limited so long as the enzyme can convert MVA to a substance that is not involved in the reaction represented by Reaction Formula 1. For example, an enzyme that catalyzes the reaction represented by Reaction Formula 21 can be used. Specific examples of such enzymes include MVKs derived from mammals such as humans, mice, and rats, eukaryotes such as yeasts, and prokaryotes such as *Enterococcus faecalis*. Furthermore, proteins having an amino acid sequence of 60% or higher, preferably 75% or higher, more preferably 90% or higher homology to the amino acid sequences of these MVKs and can remove MVA by an enzymatic reaction can also be suitably selected and used as the enzymes, taking into account stability, reactivity, productivity, and the like of these enzymes. For example, a protein having an amino acid sequence encoded by a nucleotide sequence of SEQ ID NO: 5 derived from *Saccharomyces cerevisiae* (Curr. Genet. 1991 January; 19[1]: 9-14) is an enzyme that catalyzes the reaction represented by Reaction Formula 21 and can therefore be used. Furthermore, enzymes that can remove MVA by an enzymatic reaction can also be used which are obtained by modifying a nucleotide sequence or an amino acid sequence of MVK to include deletion, addition, and/or substitution in the amino acid sequence to improve performances such as reactivity, stability, productivity, and purification efficiency. Enzymes that can remove MVA by an enzymatic reaction can also be used in which MVK is chemically modified with PEG or the like or polymerized to improve performances such as reactivity and stability.

Enzymes that can be used in the step of removing MVA can be produced according techniques known to those skilled in the art as described about the production of HMGR above. For example, MVK is produced by culturing yeasts, archaea, eubacteria, and the like that produce MVK to accumulate MVK in the cells or to secrete MVK into the culture broth, and then the MVK can be purified according to common enzyme purification methods.

When an enzymatic reaction is used in the step of removing MVA from a test solution, phosphate donors, magnesium compounds, acids, alkalis, buffer components, salts, surfactants, chelating agents, metal ions, saccharides, amino acids, peptides, proteins, nucleic acids, dyes, alcohols, polyols, organic solvents, preservatives, and the like can be suitably selected as components and added in appropriate amounts to the reaction mixture in addition to the enzyme, so that MVA should be appropriately removed by the enzyme, and that influences of impurities derived from raw materials constituting the test solution and the reaction mixture can be avoided. As phosphate donors, nucleotides such as GTP, CTP, TTP, UTP, and ITP may be used in addition to ATP. Magnesium compounds are not limited so long as these compounds contain magnesium ions, and magnesium sulfate, magnesium chloride, magnesium acetate, magnesium nitrate and the like may be used. Manganese compounds may also be used instead of magnesium compounds.

When an enzymatic reaction is used in the step of removing MVA from a test solution, the reaction conditions can be suitably adjusted. For example, 20° C. to 55° C., preferably 25° C. to 45° C., more preferably 30° C. to 40° C. can be used as the reaction temperature, 0.5 minutes to 24 hours, preferably one minute to 30 minutes, more preferably one minute to five minutes can be used as the reaction time, and pH 6.0 to 11.0, preferably pH 7.5 to 11.0, more preferably pH 8.5 to 10.5 can be used as pH. Furthermore, the concentration of a buffer component in the total volume of the reaction mixture can be 5 to 500 mM, preferably 10 to 200 mM, more preferably 20 to 100 mM, for example, when Tris buffer, HEPES buffer, phosphate buffer, carbonate buffer, glycine buffer, CAPS buffer, or CAPSO buffer is used. When the phosphate donor is ATP, the concentration can be 0.01 to 20 mM, preferably 0.1 to 10 mM. When the magnesium compound is magnesium chloride, the concentration thereof can be 0.01 to 20 mM, preferably 0.1 to 10 mM, and the concentration of MVK can be 0.01 to 1000 U/mL, preferably 0.1 to 10 U/mL. Here, one unit of enzyme activity is defined as the amount of an enzyme required to produce one micromole of NADH per minute at 37° C. in the presence of MVA, ATP, NAD, glucose, ADP-dependent hexokinase, and glucose-6-phosphate dehydrogenase.

When an enzymatic reaction is terminated by alkali treatment after using the enzymatic reaction in the step of removing MVA from a test solution, for example, NaOH is added to the reaction mixture at a concentration of 0.01 to 0.5 M, preferably 0.02 to 0.2 M to adjust pH to a higher level and thereby inactivate the enzyme. After 0.1 to 10 minutes, preferably 0.5 to five minutes, a buffer such as glycine is added to the reaction mixture at a concentration of 0.01 to 0.5 M, preferably 0.02 to 0.2 M, and an acid such as citric acid is added to the reaction mixture at a concentration of 0.005 to 0.1 M, preferably 0.01 to 0.05 M, to adjust pH, so that the enzyme that catalyzes the reactions represented by Reaction Formulas 1 and 2 can react. Then, the enzyme catalyzing the reactions represented by Reaction Formulas 1 and 2 is allowed to act, and the concentration of HMG-CoA can be measured.

Furthermore, when EDTA is added as a chelating agent to inhibit a reaction of an enzyme after an enzymatic reaction is used in the step of removing MVA from a test solution, EDTA is added in a molar quantity of 0.5 to 50 times, preferably one to 20 times the molar quantity of magnesium ions added to the reaction mixture for the enzymatic reaction. Then, the enzyme that catalyzes the reactions represented by Reaction Formulas 1 and 2 is allowed to act, and the concentration of HMG-CoA can be measured.

When MVA is contained in a measuring reagent for measuring MVA and/or HMG-CoA, the above-mentioned technique can be used to remove MVA and obtain a measuring reagent containing substantially no MVA. When MVK, for example, is used in the above-mentioned technique: a technique of carrying out an enzymatic reaction using one to 100 days, preferably one to 30 days as the reaction time, 2° C. to 20° C. as the reaction temperature, and 0.0001 to 1 U/mL as the concentration of MVK; or a technique of carrying out an enzymatic reaction using one minute to three hours as the reaction time, 25° C. to 40° C. as the reaction temperature, and 0.001 to 10 U/mL as the concentration of MVK; can be used (for example, see Examples 18 and 19 described later). For example, a measuring reagent can be used which contains MVA decreased to 50% or lower, preferably 30% or lower, more preferably 20% or lower as compared with before the removal of MVA. When the measuring reagent thus obtained is used for measuring MVA and/or HMG-CoA, the blank reaction is decreased, and the S/N ratio is improved, and therefore, the measurement sensitivity is also improved.

Meanwhile, when both MVA and HMG-CoA are present in a test solution in the measuring method according to the present invention, and the concentration of MVA alone is to be measured: 1) two samples, i.e., a sample obtained by removing MVA from the test solution and a sample from which MVA is not removed, are prepared, an enzyme that catalyzes the reactions represented by Reaction Formulas 1 and 2 is allowed to act on either sample, and MVA in the test solution is calculated from the difference between the measured amounts of these samples; or 2) it is desirable to perform the step of removing HMG-CoA in the test solution before the step of allowing an enzyme that catalyzes the reactions represented by Reaction Formulas 1 and 2 to act on the test solution. In the above 1), a sample obtained by removing MVA from the test solution can be prepared using the above-described step of removing MVA from the test solution. The step of removing HMG-CoA from the test solution for the above 2) is not particularly limited so long as HMG-CoA can be removed without removing MVA, which is the analyte, and examples thereof include methods of treating a test solution with an adsorbent specific to HMG-CoA or a membrane selective to HMG-CoA and methods of converting HMG-CoA to a substance that is not involved in the reaction represented by Reaction Formula 2. Examples of the methods of converting HMG-CoA to a substance that is not involved in the reaction represented by Reaction Formula 2 include methods using an enzymatic reaction. Examples of methods using an enzymatic reaction include: a method of converting HMG-CoA to acetoacetic acid and acetyl coenzyme A using an enzyme such as hydroxymethylglutaryl coenzyme A lyase (EC4.1.3.4: hereinafter also referred to as HMGL), as shown in the following Reaction Formula 22:

[Formula 28]

(Reaction Formula 22)

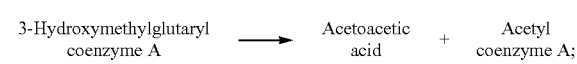

a method of converting HMG-CoA to 3-hydroxymethylglutaric acid and coenzyme A using an enzyme such as hydroxymethylglutaryl coenzyme A hydrolase (EC3.1.2.5), as shown in the following Reaction Formula 23:

[Formula 29]

(Reaction Formula 23)

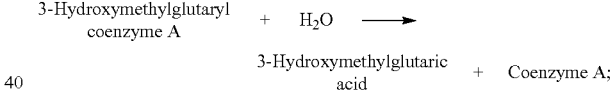

and a method of converting HMG-CoA to acetyl coenzyme A and acetoacetyl coenzyme A using an enzyme such as hydroxymethylglutaryl coenzyme A synthetase (EC2.3.3.10), as shown in the following Reaction Formula 24:

[Formula 30]

(Reaction Formula 24)

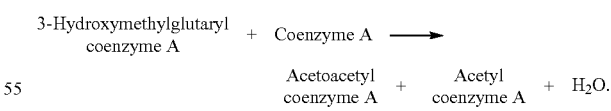

In the step of removing HMG-CoA by an enzymatic reaction, pH, buffer, salt concentration, and the like of the reaction mixture can be optimized. Furthermore, an enzyme that further acts on a product (for example, acetoacetic acid decarboxylase (EC4.1.1.4), which degrades acetoacetic acid produced by the Reaction Formula 22, into carbon dioxide and acetic acid) can be added if necessary.

When the step of removing HMG-CoA from a test solution using an enzymatic (for example, HMGL) reaction is performed as described above, and the test solution is subjected as it is to the enzyme cycling reaction represented by a combination of Reaction Formulas 1 and 2, the above-mentioned enzyme (for example, HMGL) acts on HMG-CoA, which is converted from MVA by the Reaction Formula 1. After the step of removing HMG-CoA from the test solution using an enzymatic reaction, it is therefore desirable to remove the used enzyme or terminate the reaction of the enzyme. For example, the enzyme can be removed by ultrafiltration using a membrane. When the enzyme is HMGL, for example, HMGL can be removed by ultrafiltration using a membrane having a molecular weight cut off of 5000 to 30,000 without removing MVA. Furthermore, to terminate the reaction of the enzyme, methods for inactivating an intended enzyme without degrading MVA, such as heat treatment, acid treatment, alkali treatment, and addition of a substance that inactivates the enzyme, methods of adding a substance that inhibits the activity of an intended enzyme (for example, HMGL) but does not inhibit the activity of an enzyme that catalyzes the reactions represented by Reaction Formulas 1 and 2 (for example, HMGR) to the reaction mixture, and the like can be used. Of the above-mentioned methods of removing the enzyme or terminating the reaction of the enzyme, the method by alkali treatment is preferred because an isolation procedure is not required, and a series of procedures can be performed in the same reaction vessel using an automated analyzer. The term "isolation procedure" used herein refers to a column chromatography procedure, a membrane filtration procedure, an adsorption isolation procedure, an extraction isolation procedure, a precipitation isolation procedure, and the like during a series of steps of measuring MVA in a test solution.

The enzyme that can be used in the step of removing HMG-CoA is not limited so long as the enzyme can convert HMG-CoA to a substance that is not involved in the reaction represented by Reaction Formula 2. For example, the above-mentioned enzymes that catalyze the reactions represented by Reaction Formulas 22 to 24 can be used. Specific examples of such enzymes include HMGLs derived from mammals such as humans, mice, and rats and prokaryotes such as *Pseudomonas mevalonii*. Furthermore, proteins having an amino acid sequence of 60% or higher, preferably 75% or higher, more preferably 90% or higher homology to the amino acid sequences of these HMGLs and can remove HMG-CoA by an enzymatic reaction can also be suitably selected and used as the enzymes, taking into account stability, reactivity, productivity, and the like of these enzymes. For example, the inventor found that a protein derived from *Pseudomonas putida* KT2440 (ATCC47054) having an amino acid sequence of SEQ ID NO: 7, which has 60% homology to the HMGL derived from *Pseudomonas mevalonii* having an amino acid sequence of SEQ ID NO: 6 (J Bacteriol. 1989 December; 171(12): 6468-72), is an enzyme that catalyzes the reaction represented by Reaction Formula 22. Therefore, this enzyme can be used. Furthermore, an enzyme that can remove HMG-CoA by an enzymatic reaction and is obtained by modifying a nucleotide sequence or an amino acid sequence of HMGL to include deletion, addition, and/or substitution in the amino acid sequence, thereby improving performances such as reactivity, stability, productivity, and purification efficiency, can also be used. Enzymes that can remove HMG-CoA by an enzymatic reaction can also be used in which HMGL is chemically modified with PEG or the like or polymerized to improve performances such as reactivity and stability.

Enzymes that can be used in the step of removing HMG-CoA can be produced according to techniques known to those skilled in the art as described about the production of HMGR above. For example, HMGL is produced by culturing yeasts, archaea, eubacteria, and the like that produce HMGL to accumulate HMGL in the cells or to secrete HMGL in the culture broth, and then the HMGL can be purified according to common enzyme purification methods.

When an enzymatic reaction is used in the step of removing HMG-CoA from a test solution, acids, alkalis, buffer components, salts, surfactants, chelating agents, metal ions, saccharides, amino acids, peptides, proteins, nucleic acids, dyes, alcohols, polyols, organic solvents, preservatives, and the like can be suitably selected as components and added to the reaction mixture in appropriate amounts in addition to an enzyme, so that HMG-CoA should be appropriately removed by the enzyme, and that influences of impurities derived from raw materials constituting the test solution and the reaction mixture can be avoided.

When an enzymatic reaction is used in the step of removing MVA from a test solution, the reaction conditions can be suitably adjusted. For example, 20° C. to 55° C., preferably 25° C. to 45° C., more preferably 30° C. to 40° C. can be used as the reaction temperature, 0.5 minutes to 24 hours, preferably one minute to 30 minutes, more preferably one minute to five minutes can be used as the reaction time, and pH 6.0 to 11.0, preferably pH 7.5 to 11.0, more preferably pH 8.5 to 10.5 can be used as pH. Furthermore, the concentration of a buffer component in the total volume of the reaction mixture can be 0.1 to 500 mM, preferably 1 to 100 mM, more preferably 3 to 50 mM, for example, when Tris buffer, HEPES buffer, phosphate buffer, carbonate buffer, glycine buffer, CAPS buffer, or CAPSO buffer is used. The concentration of HMGL can be 0.01 to 1000 U/mL, preferably 0.1 to 10 U/mL. Here, one unit of enzyme activity is defined as the amount of an enzyme required to decrease one micromole of NADH per minute at 37° C. in the presence of HMG-CoA, NADH, and 3-hydroxybutyrate dehydrogenase.

When the enzymatic reaction is terminated by alkali treatment after using an enzymatic reaction in the step of removing HMG-CoA from a test solution, for example, NaOH is added to the reaction mixture at a concentration of 0.01 to 0.5 M, preferably 0.02 to 0.2 M to adjust pH to a higher level and thereby inactivate the enzyme. After 0.1 to 10 minutes, preferably 0.5 to five minutes, a buffer such as glycine is added to the reaction mixture at a concentration of 0.01 to 0.5 M, preferably 0.02 to 0.2 M, and an acid such as citric acid is added to the reaction mixture at a concentration of 0.005 to 0.1 M, preferably 0.01 to 0.05 M to adjust pH, so that the enzyme that catalyzes the reactions represented by Reaction Formulas 1 and 2 can react. Then, the enzyme that catalyzes the reactions represented by Reaction Formulas 1 and 2 is allowed to act, and the concentration of MVA can be measured.

When HMG-CoA is contained in a measuring reagent for measuring MVA and/or HMG-CoA, the above-mentioned technique can be used to remove HMG-CoA and obtain a measuring reagent containing substantially no HMG-CoA. When HMGL, for example, is used in the above-mentioned technique: a technique of carrying out an enzymatic reaction using one to 100 days, preferably one to 30 days as the reaction time, 2° C. to 20° C. as the reaction temperature, and 0.0001 to 1 U/mL as the concentration of HMGL; or a technique of carrying out an enzymatic reaction using one minute to three hours as the reaction time, 25° C. to 40° C. as the reaction temperature, and 0.001 to 10 U/mL as the concentration of HMGL; can be used (for example, see Example 20 described later). When the measuring reagent thus obtained is used for measuring MVA and/or HMG- CoA, the blank reaction is decreased, and the S/N ratio is improved, and therefore, the measurement sensitivity is also improved.

The present invention also provides measuring reagents for measuring MVA, HMG-CoA, or CoA. In the present specification, the term "measuring reagent" (also referred to as "measurement reagent") includes not only one reagent but also a combination of reagents consisting of two or more reagents. When the measuring reagent consists of two or more reagents, all the reagent can be used simultaneously at the time of measurement of an analyte or each of the reagents can be used separately at individual steps. When the reagent consists of two to four measuring reagents, two or more reagents may be added simultaneously or may be added successively to the sample by selecting appropriate timings at which a required reaction is completed after the addition of each reagent, for example, at intervals of one second to 30 minutes, preferably one minute to 10 minutes.

A measuring reagent used to measure MVA and/or HMG-CoA in a test solution contains an enzyme that catalyzes the reactions represented by Reaction Formulas 1 and 2, CoA, a hydrogen acceptor X, and a hydrogen donor Y. More specifically, it contains HMGR, CoA, oxidized nicotinamide adenine dinucleotides, and reduced nicotinamide adenine dinucleotides. Furthermore, acids, alkalis, buffer components, salts, surfactants, chelating agents, metal ions, saccharides, amino acids, peptides, proteins, nucleic acids, dyes, alcohols, polyols, organic solvents, preservatives, and the like can be suitably selected and added in combination, taking into account that the measuring reagent is made preferable for an enzyme cycling reaction represented by a combination of Reaction Formulas 1 and 2, that influences of impurities in the test solution and the reaction mixture are avoided (for example, so that the composition should be the same as that of the reaction mixture in the above-mentioned method for measuring MVA and/or HMG-CoA), or that storage stability of the measuring reagent is improved.

In particular, a measuring reagent used to measure HMG-CoA in a test solution preferably contains substances used for the step of removing MVA from a test solution, more specifically, MVK and a phosphate donor in addition to the above-mentioned reagent for measuring MVA and/or HMG-CoA. Examples of such a measuring reagent include measuring reagents containing HMGR, MVK, CoA, a phosphate donor, T-NAD(P), and NAD(P)H. Here, the measuring reagent preferably consists of two or more reagents, and: MVK and a phosphate donor; and HMGR; CoA; T-NAD(P); or NAD(P)H; are contained in separate reagents. Furthermore, acids, alkalis, buffer components, salts, surfactants, chelating agents, metal ions, saccharides, amino acids, peptides, proteins, nucleic acids, dyes, alcohols, polyols, organic solvents, preservatives, and the like are suitably selected and can be added in combination to the measuring reagent to be preferably used for an enzymatic reaction for removing MVA or terminating the enzymatic reaction after removing MVA (for example, so that the composition should be the same as that of the reaction mixture in the above-mentioned HMG-CoA measuring method including the enzymatic reaction catalyzed by MVK).

In particular, a measuring reagent used to measure MVA in a test solution preferably further contains substances used in the step of removing HMG-CoA from a test solution, more specifically, HMGL in addition to the above-mentioned reagent for measuring MVA and/or HMG-CoA. Examples of such a measuring reagent include measuring reagents containing HMGR, HMGL, CoA, T-NAD(P), and NAD(P)H. Here, the measuring reagent preferably consists of two or more reagents, and HMGR and HMGL are contained in separate reagents. Furthermore, acids, alkalis, buffer components, salts, surfactants, chelating agents, metal ions, saccharides, amino acids, peptides, proteins, nucleic acids, dyes, alcohols, polyols, organic solvents, preservatives, and the like are suitably selected and can be added in combination to the measuring reagent to be preferably used for an enzymatic reaction for removing HMG-CoA or terminating the enzymatic reaction after removing HMG-CoA (for example, so that the composition should be the same as that of the reaction mixture in the above-mentioned MVA measuring method including the enzymatic reaction by HMGL).

The measuring reagent used to measure CoA in a test solution contains an enzyme that catalyzes the reactions represented by Reaction Formulas 1 and 2, MVA, a hydrogen acceptor X, and a hydrogen donor Y. More specifically, it contains HMGR, MVA, oxidized nicotinamide adenine dinucleotides, and reduced nicotinamide adenine dinucleotides. Furthermore, acids, alkalis, buffer components, salts, surfactants, chelating agents, metal ions, saccharides, amino acids, peptides, proteins, nucleic acids, dyes, alcohols, polyols, organic solvents, preservatives, and the like are suitably selected and can be added in combination to the measuring reagent, taking into account that the measuring reagent is made preferable for an enzyme cycling reaction represented by a combination of Reaction Formulas 1 and 2, that influences of impurities in a test solution and a reaction mixture are avoided (for example, so that the composition should be the same as that of the reaction mixture in the above-mentioned CoA measuring method), and that storage stability of the measuring reagent is improved.

The above-mentioned measuring reagent can be stored in forms of a solution, a frozen product of a solution, a lyophilized product, and a dissolved solution thereof, and the like. Furthermore, it is desirable that the above-mentioned measuring reagent before use consists of one to four measuring reagent solutions.

For example, a reagent for measuring MVA and HMG-CoA can consist of one to four reagents. When the reagent consists of one reagent, the reagent consists of a reagent containing at least four components of HMGR, CoA, NADH, and T-NAD. When the reagent consists of two reagents, the above-mentioned four components are suitably divided into two taking into account stability of the reagent. For example, the reagent can consist of: a reagent containing at least HMGR, CoA, and T-NAD; and a reagent containing at least NADH. When the reagent consists of three reagents, the above-mentioned four components are divided into three. For example, the reagent can consist of: a reagent containing at least HMGR and T-NAD; a reagent containing at least CoA; and a reagent containing at least NADH. When the reagent consists of four reagents, the above-mentioned four components are divided into four. For example, the reagent can consist of: a reagent containing at least HMGR; a reagent containing at least T-NAD; a reagent containing at least CoA; and a reagent containing at least NADH.

For example, when both MVA and HMG-CoA are present in a test solution, a reagent for measuring the concentration of HMG-CoA alone can consist of two to four reagents. When the reagent consists of two reagents, four components of HMGR, CoA, NADH, and T-NAD are suitably divided into: a first reagent containing at least a component essential to allow the reaction represented by Reaction Formula 21 catalyzed by MVK to progress; and a second reagent containing at least a component for terminating the reaction catalyzed by MVK; taking into account stability of the reagent and the like, so that an enzyme cycling reaction starts when the second reagent is added. For example, the reagent can be composed so that the first reagent should contain MVK, ATP, and magnesium chloride, and the second reagent should contain EDTA, HMGR, CoA, NADH, and T-NAD. When the reagent consists of three reagents, four components of HMGR, CoA, NADH, and T-NAD can be divided into: a first reagent containing at least a component essential to allow the reaction represented by Reaction Formula 21 catalyzed by MVK to progress; a second reagent containing at least a component for terminating the reaction catalyzed by MVK; and a third reagent containing a component for allowing an enzyme cycling reaction to be started after the addition of the third reagent; taking into account stability of the reagent and the like. Alternatively, when the reagent consists of three reagents, four components can be suitably divided into: a first reagent containing at least a component essential to allow the reaction represented by Reaction Formula 21 catalyzed by MVK to progress; a third reagent containing at least a component for terminating the reaction catalyzed by MVK and a component for allowing an enzyme cycling reaction to be started after the addition of the third reagent; and a second reagent containing other components; taking into account stability of the reagent and the like. When the reagent consists of four reagents, four components of HMGR, CoA, NADH, and T-NAD can be divided into: a first reagent containing at least a component essential to allow the reaction represented by Reaction Formula 21 catalyzed by MVK to progress; a second reagent containing at least a component for terminating the reaction catalyzed by MVK; a fourth reagent containing a component for allowing an enzyme cycling reaction to be started after the addition of the fourth reagent; and a third reagent containing other components; taking into account stability of the reagent and the like. Alternatively, when the reagent consists of four reagents, the four components can be divided into a first reagent containing at least a component essential to allow the reaction represented by Reaction Formula 21 catalyzed by MVK to progress; a third reagent containing at least a component for terminating the reaction catalyzed by MVK; a fourth reagent containing a component for allowing an enzyme cycling reaction to be started after the addition of the fourth reagent; and a second reagent containing other components; taking into account stability of the reagent and the like. Alternatively, when the reagent consists of four reagents, the four components can be divided into a first reagent containing at least a component essential to allow the reaction represented by Reaction Formula 21 catalyzed by MVK to progress; a fourth reagent containing at least a component for terminating the reaction catalyzed by MVK and a component for allowing an enzyme cycling reaction to be started after the addition of the fourth reagent; and a second reagent and a third reagent containing other components; taking into account stability of the reagent and the like.

For example, when both MVA and HMG-CoA are present in a test solution, a reagent for measuring the concentration of MVA alone can consist of two to four reagents. When the reagent consists of two reagents, four components of HMGR, CoA, NADH, and T-NAD are suitably divided into: a first reagent containing at least a component essential to allow the reaction represented by Reaction Formula 22 catalyzed by HMGL to progress; and a second reagent containing at least a component for inactivating HMGL and a component for allowing an enzyme cycling reaction to be started after the addition of the second reagent; taking into account stability of the reagent and the like. When the reagent consists of three reagents, four components of HMGR, CoA, NADH, and T-NAD can be divided into: a first reagent containing at least a component essential to allow the reaction represented by Reaction Formula 22 catalyzed by HMGL to progress; a second reagent containing at least a component for inactivating HMGL; and a third reagent containing a component for allowing an enzyme cycling reaction to be started after the addition of the third reagent; taking into account stability of the reagent and the like. Alternatively, when the reagent consists of three reagents, four components can be divided into: a first reagent containing at least a component essential to allow the reaction represented by Reaction Formula 22 catalyzed by HMGL to progress; a third reagent containing at least a component for inactivating HMGL and a component for allowing an enzyme cycling reaction to be started after the addition of the third reagent; and a second reagent containing other components; taking into account stability of the reagent and the like. When the reagent consists of four reagents, four components of HMGR, CoA, NADH, and T-NAD can be divided into: a first reagent containing at least a component essential to allow the reaction represented by Reaction Formula 22 catalyzed by HMGL to progress; a second reagent containing at least a component for inactivating HMGL; a fourth reagent containing a component for allowing an enzyme cycling reaction to be started after the addition of the fourth reagent; and a third reagent containing other components; taking into account stability of the reagent and the like. For example, when the reagent consists of four reagents, the reagent can consist of: a first reagent containing HMGL; a second reagent containing sodium hydroxide; a third reagent containing buffer components, acids, HMGR, CoA, and T-NAD; and a fourth reagent containing NADH. Alternatively, when the reagent consists of four reagents, the four components can be divided into: a first reagent containing at least a component essential to allow the reaction represented by Reaction Formula 22 catalyzed by HMGL to progress; a third reagent containing at least a component for inactivating HMGL; a fourth reagent containing a component for allowing an enzyme cycling reaction to be started after the addition of the fourth reagent; and a second reagent containing other components; taking into account stability of the reagent and the like. Alternatively, when the reagent consists of four reagents, the four components can be divided into: a first reagent containing at least a component essential to allow the reaction represented by Reaction Formula 22 catalyzed by HMGL to progress; a fourth reagent containing at least a component for inactivating HMGL and a component for allowing an enzyme cycling reaction to be started after the addition of the fourth reagent; and a second reagent and a third reagent containing other components; taking into account stability of the reagent and the like.

In general, when the amount of a substance A present in a test solution is measured using a measuring reagent by converting the amount to the intensity of a signal such as absorbance, the amount of luminescence, or the quantity of electricity, a calibration curve obtained by using a test solution containing a known amount of the substance A (referred to as a "calibrator") is required. The calibration curve represents a relationship between signal intensity and the concentration of the substance A. Therefore, in a usual laboratory, an unknown amount of a substance A in a test solution is measured using not only measuring reagents but also a calibrator.

When the amount of a substance A is measured at different laboratories, there may be a gap between the amounts of the substance A in a test solution measured at a "laboratory a" and the amounts measured at a "laboratory b". This gap occurs because of differences in measuring reagents and measurement procedures thereof, measuring apparatuses, calibrators, measurers, and the like. Minimizing these gaps between laboratories is required at clinical laboratories and the like in medical practice. To minimize these gaps between laboratories, it is sufficient to establish traceability of measurement of a substance A, i.e., establish a reference material of the substance A and standard method for measuring the substance A, assign the value of the substance A concentration present in a routinely used calibrator based on the reference material and the standard method to measure the substance by a routine measuring method (Clin Chem. 2009 June; 55(6): 1067-75).

Here, to establish the traceability of MVA measurement, a reference material and a standard measuring method need to be established first. In this regard, precise purity of MVA and D,L-MVA (for example, D-Mevalonolactone [Product Code M1374] of Tokyo Chemical Industry Co., Ltd and (±)-Mevalonolactone [DL-mevalonic acid lactone] [Product Number M4667] of Sigma) marketed as general reagents is unknown. As to their purity measuring methods, only methods with low specificity, such as titration, methods that cannot measure absolute amounts without a reference material, such as gas chromatography (GC), methods using polarimetry or NMR that measure only the content ratio of optical isomers (J Lipid Res. 1982 May; 23(4): 645-52), and a method of measuring decreases of NADH by coupling pyruvate kinase and lactate dehydrogenase to MVK (Methods Enzymol. 1969; 15: 393-454), which appears to have inadequate precision as described later, are known. Therefore, there has been no appropriate reference material or standard measuring method. Accordingly, as a candidate standard measuring method, the inventor developed two methods for measuring an accurate amount of MVA based on the absorbance coefficient of NAD(P)H in a reaction system in which NAD(P)H is increased, utilizing enzyme specificity.

One method is a method using reactions represented by Reaction Formula 21 using MVK:

[Formula 31]

(Reaction Formula 21)

Reaction Formula 25 using ADP-dependent hexokinase (ADP-specific glucokinase [EC2.7.1.47]):

[Formula 32]

(Reaction Formula 25)

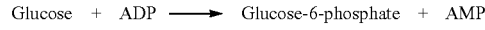

Reaction Formula 26 using glucose-6-phosphate dehydrogenase (EC1.1.1.49):

[Formula 33]

(Reaction Formula 26)

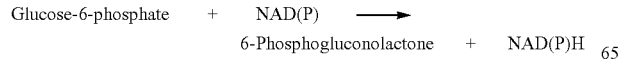

and Reaction Formula 27 using 6-phosphogluconolactonase (EC3.1.1.31):

[Formula 34]

(Reaction Formula 27)

in combination, wherein all MVA (D-MVA) molecules can be converted to NAD(P)H, and an accurate amount of MVA(D-MVA) can be measured using the absorbance coefficient of NAD(P)H. Here, the reaction represented by Reaction Formula 27 progresses without being catalyzed by an enzyme, when pH is adjusted, (for example, to 8.0 or higher, preferably 8.5 or higher, more preferably 9.0 or higher). Therefore, 6-phosphogluconolactonase (EC3.3.3.31) may not be used in some cases. Furthermore, it is possible to use a substrate on which ADP-dependent hexokinase acts instead of glucose in the reaction represented by Reaction Formula 25, and perform a reaction corresponding to Reaction Formula 26 using a dehydrogenase to the product.

Another method is a method using a reaction represented by Reaction Formula 11 using HMGR:

[Formula 35]

(Reaction Formula 11)

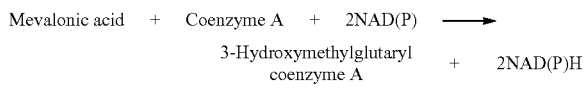

preferably using Reaction Formula 22 using HMGL:

[Formula 36]

(Reaction Formula 22)

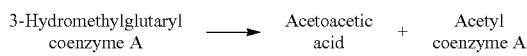

in combination, wherein all MVA(D-MVA) molecules can be converted to NAD(P)H, and an accurate amount of MVA(D-MVA) can be measured based on the absorbance coefficient of NAD(P)H. Here, Reaction Formula 22 can be replaced with Reaction Formula 23 using hydroxymethylglutaryl coenzyme A hydrolase (EC3.1.2.5):

[Formula 37]

(Reaction Formula 23)

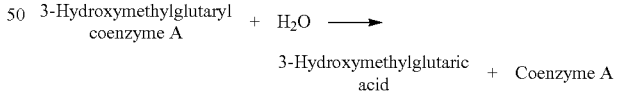

or Reaction Formula 24 using hydroxymethylglutaryl coenzyme A synthetase (EC2.3.3.10):

[Formula 38]

(Reaction Formula 24)

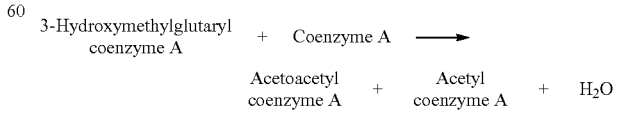

In an aqueous solution, it is considered that MVA is in an equilibrium state of lactone in which a hydroxy group and a carboxyl group in a molecule are dehydrated and hydroxycarboxylic acid generated by hydrolysis of lactone. It is considered that MVK or HMGR acts on not MVA of lactone state but on MVA of hydroxycarboxylic acid state, in view of a substrate involved in the reaction and a structure of the product. The optimal pH of a reaction from MVA to mevalonic acid phosphate by MVK and a reaction from MVA to HMGcoA by HMGR is in a high pH region. One of the reasons why this pH region is optimal is that lactone is hydrolyzed with a high pH region, and the equilibrium thereby shifts towards hydroxycarboxylic acid. Therefore, to measure MVA accurately by an enzymatic reaction using MVK or HMGR, it is important to shift the equilibrium towards hydroxycarboxylic acid. For this purpose, lactonase for hydrolyzing lactone of MVA may be added, but it is desirable in view of convenience that pH of the reaction is in the high pH region (pH of a reagent or a reaction mixture is 8.5 or higher, preferably 9.0 or higher, more preferably 9.5 or higher, further preferably 10.0 or higher). Meanwhile, optimal pH of a reaction by dehydrogenase or the like to produce NAD(P)H is in a high pH region so long as stability of components involved in a reaction, such as an enzyme and an substrate, can be maintained. Also, it is generally known that optimal pH of a reaction to produce NAD(P) is in the low pH region so long as stability of components involved in a reaction, such as an enzyme and an substrate, can be maintained. When an increase of NAD(P)H by dehydrogenase is measured, it is desirable that pH is in a high pH region. When a decrease of NAD(P)H is measured, it is desirable that pH is in a low pH region. In the above-described method of measuring a decrease in NADH by coupling pyruvate kinase and lactate dehydrogenase to MVK, however, there is a problem of contradictory pH setting that the high pH region is desirable in a reaction catalyzed by MVK, whereas the low pH region is desirable in a reaction catalyzed by lactate dehydrogenase (pH was set at 7.3 to 7.4 in Methods Enzymol. 1969; 15: 393-454). In addition, the amount of NADH that can be added to a reaction system is limited due to a problem of absorbance, and there are also problems of a reaction with high blank absorbance and others. Therefore, this reaction system is inadequate to measure an accurate amount of MVA. Furthermore, as described above, when accurately measuring MVA by an enzymatic reaction using MVK or HMGR, it is important that reaction pH is in a high pH region, for example, pH of a reagent or a reaction mixture is 8.5 or higher, preferably 9.0 or higher, more preferably 9.5 or higher, further preferably 10.0 or higher to shift the equilibrium towards hydroxycarboxylic acid. However, in view of stability of a coenzyme (for example, CoA) and stability and reactivity of MVK, HMGR, and coupling enzymes used with MVK and HMGR, one could never think that a reaction can progress stably and sufficiently in such a high pH region. To their surprise, however, the inventor found that the reaction progresses stably and adequately in the above-mentioned reaction system using MVK or HMGR in which NAD(P)H is increased, and found a method for measuring an accurate amount of MVA based on the absorbance coefficient of NAD(P)H by a short-time (for example, within 30, 15, or 10 minutes) reaction with high precision.

By these methods, a reference material with an accurate assigned value of MVA concentration can be provided, and traceability of MVA measurement can be established.

In the case of CoA, similar to the case of MVA, a reference material with an accurate assigned value of CoA concentration can be provided and traceability of CoA measurement can be established by a method of using reactions represented by reaction formulas for HMGR and HMGL in combination, a method of using reactions represented by reaction formulas for HMGR and hydroxymethylglutaryl coenzyme A hydrolase in combination, or a method of using reactions represented by reaction formulas for HMGR and hydroxymethylglutaryl coenzyme A synthetase in combination.

In the case of HMG-CoA, similar to the case of MVA, a reference material with an accurate assigned value of HMG-CoA concentration can be provided, and traceability of measurement of HMG-CoA can be established by a method of producing MVA and CoA from HMG-CoA by HMGR and using the produced MVA in reactions represented by above-mentioned reaction formulas for the MVK, ADP-dependent hexokinase, glucose-6-phosphate dehydrogenase, and 6-phosphogluconolactonase in combination.

Furthermore, additives such as acids, bases, metal ions, saccharides, alcohols, amino acids, proteins, salts, buffer components, surfactants, chelating agents, blood components, and other organic compounds may be suitably added to such a reference material of MVA, CoA or HMG-CoA to improve performances such as storage stability, and the form may be a solution, a frozen product, or a lyophilized product.

EXAMPLES

Hereafter, the present invention will be more specifically described with reference to the Examples. However, the scope of the present invention is not limited to the following Examples and the like. The media and the reagents used in each Example will be summarized in Preparation Examples described later.

In tables and figures in the following Examples as well as in the present specification, when a term "D,L-mevalonic acid" or "D,L-MVA" is used, the term represents a racemic mevalonic acid, which is a mixture of the D form and the L form. When a term "mevalonic acid" or "MVA" is simply used, the term represents D-mevalonic acid or R-mevalonic acid.

Furthermore, in tables and figure in the following Examples as well as in the present specification, when a term "D,L-3-hydroxymethylglutaryl coenzyme A" or "D,L-HMG-CoA" is used, the term represents 3-hydroxymethylglutaryl coenzyme A, which is a mixture of the D form and the L form. When a term "3-hydroxymethylglutaryl coenzyme A" or "HMG-CoA" is simply used, the term represents D-3-hydroxymethylglutaryl coenzyme A or S-3-hydroxymethylglutaryl coenzyme A.

Furthermore, in Examples, M4667 manufactured by Sigma was used as D,L-MVA, and H6132 manufactured by Sigma was used as D,L-HMG-CoA, unless otherwise specified. The concentrations of MVA (i.e., concentrations of D-MVA) and the concentrations of HMG-CoA (i.e., concentrations of D-HMG-CoA) in Examples were calculated and expressed as half values of those of D,L-MVA and D,L-HMG-CoA.

When Automated Analyzer 7170S (Hitachi, Ltd.) was used for measurement, the specified measurement wavelength was used as the main wavelength, and 660 nm was used as the sub-wavelength for measurement. Similarly, when Automated Analyzer BM9020 (JEOL Ltd.) was used for measurement, the specified measurement wavelength was used as the main wavelength, and 658 nm was used as the sub-wavelength for measurement.

Example 1

Production of HMGR derived from *Pseudomonas* sp. 1-MV (FERM BP-11063)

Identification of *Pseudomonas* sp. 1-MV (FERM BP-11063)

*Pseudomonas* sp. 1-MV (FERM BP-11063) isolated from soil was identified as a *Pseudomonas* sp. closely related to *Pseudomonas migulae* based on the characteristics shown in Table 1 below and the 16S rDNA sequence (SEQ ID NO: 8) and deposited at International Patent Organism Depositary, National Institute of Advanced Industrial Science and Technology Tsukuba at Central 6, 1-1-1 Higashi, Tsukuba, Ibaraki, Japan on Nov. 13, 2008.

TABLE 1

| Culture temperature (° C.) | | 30 | |
|---|---|---|---|
| Cell morphology | | rod-shaped (0.6-0.7 × 0.9-1.2 μm) | |
| Gram staining | | − | |
| Spore formation | | − | |
| Motility | | + | |
| Colony morphology | Medium | nutrient agar | |
| | Culture time | 48 hr | |
| | Diameter | 1.0-2.0 mm | |
| | Color | Light yellow | |
| | Form | Round | |
| | Elevation | Convex | |
| | Margin | Entire | |
| | Surface texture | Smooth | |
| | Transparency | Opaque | |
| | Consistency | Buttery | |
| Growth temperature test (° C.) | 4 | + | |
| | 37 | + | |
| | 41 | − | |
| | 45 | − | |
| Catalase reaction | | + | |
| Oxidase reaction | | + | |
| Acid and/or gas production from glucose | | −/− | |
| Oxidation/fermentation (O/F) test | | −/− | |
| Lecithinase | | − | |
| Production of fluorescent pigment on King's B medium | | + | |
| Biochemical tests | Nitrate reduction | − | |
| | Indole production | − | |
| | Glucose acidification | − | |
| | Arginine dihydrolase | + | |
| | Urease | − | |
| | Esculin hydrolysis | − | |
| | Gelatin hydrolysis | − | |
| | β-Galactosidase | − | |
| | Cytochrome oxidase | + | |
| Assimilation tests | Glucose | + | |
| | L-Arabinose | + | |
| | D-Mannose | + | |
| | D-Mannitol | + | |
| | N-Acetyl-D-glucosamine | − | |
| | Maltose | − | |
| | Potassium gluconate | + | |
| | n-Capric acid | + | |
| | Adipic acid | − | |
| | dl-Malic acid | + | |
| | Sodium citrate | + | |
| | Phenyl acetate | + | |

Production of HMGR Derived from *Pseudomonas* sp. 1-MV (FERM BP-11063)

Three 500-mL conical flasks each containing 167 mL of Medium A were prepared, and about one third of one colony of *Pseudomonas* sp. 1-MV (FERN BP-11063) was inoculated in each of the flasks. The bacteria were cultured in these conical flasks at 28° C. for approximately 18 hours with shaking. After the culture, the culture broth was centrifuged (8 krpm, 20 min) to collect bacteria, and the bacterial cells were suspended in 30 mL of 10 mM Tris hydrochloride buffer (pH 7.5), disrupted by ultrasonication, and solubilized. After solubilization, the solution was centrifuged (15 krpm, 50 min) to obtain a crude enzyme solution.

The obtained crude enzyme solution was adsorbed to DEAE Sepharose FF Column (14.5×90 mm) equilibrated with 10 mM Tris hydrochloride buffer (pH 7.5) and eluted with NaCl at a gradient of 0→0.5 M to collect a fraction having HMGR activity. Ammonium sulfate was added to the obtained fraction at 13%, and the fraction was adsorbed to Phenyl Sepharose FF Column (14.5×90 mm) equilibrated with 12% ammonium sulfate and 10 mM Tris hydrochloride buffer (pH 7.5) and eluted at gradients of 12% ammonium sulfate and 0% ethylene glycol→0% ammonium sulfate and 20% ethylene glycol to collect a fraction having HMGR activity. The obtained fraction was dialyzed against 10 mM Tris hydrochloride buffer (pH 7.5), adsorbed to Blue Sepharose CL6B Column (14.5×90 mm) equilibrated with the 10 mM Tris hydrochloride buffer (pH 7.5), and eluted at gradients of 0 M NaCl and 0% ethylene glycol→1 M NaCl and 20% ethylene glycol to collect a fraction having HMGR activity. The fraction was dialyzed against 10 mM Tris hydrochloride buffer (pH 7.5), then subjected to ultrafiltration with a membrane having a molecular weight cut off of 10,000 to concentrate the fraction to obtain 17 U of purified HMGR.

Method for Measuring HMGR Activity 0.45 mL of Reagent B was poured into a test tube and preliminarily heated at 37° C. for five minutes, 0.05 mL of an enzyme solution was added, and the mixture was reacted at 37° C. for five minutes. After completion of the reaction, 1 mL of 0.1 N HCl was added to terminate the reaction, and absorbance (Aa) at a wavelength of 550 nm was measured. The same procedure was further performed using an enzyme dilution buffer (10 mM Tris hydrochloride buffer (pH 9), 0.1% Tween 80) as a blank instead of an enzyme solution, and absorbance (Ab) was measured. From the difference between these absorbances (Aa-Ab), 1 U of enzyme activity per milliliter of the enzyme solution is calculated as U/mL=0.316×(Aa-Ab). It should be noted that one unit of enzyme activity was defined as the amount of an enzyme required to produce one micromole of NADH at 37° C. per minute, and the enzyme solution was diluted with the enzyme dilution buffer as required.

Example 2

Production of HMGR derived from *Variovorax* sp. 5-MV (FERM BP-11064)

Identification of *Variovorax* sp. 5-MV (FERM BP-11064)

*Variovorax* sp. 5-MV (FERM BP-11064) isolated from soil was identified as a *Variovorax* sp. belonging to the genus *Variovorax* based on the characteristics shown in Table 2 below and the 16S rDNA sequence (SEQ ID NO: 9) and deposited at International Patent Organism Depositary, National Institute of Advanced Industrial Science and Technology Tsukuba at Central 6, 1-1-1 Higashi, Tsukuba, Ibaraki, Japan on Nov. 13, 2008.

TABLE 2

| Culture temperature (° C.) | 30 |
|---|---|
| Cell morphology | rod-shaped (0.6-0.7 × 1.5 2.0 μm) |

TABLE 2-continued

| | | |
|---|---|---|
| Gram staining | | – |
| Spore formation | | – |
| Motility | | + |
| Colony morphology | Medium | nutrient agar |
| | Culture time | 48 hr |
| | Diameter | 1.0-2.0 mm |
| | Color | Yellow |
| | Form | Round |
| | Elevation | Convex |
| | Margin | Entire |
| | Surface texture | Smooth |
| | Transparency | Opaque |
| | Consistency | Viscous |
| Growth temperature test (° C.) | 37 | + |
| | 45 | – |
| Catalase reaction | | + |
| Oxidase reaction | | – |
| Acid and/or gas production from glucose | | –/– |
| Oxidation/fermentation (O/F) test | | –/– |
| Anaerobic growth | | – |
| Biochemical tests | Nitrate reduction | – |
| | Indole production | – |
| | Glucose acidification | – |
| | Arginine dihydrolase | – |
| | Urease | – |
| | Esculin hydrolysis | – |
| | Gelatin hydrolysis | – |
| | β-Galactosidase | – |
| | Cytochrome oxidase | – |
| Assimilation tests | Glucose | + |
| | L-Arabinose | + |
| | D-Mannose | + |
| | D-Mannitol | + |
| | N-Acetyl-D-glucosamine | + |
| | Maltose | – |
| | Potassium gluconate | + |
| | n-Capric acid | + |
| | Adipic acid | – |
| | dl-Malic acid | + |
| | Sodium citrate | – |
| | Phenyl acetate | – |

Production of HMGR Derived from *Variovorax* sp. 5-MV (FERM BP-11064)

10 U of purified HMGR was obtained from the above-described *Variovorax* sp. 5-MV (FERM BP-11064) by the same technique as described in Example 1, except that Medium A was replaced with Medium B.

Example 3

Production of HMGR derived from *Delftia* sp. 12-MV (FERM BP-11065)

Identification of *Delftia* sp. 12-MV (FERM BP-11065)

*Delftia* sp. 12-MV (FERM BP-11065) isolated from soil was identified as a *Delftia* sp. closely related to *Delftia acidovorans* based on the characteristics shown in Table 3 below and the 16S rDNA sequence (SEQ ID NO: 10) and deposited at International Patent Organism Depositary, National Institute of Advanced Industrial Science and Technology Tsukuba at Central 6, 1-1-1 Higashi, Tsukuba, Ibaraki, Japan on Nov. 13, 2008.

TABLE 3

| | | |
|---|---|---|
| Culture temperature (° C.) | | 30 |
| Cell morphology | | rod-shaped (0.5-0.6 × 0.9-1.0 μm) |

TABLE 3-continued

| | | |
|---|---|---|
| Gram staining | | – |
| Spore formation | | – |
| Motility | | + |
| Colony morphology | Medium | nutrient agar |
| | Culture time | 48 hr |
| | Diameter | 3.0-4.0 mm |
| | Color | Light yellow |
| | Form | Round |
| | Elevation | Convex |
| | Margin | Rhizoid |
| | Surface texture | Smooth |
| | Transparency | Opaque |
| | Consistency | Buttery |
| Growth temperature test (° C.) | 37 | + |
| | 45 | – |
| Catalase reaction | | + |
| Oxidase reaction | | + |
| Acid and/or gas production from glucose | | –/– |
| Oxidation/fermentation (O/F) test | | –/– |
| Biochemical tests | Nitrate reduction | + |
| | Indole production | – |
| | Glucose acidification | – |
| | Arginine dihydrolase | – |
| | Urease | – |
| | Esculin hydrolysis | – |
| | Gelatin hydrolysis | – |
| | β-Galactosidase | – |
| | Cytochrome oxidase | + |
| Assimilation tests | Glucose | – |
| | L-Arabinose | – |
| | D-Mannose | – |
| | D-Mannitol | + |
| | N-Acetyl-D-glucosamine | – |
| | Maltose | – |
| | Potassium gluconate | + |
| | n-Capric acid | + |
| | Adipic acid | + |
| | dl-Malic acid | – |
| | Sodium citrate | – |
| | Phenyl acetate | + |

Production of HMGR Derived from *Delftia* sp. 12-MV (FERM BP-11065)

60 U of purified HMGR was obtained from the above-described *Delftia* sp. 12-MV (FERM BP-11065) by the same technique as described in Example 1.

Example 4

Production of HMGR derived from *Comamonas* sp. 25-MV (FERM BP-11066)

Identification of *Comamonas* sp. 25-MV (FERM BP-11066)

*Comamonas* sp. 25-MV (FERM BP-11066) isolated from soil was identified as a *Comamonas* sp. closely related to *Comamonas testosteroni* based on the characteristics shown in Table 4 below and the 16S rDNA sequence (SEQ ID NO: 11) and deposited at International Patent Organism Depositary, National Institute of Advanced Industrial Science and Technology Tsukuba at Central 6, 1-1-1 Higashi, Tsukuba, Ibaraki, Japan on Nov. 13, 2008.

TABLE 4

| | |
|---|---|
| Culture temperature (° C.) | 30 |
| Cell morphology | rod-shaped (0.6-0.7 × 0.9-1.0 μm) |
| Gram staining | – |
| Spore formation | – |
| Motility | + |

TABLE 4-continued

| Colony morphology | Medium | nutrient agar |
|---|---|---|
| | Culture time | 48 hr |
| | Diameter | 3.0-4.0 mm |
| | Color | Light yellow |
| | Form | Round |
| | Elevation | Convex |
| | Margin | Entire |
| | Surface texture | Smooth |
| | Transparency | Opaque |
| | Consistency | Buttery |
| Growth temperature test (° C.) | 4 | − |
| | 37 | + |
| | 42 | + w |
| | 45 | − |
| Catalase reaction | | + |
| Oxidase reaction | | + |
| Acid and/or gas production from glucose | | −/− |
| Oxidation/fermentation (O/F) test | | −/− |
| Lipase activity (Tween 80) | | − |
| Biochemical tests | Nitrate reduction | + |
| | Indole production | − |
| | Glucose acidification | − |
| | Arginine dihydrolase | − |
| | Urease | − |
| | Esculin hydrolysis | − |
| | Gelatin hydrolysis | − |
| | β-Galactosidase | − |
| | Cytochrome oxidase | + |
| Assimilation tests | Glucose | − |
| | L-Arabinose | − |
| | D-Mannose | − |
| | D-Mannitol | − |
| | N-Acetyl-D-glucosamine | − |
| | Maltose | − |
| | Potassium gluconate | + |
| | n-Capric acid | − |
| | Adipic acid | + |
| | dl-Malic acid | + |
| | Sodium citrate | − |
| | Phenyl acetate | − |

Production of HMGR Derived from *Comamonas* sp. 25-MV (FERM BP-11066)

27 U of purified HMGR was obtained from above-described *Comamonas* sp. 25-MV (FERM BP-11066) by the same technique as described in Example 1 except that Medium A was replaced with Medium C.

Example 5

Expression in *Escherichia coli* and purification of HMGR derived from *Pseudomonas* sp. 1-MV (FERM BP-11063)

PCR was performed using chromosomal DNA of *Pseudomonas* sp. 1-MV (FERM BP-11063) in Example 1 as a template and primers having sequences of SEQ ID NOS: 14 and 15 to obtain a DNA fragment including the HMGR gene (SEQ ID NO: 12). A fragment obtained by digesting the obtained DNA fragment with XbaI and SacI was ligated to a fragment obtained by similarly digesting plasmid pPOW1 with XbaI and SacI, wherein the plasmid pPOW1 was obtained by replacing the region of HindIII site to the EcoI site in the multicloning site of plasmid pHSG398 with a DNA fragment (SEQ ID NO: 24) including a POP promoter sequence. The obtained plasmid pPOW1-HMGRps was introduced into the *Escherichia coli* W3110 strain to obtain HMGR-producing recombinant bacteria. These bacteria were cultured in 1.6 L of a medium containing 3% yeast extract, 4.5% sorbitol, 0.1% Antifoam 028, and 30 µg/mL chloramphenicol at 30° C. for two days while controlling pH of the culture so that the lowest pH should be 7.2. After bacterial cells were obtained from the culture broth by centrifugation, the bacterial cells were suspended in 10 mM Tris hydrochloride buffer (pH 7.5) and 5 mM EDTA. Then, lysozyme was added, and the suspension was treated at 37° C. for 30 minutes to disrupt bacterial cells and centrifuged to remove insoluble matters to obtain a crude enzyme solution.

The obtained crude enzyme solution was adsorbed to Q Sepharose Big Beads Column (45.5×510 mm) equilibrated with 10 mM Tris hydrochloride buffer (pH 8.5) and eluted with 10 mM Tris hydrochloride buffer (pH 8.5), 0.1 M NaCl and 0.1% Tween 80 to collect a fraction having HMGR activity. Ammonium sulfate was added to the obtained fraction at 37.5%, the precipitates were collected by centrifugation and then dissolved in 10 mM Tris hydrochloride buffer (pH 8.5), and the solution was dialyzed against 10 mM Tris hydrochloride buffer (pH 8.5) and 5% glycerol. The dialyzed solution containing HMGR was adsorbed to DEAE Sepharose FF Column (22.5×210 mm) equilibrated with 10 mM Tris hydrochloride buffer (pH 8.5) and 5% glycerol and eluted with NaCl at a gradient of 0→0.25 M to collect a fraction having HMGR activity. Ammonium sulfate was added to the obtained fraction at 20%, and the fraction was adsorbed to Phenyl Sepharose FF Column (22.5×410 mm) equilibrated with 20% ammonium sulfate, 10 mM Tris hydrochloride buffer (pH 7.5), and 5% glycerol and eluted at gradients of 20% ammonium sulfate and 0% Tween 80→0% ammonium sulfate and 0.1% Tween 80 to collect a fraction having HMGR activity. The obtained fraction was dialyzed against 10 mM bis Tris hydrochloride buffer (pH 6.0) and 5% glycerol, then adsorbed to Blue Sepharose CL6B Column (45.5×310 mm) equilibrated with 10 mM bis Tris hydrochloride buffer (pH 6.0) and 5% glycerol, and eluted at a gradient of 0 M NaCl and 0% Tween 80→2.5 M NaCl and 0.1% Tween 80 to collect a fraction having HMGR activity. The obtained fraction was dialyzed against 10 mM bis Tris hydrochloride buffer (pH 6.0) and 5% glycerol, then adsorbed to a hydroxyapatite column (25.5×210 mm) equilibrated with 10 mM bis Tris hydrochloride buffer (pH 6.0), 5% glycerol, and 0.1% Tween 80, and eluted at a gradient of 10 mM bis Tris hydrochloride buffer (pH 6.0) →80 mM potassium phosphate buffer (pH 6.0) to collect a fraction having HMGR activity. The fraction was concentrated by ultrafiltration with a membrane having a molecular weight cut off of 10,000 to obtain 13 kU of purified HMGR.

Example 6

Expression of HMGR derived from *Pseudomonas mevalonii* (J Bacteriol. 1989 June; 171(6): 2994-3001) in *Escherichia coli*

A DNA fragment was chemically synthesized in which a XbaI site is linked to the 5' end and a SacI site is linked to the 3' end of the HMGR gene (SEQ ID NO: 13) of *Pseudomonas mevalonii*. A fragment obtained by digesting this DNA fragment with XbaI and SacI was ligated to a fragment obtained by similarly digesting plasmid pPOW1 with XbaI and SacI. The obtained plasmid pPOW1-HMGRpm was introduced into the *Escherichia coli* W3110 strain to obtain HMGR-producing recombinant bacteria. This bacteria were inoculated in 160 mL of a medium (pH 7.5) containing 3% yeast extract, 0.3% sorbitol, and 30 µg/mL chloramphenicol and cultured at 37° C. for one day.

Approximately 0.2 U/mL of HMGR activity per milliliter of the culture broth was confirmed.

Example 7

Expression in *Escherichia coli* and purification of HMGR derived from *Archaeoglobus fulgidus* (NBRC100126) (Protein Sci. 2000 June; 9(6): 1226-34)

PCR was performed using chromosomal DNA of *Archaeoglobus fulgidus* (NBRC100126) as a template and primers having sequences of SEQ ID NOS: 16 and 17 to obtain a DNA fragment including the HMGR gene. A fragment obtained by digesting the obtained DNA fragment with XbaI and SacI was ligated to a fragment obtained by similarly digesting plasmid pPOW1 with XbaI and SacI. The obtained plasmid pPOW1-HMGRaf was introduced into the *Escherichia coli* W3110 strain to obtain HMGR-producing recombinant bacteria.

The obtained bacteria were inoculated in five flasks each containing 160 mL of a medium (pH 7.5) containing 3% yeast extract, 0.3% sorbitol, and 30 μg/mL chloramphenicol and cultured at 37° C. for two days. Bacterial cells were obtained from the culture broth by centrifugation and then suspended in 10 mM Tris hydrochloride buffer (pH 7.5). Then, the bacterial cells were disrupted by ultrasonication, and insoluble matters were removed by centrifugation to obtain a crude enzyme solution containing 315 U of HMGR. The obtained crude enzyme solution was subjected to heat treatment at 80° C. for 30 minutes, then insoluble matters were removed by centrifugation, and the solution was adsorbed to DEAE Sepharose FF Column (14.5×90 mm) equilibrated with 10 mM Tris hydrochloride buffer (pH 8.5) and eluted with NaCl at a gradient of 0→0.5 M to collect a fraction having HMGR activity. Ammonium sulfate was added to the obtained fraction at 15%, and the fraction was adsorbed to Phenyl Sepharose FF Column (14.5×35 mm) equilibrated with 15% ammonium sulfate and 10 mM Tris hydrochloride buffer (pH 7.5) and eluted at gradients of 15% ammonium sulfate, 0% glycerol, and 0% Tween 80→0% ammonium sulfate, 5% glycerol, and 0.1% Tween 80 to collect a fraction having HMGR activity. The fraction was concentrated by ultrafiltration with a membrane having a molecular weight cut off of 10,000 to obtain 17 U of purified HMGR.

Example 8

Expression in *Escherichia coli* and purification of MVK derived from *Saccharomyces cerevisiae* (NBRC1136)

Using chromosomal DNA of *Saccharomyces cerevisiae* (NBRC1136) as a template, PCR was performed with primers having sequences of SEQ ID NOS: 18 and 19 to obtain a DNA fragment corresponding to the first half of the MVK gene and with primers having sequences of SEQ ID NOS: 20 and 21 to obtain a DNA fragment corresponding to the last half of the MVK gene. PCR was performed using these obtained DNA fragments corresponding to the first half and the last half as templates and primers having sequences of SEQ ID NOS: 18 and 21 to obtain a DNA fragment including the full-length MVK gene. The MVK gene in the obtained DNA fragment had a sequence of SEQ ID NO: 5 in which A was replaced with T in the 819th position, but the translated amino acid sequence was unchanged. A fragment obtained by digesting the obtained DNA fragment including the full-length MVK gene with XbaI and SacI was ligated to a fragment obtained by similarly digesting plasmid pPOW1 with XbaI and SacI. The obtained plasmid pPOW1-MVK was introduced into the *Escherichia coli* W3110 strain to obtain MVK-producing recombinant bacteria.

The obtained bacteria were inoculated in three flasks each containing 160 mL of a medium (pH 8.0) containing 3% yeast extract, 0.3% sorbitol, and 30 μg/mL chloramphenicol and cultured at 25° C. for three days. Bacterial cells were obtained from the culture broth by centrifugation and then suspended in 10 mM Tris hydrochloride buffer (pH 7.5). Then, the bacterial cells were disrupted by ultrasonication, and insoluble matters were removed by centrifugation to obtain a crude enzyme solution containing 5660 U of MVK. The obtained crude enzyme solution was adsorbed to DEAE Sepharose FF Column (14.5×90 mm) equilibrated with 10 mM Tris hydrochloride buffer (pH 7.5) and eluted with NaCl at a gradient of 0→0.5 M to collect a fraction having MVK activity. Ammonium sulfate was added to the obtained fraction at 15%, and the fraction was adsorbed to HiTrap Phenyl FF (highsub) Column (5 mL) equilibrated with 15% ammonium sulfate and 10 mM Tris hydrochloride buffer (pH 7.5) and eluted at a gradient of 15% of ammonium sulfate→0% ammonium sulfate to collect a fraction having MVK activity. The fraction was concentrated by ultrafiltration with a membrane having a molecular weight cut off of 10,000 to obtain 3304 U of purified MVK.

Method for Measuring MVK Activity 0.5 mL of Reagent C was poured into a test tube and preliminarily heated at 37° C. for five minutes, and then 0.01 mL of enzyme solution was added to bring about a reaction at 37° C. for five minutes. After completion of the reaction, 1 mL of 0.1N HCl was added to terminate the reaction, and absorbance (Aa) at a wavelength of 550 nm was measured. The same procedure was performed using Reagent Cb to measure absorbance (Ab) as a blank. From the difference between these absorbances (Aa-Ab), 1 U of enzyme activity per milliliter of an enzyme solution was calculated as U/mL=1.589×(Aa-Ab). It should be noted that one unit of enzyme activity was defined as the amount of an enzyme required to produce one micromole of NADH at 37° C. per minute, and the enzyme solution was diluted with an enzyme dilution buffer (10 mM Tris hydrochloride buffer [pH 7.5], 0.1% BSA) for measurement as required.

Example 9

Expression in *Escherichia coli* and purification of HMGL derived from *Pseudomonas putida* KT2440 (ATCC47054)

PCR was performed using chromosomal DNA of *Pseudomonas putida* KT2440 (ATCC47054) as a template and primers having sequences of SEQ ID NOS: 22 and 23 to obtain a DNA fragment including the HMGL gene. A fragment obtained by digesting the obtained DNA fragment with XbaI and SacI was ligated to a fragment obtained by similarly digesting plasmid pPOW1 with XbaI and SacI. The obtained plasmid pPOW1-HMGL was introduced into the *Escherichia coli* W3110 strain to obtain HMGL-producing recombinant bacteria.

The obtained bacteria were cultured in 1.6 L of a medium containing 3% yeast extract, 4.5% sorbitol, 0.1% Antifoam 028, and 30 μg/mL chloramphenicol at 30° C. for two days, while controlling pH in the culture so that the lowest pH should be 7.0 to obtain a culture broth having 35.7 U/mL HMGL activity. The bacteria were also cultured in 1.6 L of a medium having the same composition at 30° C. for two days while controlling pH in the culture so that the lowest pH should be 6.5 to obtain a culture broth having 36.7 U/mL HMGL activity. These culture broths were centrifuged together to obtain bacterial cells and then suspended in 10 mM Tris hydrochloride buffer (pH 7.5). Then, bacterial cells were disrupted by ultrasonication, and insoluble matters were removed by centrifugation to obtain a crude enzyme solution containing HMGL. The obtained crude enzyme solution was adsorbed to Q Sepharose Big Beads Column (45.5×510 mm) equilibrated with 10 mM Tris hydrochloride buffer (pH 7.5), the column was washed with 10 mM Tris hydrochloride buffer (pH 7.5) and 0.1 M NaCl, the solution was eluted with 10 mM Tris hydrochloride buffer (pH 8.5) and 0.3 M NaCl to collect a fraction having HMGL activity. Ammonium sulfate was added to the fraction at 37.5%, precipitates were collected by centrifugation and dissolved in 10 mM Tris hydrochloride buffer (pH 8.5), and the solution was dialyzed against 10 mM Tris hydrochloride buffer (pH 8.5). The dialyzed solution containing HMGL was adsorbed to DEAE Sepharose FF Column (22.5×210 mm) equilibrated with 10 mM Tris hydrochloride buffer (pH 8.5) and 5% glycerol and eluted with NaCl at a gradient of 0→0.5 M to collect a fraction having HMGL activity. Ammonium sulfate was added to this fraction at 15%, and the fraction was adsorbed to Phenyl Sepharose FF Column (22.5×100 mm) equilibrated with 15% ammonium sulfate and 10 mM Tris hydrochloride buffer (pH 7.5) and eluted at gradients of 15% ammonium sulfate and 0% ethylene glycol→0% ammonium sulfate and 10% ethylene glycol to collect a fraction having HMGL activity. The obtained fraction was dialyzed against 10 mM Tris hydrochloride buffer (pH 7.5), and the fraction was concentrated by ultrafiltration with a membrane having a molecular weight cut off of 10,000 to obtain 20 kU of purified HMGL.

Method for Measuring HMGL Activity 0.070 mL of Reagent D1 and 0.006 mL of an enzyme solution were placed in a cell and incubated at 37° C. for five minutes, then 0.020 mL of Reagent D2 was added. The mixture was reacted at 37° C. for five minutes, and the absorbance rate (Aa) per minute was measured from the part where absorbance at a wavelength of 340 nm after the addition of Reagent D2 was linearly decreased. The same procedure was further performed as a blank using an enzyme dilution buffer (10 mM Tris hydrochloride buffer [pH 9]) instead of an enzyme solution to measure the absorbance decreasing rate (Ab) per minute. From the difference between these absorbance decreasing rates (Aa-Ab), one unit of enzyme activity per milliliter of an enzyme solution was calculated as U/mL=2.54×(Aa-Ab). It should be noted that one unit of enzyme activity was defined as the amount of an enzyme required to decrease one micromole of NADH at 37° C. per minute, and the enzyme solution was diluted with the enzyme dilution buffer as required. Measurement was performed using Automated Analyzer BM9020 (JEOL Ltd.).

Example 10

Measurement of MVA and HMG-CoA by enzyme cycling method using HMGR derived from *Pseudomonas* sp. 1-MV (FERM BP-11063) that was expressed in *Escherichia coli*

135 µL of any of Reagents E1 to E5 as a first measuring reagent was added to 15 µl, of a sample solution (distilled water, 10, 50, or 100 nM MVA or 10, 50, or 100 nM HMG-CoA) at 37° C., 15 µL of Reagent E11 or E12 as a second measuring reagent was added five minutes later, and then changes in absorbance [mABS] at a wavelength of 410 nm at 37° C. over five minutes were measured. Measurement was performed using Automated Analyzer BM9020 (JEOL Ltd.). The results are shown in Table 5. It is shown that both MVA and HMG-CoA in a sample solution can be quantified at least in the range of 10 to 100 nM in the presence of CoA. As an enzyme cycling reaction did not occur in the absence of CoA, it is shown that the enzyme cycling reactions represented by Reaction Formulas 15 and 16 did not occur, and that the enzyme cycling reactions represented by Reaction Formulas 17 and 18 did not occur either. In the presence of HMGL, an enzyme cycling reaction did not occur even in the presence of CoA when a sample contains MVA. Therefore, it is shown that the enzyme cycling reactions represented by Reaction Formulas 15 and 16 did not occur, and that the enzyme cycling reactions that occurred are multistep reactions represented by Reaction Formulas 19 and 20 in an enzyme cycling method. In the presence of MVK, an enzyme cycling reaction did not occur even in the presence of CoA when the sample contains HMG-CoA. Therefore, it is shown that the enzyme cycling reactions represented by Reaction Formulas 17 and 18 did not occur, and that the enzyme cycling reactions that occurred are multistep reactions represented by Reaction Formulas 19 and 20 in an enzyme cycling method. Furthermore, when Reagent E3 was used as the first measuring reagent, absorbance of a sample of distilled water was increased as compared with when Reagent E2 was used, and the increase was inhibited when Reagent E4 was used. From these results, it is suggested that MVA is present in ATP.

TABLE 5

| Reagent | | Sample solution | | | | | | |
|---|---|---|---|---|---|---|---|---|
| First measuring reagent | Second measuring reagent | | MVA | | | HMGCoA | | |
| | | DW | 10 nM | 50 nM | 100 nM | 10 nM | 50 nM | 100 nM |
| E1 | E11 + HMGR | 1.2 | 1.1 | 1.2 | 1.1 | 0.6 | 1.1 | 10 |
| E1 | E12 | 0.8 | 0.8 | 0.8 | 0.8 | 0.8 | 0.6 | 0.8 |
| E2 + CoA | E11 + HMGR | 5.0 | 14.4 | 50.0 | 97.2 | 9.7 | 26.4 | 42.0 |
| E2 + CoA | E12 | 0.7 | 0.7 | 0.7 | 0.8 | 0.7 | 0.7 | 0.6 |
| E3 + CoA + ATP + Mg | E11 + HMGR | 26.3 | 35.3 | 68.9 | 112.8 | 30.8 | 45.9 | 60.1 |
| E3 + CoA + ATP + Mg | E12 | 0.6 | 0.8 | 0.8 | 0.7 | 0.8 | 0.8 | 0.8 |
| E4 + CoA + ATP + Mg + MVK | E11 + HMGR | 1.6 | 1.4 | 1.7 | 2.0 | 1.7 | 2.3 | 3.0 |
| E4 + CoA + ATP + Mg + MVK | E12 | 0.9 | 1.0 | 0.9 | 0.8 | 0.6 | 0.8 | 0.9 |
| E5 + CoA + HMGL | E11 + HMGR | 1.9 | 1.9 | 1.8 | 2.0 | 1.7 | 1.5 | 1.8 |
| E5 + CoA + HMGL | E12 | 1.2 | 1.5 | 1.3 | 1.1 | 1.3 | 1.1 | 1.3 |

Example 11

Measurement of MVA by enzyme cycling method using HMGR Derived from *Pseudomonas* sp. 1-MV (FERM BP-11063) that was expressed in *Escherichia Coli*

180 μL of Reagent F1 was added to 201 μL of a sample solution (in which MVA was dissolved in distilled water or Control Serum Consera N [Nissui Pharmaceutical Co., Ltd.] to obtain 0, 0.25, 0.5, 1, 2.5, 5, 10, 25, or 50 nM), and the mixture was let stand at 37° C. for five minutes. Then, 20 μL of Reagent F2 was added, and then changes in absorbance at a wavelength of 405 nm over 17 minutes were measured. Measurement was performed in quadruplicate using Automated Analyzer 7170S (Hitachi, Ltd.). The results are shown in Tables 6 and 7. The measurement limit of MVA is shown to be 0.5 nM in Table 6 and 0.25 nM in Table 7.

TABLE 6

| in DW MVA[nM] | [mABS] ΔA405 | AV | SD | in DW MVA[nM] | [mABS] ΔA405 | AV | SD | in DW MVA[nM] | [mABS] ΔA405 | AV | SD |
|---|---|---|---|---|---|---|---|---|---|---|---|
| 0 | 10.3 | 10.30 | 0.00 | 1 | 13.0 | 13.08 | 0.05 | 10 | 46.8 | 46.53 | 0.25 |
|   | 10.3 |   |   |   | 13.1 |   |   |   | 46.5 |   |   |
|   | 10.3 |   |   |   | 13.1 |   |   |   | 46.6 |   |   |
|   | 10.3 |   |   |   | 13.1 |   |   |   | 46.2 |   |   |
| 0.25 | 11.0 | 10.68 | 0.34 | 2.5 | 18.7 | 18.75 | 0.17 | 25 | 99.3 | 99.50 | 0.42 |
|   | 10.7 |   |   |   | 18.7 |   |   |   | 99.8 |   |   |
|   | 10.8 |   |   |   | 19.0 |   |   |   | 99.9 |   |   |
|   | 10.2 |   |   |   | 18.6 |   |   |   | 99 |   |   |
| 0.5 | 11.2 | 11.25 | 0.13 | 5 | 27.8 | 27.95 | 0.19 | 50 | 182.9 | 184.55 | 1.27 |
|   | 11.3 |   |   |   | 28.2 |   |   |   | 184.2 |   |   |
|   | 11.1 |   |   |   | 28.0 |   |   |   | 185.5 |   |   |
|   | 11.4 |   |   |   | 27.8 |   |   |   | 185.6 |   |   |

TABLE 7

| in consera MVA[nM] | [mABS] ΔA405 | AV | SD | in consera MVA[nM] | [mABS] ΔA405 | AV | SD | in consera MVA[nM] | [mABS] ΔA405 | AV | SD |
|---|---|---|---|---|---|---|---|---|---|---|---|
| 0 | 15.1 | 15.20 | 0.14 | 1 | 18.8 | 18.90 | 0.27 | 10 | 49.8 | 49.50 | 0.29 |
|   | 15.2 |   |   |   | 18.7 |   |   |   | 49.6 |   |   |
|   | 15.1 |   |   |   | 19.3 |   |   |   | 49.1 |   |   |
|   | 15.4 |   |   |   | 18.8 |   |   |   | 49.5 |   |   |
| 0.25 | 16.1 | 16.23 | 0.19 | 2.5 | 23.7 | 23.93 | 0.26 | 25 | 95.6 | 95.78 | 0.43 |
|   | 16.2 |   |   |   | 23.7 |   |   |   | 95.9 |   |   |
|   | 16.1 |   |   |   | 24.2 |   |   |   | 95.3 |   |   |
|   | 16.5 |   |   |   | 24.1 |   |   |   | 96.3 |   |   |
| 0.5 | 17.7 | 17.33 | 0.38 | 5 | 31.5 | 32.25 | 0.76 | 50 | 167.2 | 167.30 | 0.26 |
|   | 17.4 |   |   |   | 31.7 |   |   |   | 167.6 |   |   |
|   | 16.8 |   |   |   | 32.8 |   |   |   | 167.0 |   |   |
|   | 17.4 |   |   |   | 33.0 |   |   |   | 167.4 |   |   |

Example 12

Measurement of CoA by enzyme cycling method using HMGR derived from *Pseudomonas* sp. 1-MV (FERM BP-11063) that was expressed in *Escherichia coli*

135 μl of Reagent G1 was added to 15 μL of a sample solution (distilled water, 100 or 1000 nM CoA), and the mixture was incubated for five minutes. Then, 15 μL of MVA solution (0, 0.0005, 0.005, or 0.05 mM) was added, and changes in absorbance [mABS] at a wavelength of 410 nm over 26 minutes were measured. The results are shown in Table 8.

TABLE 8

| MVA SOLUTION | CoA Sample 0 nM | 100 nM | 1000 nM |
|---|---|---|---|
| 0.05 mM | 39.13 | 51.14 | 145.65 |
| 0.005 mM | 8.39 | 9.27 | 18.13 |
| 0.0005 mM | 5.33 | 5.1 | 5.98 |
| 0 mM | 4.98 | 4.1 | 4.51 |

Similarly, 135 μL of Reagent G1 was added to 15 μL of a sample solution (distilled water, 10, 20, 50, 100, or 200 nM CoA), and the mixture was incubated for five minutes. Then, 15 μL of MVA solution (0.5, 2.5, or 5 mM) was added, and changes in absorbance [mABS] at a wavelength of 410 nm over five minutes were measured. The results are shown in Table 9.

TABLE 9

| MVA SOLUTION | CoA Sample 0 nM | 10 nM | 20 nM | 50 nM | 100 nM | 200 nM |
|---|---|---|---|---|---|---|
| 0.5 mM | 63.44 | 72.45 | 73.68 | 78.64 | 86.68 | 102.81 |
| 2.5 mM | 178.89 | 184.18 | 186.28 | 194.82 | 207.40 | 231.64 |
| 5 mM | 287.91 | 291.88 | 295.75 | 304.31 | 317.0 | 341.95 |

Furthermore, 135 μL of Reagent G2 was similarly added to a sample solution (distilled water, 5, 10, 20, 50, or 100 nM CoA), and the mixture was incubated for five minutes. Then, 15 μL of MVA solution (2.5 mM) was added, and changes in absorbance [mABS] at a wavelength of 410 nm over five minutes were measured in quadruplicate. The results are shown in Table 10.

TABLE 10

| sample | 0 nM CoA | | | | 5 nM CoA | | | | 10 nM CoA | | | |
|---|---|---|---|---|---|---|---|---|---|---|---|---|
| [mABS] | 420.63 | 419.32 | 417.68 | 420.68 | 422.13 | 421.90 | 421.88 | 422.68 | 424.33 | 427.64 | 427.28 | 424.70 |
| average | 419.58 | | | | 422.15 | | | | 425.99 | | | |
| SD | 1.41 | | | | 0.37 | | | | 1.71 | | | |

| sample | 20 nM CoA | | | | 50 nM CoA | | | | 100 nM CoA | | | |
|---|---|---|---|---|---|---|---|---|---|---|---|---|
| [mABS] | 429.85 | 429.57 | 425.47 | 425.67 | 435.66 | 435.89 | 437.34 | 436.87 | 452.31 | 453.23 | 453.92 | 452.07 |
| average | 427.64 | | | | 436.44 | | | | 452.88 | | | |
| SD | 2.39 | | | | 0.80 | | | | 0.85 | | | |

It is shown that the CoA concentration of the minimum detection limit is at least 50 nM or lower. Measurement was performed using Automated Analyzer BM9020 (JEOL Ltd.).

Example 13

Measurement of MVA and HMG-CoA by enzyme cycling method using HMGR derived from *Pseudomonas* sp. 1-MV (FERM BP-11063) that was expressed in *Escherichia coli* after treatment of sample using Mvk derived from *Saccharomyces cerevisiae* (NBRC1136) that was expressed in *Escherichia coli*

100 μL of Reagent H1 or H2 was added to 100 μL of a sample solution (distilled water, 250 nM MVA, or 750 nM HMG-CoA), and the mixture was incubated at 37° C. for five minutes. Then, 1) MVK was removed by ultrafiltration with a membrane having a molecular weight cut off of 10,000, or 2) 1 μL of 100 mM EDTA solution was added to terminate the reaction catalyzed by MVK. Then, 180 μL of Reagent F1 was added to 20 μL of the sample of 1) or 2), and the mixture was let stand at 37° C. for five minutes. 20 μL of Reagent F2 was added, and then changes in absorbance [mABS] at a wavelength of 405 nm over five minutes were measured. The measurement after the filtration with a membrane or the addition of EDTA was performed using Automated Analyzer 7170S (Hitachi, Ltd.). The results are shown in Table 11. It is shown that treatment with MVK removed MVA from the sample, and that treatment with MVK does not affect the measurement of HMG-CoA.

TABLE 11

| | | sample 1 | sample 2 | sample 3 |
|---|---|---|---|---|
| MVA | [nM] | 0 | 250 | 0 |
| HMGCoA | [nM] | 0 | 0 | 750 |
| 1) | Reagent G1 | 8.3 | 126.2 | 311.5 |
| membrane | Reagent G2 | 6.3 | 5.9 | 319.5 |
| 2) | Reagent G1 | 4.6 | 119.4 | 341.2 |
| +EDTA | Reagent G2 | 2.6 | 3.2 | 356.0 |

Example 14

Measurement of HMG-CoA by enzyme cycling method using HMGR derived from *Pseudomonas* sp. 1-MV (FERN BP-11063) that was expressed in *Escherichia coli* and MVK derived from *Saccharomyces cerevisiae* that was expressed in *Escherichia coli* (NBRC1136) (alkali treatment)

80 μL of Reagent J1 (+) or J1 (−) was added to 16 μL of a sample solution (distilled water, 10, 50, or 100 nM MVA, or 10, 50, or 100 nM HMG-CoA) at 37° C., and the mixture was incubated for 1.7 minutes. Then, 24 μL of Reagent J2 was added, the mixture was further incubated for 3.3 minutes, then 40 μL of reagent J3 was added, and the mixture was further incubated for 3.8 minutes. Then, 16 μL of Reagent J4 was added, and then changes in absorbance [mABS] at a wavelength of 410 nm over 22.0 minutes were measured. Measurement was performed using Automated Analyzer BM9020 (JEOL Ltd.). The results are shown in Table 12. It is shown that approximately 99% of MVA in the sample was removed by treatment with MVK in 1.7 minutes. Furthermore, it is also shown that measured values of HMG-CoA in the sample are not affected by treatment with MVK. Furthermore, it is also shown that MVA contaminated in Reagent J1 (+) was removed by treatment with MVK.

TABLE 12

| | Sample | | | | | | |
|---|---|---|---|---|---|---|---|
| | | MVA | | | HMGCoA | | |
| Reagent | DW | 10 nM | 50 nM | 100 nM | 10 nM | 50 nM | 100 nM |
| J1(+), J2, J3, J4 | 16.55 | 16.76 | 17.31 | 18.37 | 23.39 | 50.48 | 85.16 |
| J1(−), J2, J3, J4 | 65.43 | 85.15 | 160.91 | 246.04 | 71.20 | 97.74 | 130.10 |

Example 15

Measurement of HMG-CoA by enzyme cycling method using HMGR derived from *Pseudomonas* sp. 1-MV (FERM BP-11063) that was expressed in *Escherichia coli* and MVK derived from *Saccharomyces cerevisiae* (NBRC1136) that was expressed in *Escherichia coli* (EDTA treatment)

80 μL of Reagent K1 (+) or K1 (−) was added to 16 μL of a sample solution (aqueous solution of MVA and HMG-CoA with concentrations shown in Table 13) at 37° C., and the mixture was incubated for 1.7 minutes. Then, 24 μL of Reagent K2 was added, and the mixture was further incubated for 3.3 minutes. Then, 40 μL of Reagent K3 was added, and the mixture was further incubated for 3.8 minutes. Then, 16 μL of Reagent K4 (+) or K4 (−) was added, and changes in absorbance [mABS] at a wavelength of 410 nm over 22.0 minutes were measured. Measurement was performed using Automated Analyzer BM9020 (JEOL Ltd.). Combinations of reagents used for measurement and the results are shown in Table 13.

TABLE 13

| Reagent | sample 1 0 nM 0 nM | sample 2 5 nM 0 nM | sample 3 10 nM 0 nM | sample 4 25 nM 0 nM | sample 5 50 nM 0 nM | sample 6 0 nM 5 nM | sample 7 0 nM 10 nM | sample 8 0 nM 25 nM | sample 9 0 nM MVA 50 nM HMGCoA |
|---|---|---|---|---|---|---|---|---|---|
| K1(+), K2, K3, K4(+) | 25.63 | 25.81 | 25.47 | 25.42 | 26.38 | 31.60 | 37.41 | 54.82 | 83.59 |
| K1(−), K2, K3, K4(−) | 27.81 | 37.50 | 47.71 | 77.41 | 124.14 | 33.55 | 40.00 | 56.73 | 84.57 |

Similarly, the above-described measurement was performed for solutions obtained by adding the sample solution to control serum so that the concentrations of MVA and HMG-CoA should be concentrations shown in Table 14. The results are shown in Table 14.

TABLE 14

| Reagent | sample 1 0 nM 0 nM | sample 2 5 nM 5 nM | sample 3 10 nM 10 nM | sample 4 25 nM 25 nM | sample 5 50 nM 50 nM | sample 6 50 nM 100 nM | sample 7 50 nM MVA 250 nM HMGCoA |
|---|---|---|---|---|---|---|---|
| K1(+), K2, K3, K4(+) | 24.22 | 24.75 | 26.75 | 31.38 | 39.55 | 56.21 | 107.52 |
| K1(−), K2, K3, K4(−) | 29.61 | 37.54 | 47.20 | 74.46 | 120.27 | 135.24 | 181.37 |

It is shown that up to 50 nM MVA present in the sample was removed, with less than 1% remaining. Furthermore, it is shown that treatment with MVK does not affect measurement of HMG-CoA.

Example 16

Measurement of MVA by enzyme cycling method using HMGR derived from *Pseudomonas* sp. 1-MV (FERM BP-11063) that was expressed in *Escherichia coli* and HMGL derived from *Pseudomonas putida* KT2440 (ATCC47054) that was expressed in *Escherichia coli* (membrane filtration)

70 μL of Reagent L1 or L2 was added to 70 μL each of Sample Solutions 1 to 6 shown in Table 15, and the mixture was incubated at 37° C. for five minutes. Then, HMGL was removed by ultrafiltration with a membrane having a molecular weight cut off of 10,000. Then, 180 of Reagent F1 was added to 20 μL of a filtered sample, the mixture was let stand at 37° C. for five minutes, 20 μL of Reagent F2 was added, and then changes in absorbance [mABS] at a wavelength of 405 nm over five minutes were determined. After the filtration with a membrane, measurement was performed using Automated Analyzer 7170S (Hitachi, Ltd.). The results are shown in Table 16. It is shown that treatment with HMGL removed HMG-CoA from the sample. Furthermore, it is shown that treatment with HMGL does not affect measurement of MVA.

TABLE 15

| | sample 1 | sample 2 | sample 3 | sample 4 | sample 5 | sample 6 |
|---|---|---|---|---|---|---|
| MVA | 50 nM | 50 nM | 50 nM | 0 nM | 0 nM | 0 nM |
| HMGCoA | 0 nM | 250 nM | 750 nM | 0 nM | 250 nM | 750 nM |

TABLE 16

| | sample 1 | sample 2 | sample 3 | sample 4 | sample 5 | sample 6 |
|---|---|---|---|---|---|---|
| Reagent L1 | 136.7 | 136.0 | 132.8 | 19.1 | 20.1 | 20.2 |
| Reagent L2 | 135.9 | 407.3 | 769.4 | 20.3 | 336.6 | 706.6 |

Example 17

Measurement of MVA by enzyme cycling method using HMGR derived from *Pseudomonas* sp. 1-MV (FERM BP-11063) that was expressed in *Escherichia coli* and HMGL derived from *Pseudomonas putida* KT2440 (ATCC47054) that was expressed in *Escherichia coli* (alkali treatment)

80 μL of Reagent M1 (+) or M1 (−) was added to 16 μL of a sample solution (aqueous solution of MVA or HMG-CoA at concentrations shown in Table 17) at 37° C., and the mixture was incubated for 1.7 minutes. Then, 24 μL of Reagent M2 was added, and the mixture was further incubated for 3.3 minutes, then 40 μL of Reagent M3 was added, and the mixture was further incubated for 3.8 minutes. Then, 16 μL of Reagent M4 was further added, and then changes in absorbance [mABS] at a wavelength of 410 nm over 22.0 minutes were measured. Measurement was performed using Automated Analyzer BM9020 (JEOL Ltd.). Combinations of reagents used for measurement and the results are shown in Table 17.

TABLE 17

| Reagent | sample 1<br>0 nM<br>0 nM | sample 2<br>5 nM<br>0 nM | sample 3<br>10 nM<br>0 nM | sample 4<br>25 nM<br>0 nM | sample 5<br>50 nM<br>0 nM | sample 6<br>0 nM<br>5 nM | sample 7<br>0 nM<br>10 nM | sample 8<br>0 nM<br>25 nM | sample 9<br>0 nM MVA<br>50 nM HMGCoA |
|---|---|---|---|---|---|---|---|---|---|
| M1(+), M2, M3, M4 | 21.94 | 30.47 | 40.59 | 64.50 | 108.38 | 24.28 | 23.65 | 24.71 | 24.87 |
| M1(−), M2, M3, M4 | 21.78 | 30.58 | 39.89 | 66.53 | 107.73 | 27.53 | 31.69 | 43.47 | 62.41 |

Similarly, solutions prepared by adding MVA and HMG-CoA to Control Serum Consera N (Nissui Pharmaceutical Co., Ltd.) at concentrations shown in Tables 18 and 19 were used as sample solutions to perform the above-described measurement. The results are shown in Tables 18 and 19.

TABLE 18

| Reagent | sample 1<br>0 nM<br>0 nM | sample 2<br>0 nM<br>5 nM | sample 3<br>0 nM<br>10 nM | sample 4<br>0 nM<br>25 nM | sample 5<br>0 nM<br>50 nM | sample 6<br>0 nM<br>100 nM | sample 7<br>0 nM MVA<br>250 nM HMGCoA |
|---|---|---|---|---|---|---|---|
| M1(+), M2, M3, M4 | 22.66 | 22.76 | 22.75 | 22.18 | 22.26 | 22.65 | 23.53 |
| M1(−), M2, M3, M4 | 22.09 | 22.68 | 23.73 | 25.93 | 29.99 | 39.29 | 62.20 |

TABLE 19

| Reagent | sample 1<br>0 nM<br>0 nM | sample 2<br>5 nM<br>5 nM | sample 3<br>10 nM<br>10 nM | sample 4<br>25 nM<br>25 nM | sample 5<br>50 nM<br>50 nM | sample 6<br>50 nM<br>100 nM | sample 7<br>50 nM MVA<br>250 nM HMGCoA |
|---|---|---|---|---|---|---|---|
| M1(+), M2, M3, M4 | 22.66 | 28.18 | 34.78 | 53.46 | 83.90 | 82.72 | 83.21 |
| M1(−), M2, M3, M4 | 22.09 | 27.73 | 35.30 | 55.70 | 88.77 | 98.06 | 120.26 |

It is shown that up to 250 nM HMG-CoA present in samples was removed, with lower than 4% remaining. It is also shown that up to 100 nM HMG-CoA was removed, with lower than 1% remaining. Furthermore, it is shown that treatment with HMGL does not affect measurement of MVA.

Example 18

Production of enzyme cycling reagent for measuring MVA and/or HMG-CoA, comprising step of removing contaminated MVA using MVK derived from *Saccharomyces cerevisiae* (NBRC1136) that was expressed in *Escherichia coli* (EDTA addition)

10 mL each of: Reagent N2 prepared by adding 1 mM ATP and 1 mM magnesium chloride to Reagent N1; and Reagent N3 prepared by adding MVK to Reagent N2 at 0.3 U/mL; were let stand at 37° C. for 20 minutes. Then, 0.1 mL of 0.5 M EDTA was added to each of these reagents to prepare Reagents N2E and N3E.

135 µL of Reagents N1, N2E, or N3E was added to 15 µL of a sample solution (distilled water or a solution of 570 U/mL HMGR derived from *Pseudomonas* sp. 1-MV [FERM BP-11063] that was expressed in *Escherichia coli* and dissolved in 10 mM Tris-HCl [pH 7.5]) at 37° C., 15 µL of distilled water or 50 nM MVA solution was added five minutes later, and then changes in absorbance [mABS] at a wavelength of 410 nm over 22 minutes were measured. Measurement was performed using Automated Analyzer BM9020 (JEOL Ltd.). The results are shown in Table 20.

TABLE 20

| | sample | |
|---|---|---|
| Reagent | DW | 570 U/ml HMGR |
| N1, DW | 2.62 | 70.85 |
| N2E, DW | 3.86 | 96.01 |

TABLE 20-continued

| | sample | |
|---|---|---|
| Reagent | DW | 570 U/ml HMGR |
| N3E, DW | 2.12 | 13.92 |
| N1, 50 nM MVA | 2.65 | 192.12 |
| N2E, 50 nM MVA | 3.91 | 226.48 |
| N3E, 50 nM MVA | 1.97 | 148.94 |

By removing MVA present in Reagent N1 with MVK, absorbance of a blank decreased from 70.85 to 13.92, and the sensitivity at the time of measurement of 50 nM MVA slightly improved from 121.27 (calculated by 192.12−70.85) to 135.02 (calculated by 148.94−13.92). Furthermore, by removing MVA present in Reagent N2E with MVK, absorbance of a blank decreased from 96.01 to 13.92, and the sensitivity at the time of measurement of 50 nM MVA was virtually equal, with 130.47 (calculated by 226.48−96.01) vs. 135.02 (calculated by 148.94−13.92). MVA that may be contaminated in CoA, T-NAD, NADH, ATP, and the like and MVA that may be contaminated in during the step of producing reagents can be reduced by treatment with MVK to 17.3% or lower and 12.8% or lower, respectively, of the amounts before treatment, and reagents with high sensitivity and high precision and with low absorbance in a blank reaction which are preferable for measurement were obtained.

Example 19

Production of enzyme cycling reagents for measuring MVA and/or HMG-CoA, comprising step of removing contaminated MVA using MVK derived from *Saccharomyces cerevisiae* (NBRC1136) that was expressed in *Escherichia coli* (membrane filtration)

2 mL each of: Reagent N4 prepared by adding 1 mM ATP and 1 mM magnesium chloride to Reagent N1; and Reagent N5 prepared by adding MVK to Reagent N4 at 0.4 U/mL; were let stand at 37° C. for 20 minutes. Then, ultrafiltration with a membrane having a molecular weight cut off of 10,000 was performed to prepare Reagents N4F and N5F.

135 µL of Reagent N4F or N5F was added to 15 µL of a sample solution (distilled water or a solution of 320 U/mL HMGR derived from *Pseudomonas* sp. 1-MV [FERM BP-11063] that was expressed in *Escherichia coli* and dissolved in 10 mM Tris-HCl [pH 7.5]) at 37° C., 15 µL of distilled water or 50 nM MVA solution was added five minutes later, and then changes in absorbance [mABS] at a wavelength of 410 nm over 26 minutes were measured. Measurement was performed using Automated Analyzer BM9020 (JEOL Ltd.). The results are shown in Table 21.

TABLE 21

| Reagent | sample | |
|---|---|---|
| | DW | 320 U/ml HMGR |
| N4F, DW | 5.17 | 58.57 |
| N5F, DW | 5.53 | 10.41 |
| N4F, 50 nM MVA | 5.23 | 129.04 |
| N5F, 50 nM MVA | 5.61 | 86.78 |

By removing MVA present in Reagent N4F with MVK, absorbance of a blank decreased from 58.57 to 10.41, and the sensitivity at the time of measurement of 50 nM MVA was virtually equal, with 70.47 (calculated by 129.04-58.57) vs. 76.37 (calculated by 86.78-10.41). MVA that may be contaminated in CoA, T-NAD, NADH, ATP, and the like and MVA that may be contaminated in during the step of producing reagents could be reduced to 9.1% or lower by treatment with MVK, similar to Example 18, reagents which are preferable for measurement with high sensitivity and high precision and with low absorbance at a blank reaction were obtained.

Example 20

Production of enzyme cycling reagents for measuring MVA and/or HMG-CoA, comprising step of removing contaminated HMG-CoA using HMGL derived from *Pseudomonas putida* KT2440 (ATCC47054) that was expressed in *Escherichia coli* (membrane filtration)

2 mL each of: Reagent N6 prepared by adding HMGL to Reagent N1 at 0.5 U/mL; Reagent N7 prepared by adding HMG-CoA to Reagent N1 at 125 nM; and Reagent N8 prepared by adding HMGL to Reagent N7 at 0.5 U/mL; were let stand at 37° C. for 20 minutes. Then, ultrafiltration was performed with a membrane having a molecular weight cut off of 10,000 to prepare Reagents N1F, N6F, N7F, or N8F.

135 µL of Reagents N1F, N6F, N7F or N8F was added to 15 µL of a sample solution (distilled water or 10, 5.0 or 100 nM MVA solution) at 37° C. Five minutes later, 15 µL of a solution (solution of 320 U/mL HMGR derived from *Pseudomonas* sp. 1-MV (FERM BP-11063) that was expressed in *Escherichia coli* and dissolved in 10 mM Tris-HCl (pH 7.5)) was added, and then changes in absorbance [mABS] at a wavelength of 410 nm over 4.6 minutes were measured. Measurement was performed using Automated Analyzer BM9020 (JEOL Ltd.). The results are shown in Table 22.

TABLE 22

| | MVA | | | |
|---|---|---|---|---|
| Reagent | DW | 10 nM | 50 nM | 100 nM |
| N1F | 4.25 | 10.56 | 35.99 | 70.07 |
| N6F | 4.23 | 11.13 | 36.73 | 72.16 |
| N7F | 305.99 | 311.02 | 334.36 | 356.70 |
| N8F | 3.81 | 10.62 | 36.23 | 71.22 |

By removing HMG-CoA present in Reagent N7F with HMGL, absorbance of a blank decreased from 305.99 to 3.81, and the sensitivity at the time of measurement of 100 nM MVA improved from 50.71 (calculated by 356.70-305.99) to 67.41 (calculated by 71.22-3.81). Even if HMG-CoA is contaminated during the reagent-producing step, HMGL treatment could completely remove 125 nM of HMG-CoA, and reagents which are preferable for measurement with high sensitivity and high precision and with low absorbance in a blank reaction were obtained.

Example 21

Measurement of MVA and HMG-CoA by enzyme cycling method using HMGR derived from *Archaeoglobus fulgidus* (NBRC100126) that was expressed in *Escherichia coli*

Figure 2:
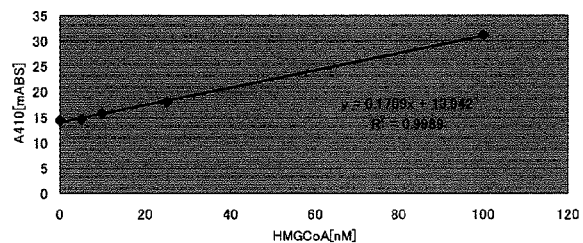
FIG. 2 is a graph showing results of the measurement of HMG-CoA using the enzyme cycling reaction in Example 21.
Figure 3:
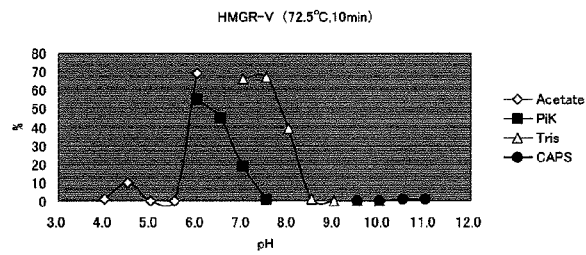
FIG. 3 is a graph showing results of the measurement of a residual activity of HMGR-V in Example 25.
Figure 4:
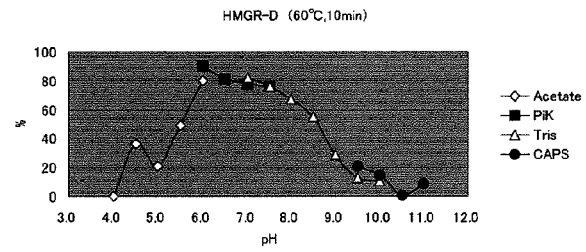
FIG. 4 is a graph showing results of the measurement of a residual activity of HMGR-D in Example 25.
Figure 5:
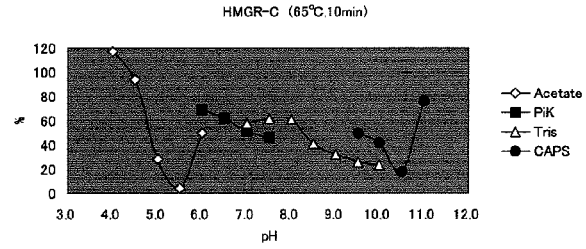
FIG. 5 is a graph showing results of the measurement of a residual activity of HMGR-C in Example 25.
Figure 6:
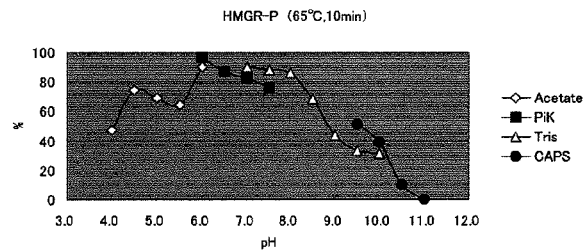
FIG. 6 is a graph showing results of the measurement of a residual activity of HMGR-P in Example 25.
Figure 7:
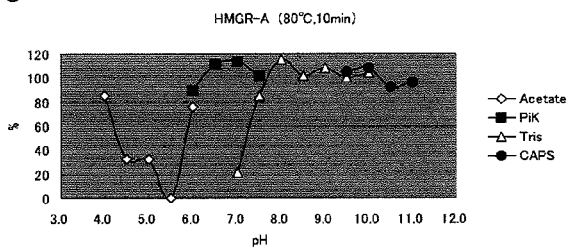
FIG. 7 is a graph showing results of the measurement of a residual activity of HMGR-A in Example 25.
Figure 8:
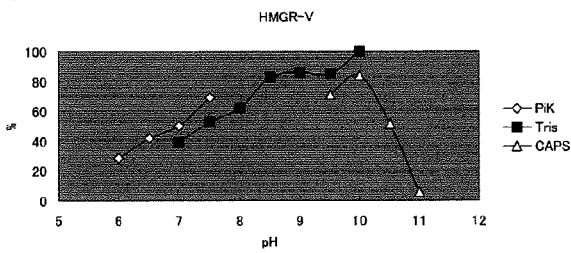
FIG. 8 is a graph showing results of the measurement of a relative activity of HMGR-V at each pH in Example 25.
Figure 9:
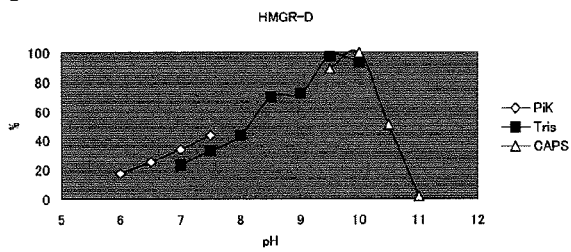
FIG. 9 is a graph showing results of the measurement of a relative activity of HMGR-D at each pH in Example 25.
Figure 10:
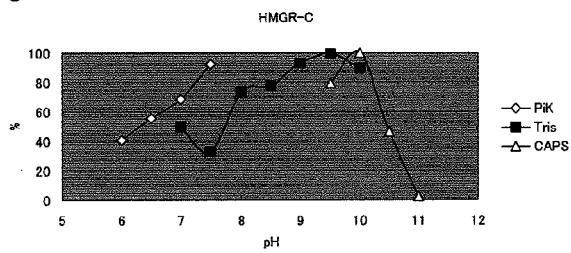
FIG. 10 is a graph showing results of the measurement of a relative activity of HMGR-C at each pH in Example 25.
Figure 11:
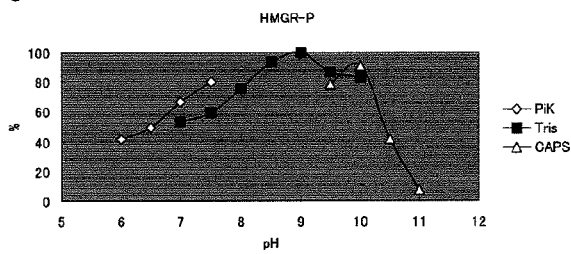
FIG. 11 is a graph showing results of the measurement of a relative activity of HMGR-P at each pH in Example 25.
Figure 12:
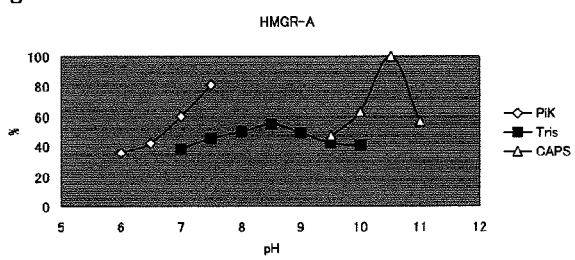
FIG. 12 is a graph showing results of the measurement of a relative activity of HMGR-A at each pH in Example 25.

135 µL of Reagent N3E described in Example 18 was added to 15 µL of a sample solution (distilled water or MVA solutions or HMG-CoA solutions shown in Table 23) at 37° C. Five minutes later, 15 µL of 12 U/mL HMGR solution dissolved in 10 mM Tris-HCl (pH 7.5) was added, and changes in absorbance [mABS] at a wavelength of 410 nm over 26 minutes were measured. Measurement was performed using Automated Analyzer BM9020 (JEOL Ltd.). The results are shown in Table 23 and FIGS. 1 and 2. It is shown that MVA and HMG-CoA could be measured with high precision.

TABLE 23

| | MVA[nM] | | | | HMGCoA[nM] | | | |
|---|---|---|---|---|---|---|---|---|
| DW | 5 | 10 | 25 | 50 | 5 | 10 | 25 | 100 |
| 14.31 | 15.73 | 17.37 | 22.23 | 30.13 | 14.59 | 15.62 | 18.02 | 31.09 |

Example 22

Enzyme cycling reaction using HMGR produced from *Pseudomonas* sp. 1-MV (FERM BP-11063)

180 µL of Reagent P1 (+) or P1 (−) was added to 10 µL of HMGR solution (3.3 U/mL HMGR solution produced by the method described in Example 1 or 3.3 U/mL HMGR solution produced by the method described in Example 1 and subjected to hydroxyapatite column chromatography in the same manner as described in Example 5) at 37° C. Five minutes later, 20 µL of Reagent P2 was added, and changes in absorbance [mABS] at a wavelength of 405 nm over five minutes were measured. Measurement was performed using Automated Analyzer 7170S (Hitachi, Ltd.). The results are shown in Table 24. It is shown that an enzyme cycling reaction occurred, and MVA could be measured. Furthermore, it is shown that when a high purity HMGR solution which was subjected to hydroxyapatite column chromatography was used, the blank signal was low and the measurement sensitivity was high.

TABLE 24

|  | Produced as described in Example 1 HMGR 3.3 U/ml | + Hydroxyapatite HMGR 3.3 U/ml |
|---|---|---|
| P1 (+) MVA 0.01 mM | 935.7 | 1315.9 |
| P1 (−) MVA 0 mM | 535.6 | 20.5 |
| delta | 400.1 | 1295.4 |

Example 23

Enzyme cycling reaction using HMGR produced from *Variovorax* sp. 5-MV (FERM BP-11064)

180 µL of Reagent P1 (+) or P1 (−) was added to 10 µL of HMGR solution (6.3, 3.2, or 1.6 U/mL HMGR solution produced by the method described in Example 2) at 37° C. Five minutes later, 20 µL of Reagent P2 was added, and changes in absorbance [mABS] at a wavelength of 405 nm over five minutes were measured. Measurement was performed using Automated Analyzer 7170S (Hitachi, Ltd.). The results are shown in Table 25. It is shown that an enzyme cycling reaction occurred, MVA could be measured, and the measurement sensitivity was increased when the amount of HMGR was increased.

TABLE 25

|  | HMGR [U/ml] | | |
|---|---|---|---|
|  | 6.3 | 3.2 | 1.6 |
| P1(+) MVA 0.01 mM | 1154.6 | 629.2 | 303.3 |
| P1(−) MVA 0 mM | 94.5 | 47.9 | 25 |
| delta | 1060.1 | 581.3 | 278.3 |

Example 24

Enzyme cycling reaction using HMGR produced from *Delftia* sp. 12-MV (FERM BP-11065) and HMGR produced from *Comamonas* sp. 25-MV (FERM BP-11066)

180 µL of Reagent P1 (+) or P1 (−) was added to 10 µL of HMGR solution (12.0 U/mL HMGR solution produced by the method described in Example 3 or 5.4 U/mL HMGR solution produced by the method described in Example 4) at 37° C. Five minutes later, 20 µL of Reagent P2 was added, and changes in absorbance [mABS] at a wavelength of 405 nm over five minutes were measured. Measurement was performed using Automated Analyzer 7170S (Hitachi, Ltd.). The results are shown in Table 26. It is shown that an enzyme cycling reaction occurred, and MVA could be measured.

TABLE 26

|  | *Delftia* sp. 12-MV HMGR 12.0 U/ml | *Comamonas* sp. 25-MV HMGR 5.4 U/ml |
|---|---|---|
| P1(+) MVA 0.01 mM | 462.4 | 497.3 |
| P1(−) MVA 0 mM | 377.4 | 468.7 |
| delta | 85.0 | 28.6 |

Example 25

Physicochemical properties of HMGR(HMGR-V) derived from *Variovorax* sp. 5-MV (FERM BP-11064), HMGR (HMGR-D) derived from *Delftia* sp. 12-MV (FERM BP-11065), HMGR(HMGR-C) derived from *Comamonas* sp. 25-MV (FERM BP-11066), HMGR(HMGR-P) derived from *Pseudomonas* sp. 1-MV (FERM BP-11063) that was expressed in *Escherichia coli*, and HMGR(HMGR-A) derived from *Archaeoglobus fulgidus* (NBRC100126) that was expressed in *Escherichia coli*

<Heat Stability>

Each HMGR was dissolved in 10 mM Tris-HCl (pH 7.5) and 0.05% BSA to obtain approximately 0.4 U/ml solution. This enzyme solution was treated at various temperatures for 10 minutes, and then a residual activity (%) was measured. The results are shown in Table 27.

TABLE 27

| | Heat stability (%) | | | | |
|---|---|---|---|---|---|
| ° C. | HMGR-V | HMGR-D | HMGR-C | HMGR-P | HMGR-A |
| 4 | 100 | 100 | 100 | 100 | 100 |
| 37 | 91 | 100 | 94 | 99 | 106 |
| 42 | — | 100 | — | — | — |
| 50 | 95 | 103 | — | — | — |
| 55 | 103 | 96 | — | 98 | — |
| 60 | 103 | 40 | 81 | 97 | — |
| 65 | 102 | 1 | 29 | 26 | — |
| 70 | 93 | — | 15 | — | — |
| 72.5 | 55 | — | — | — | — |
| 75 | 11 | — | — | — | — |
| 80 | — | — | — | — | 41 |
| 85 | — | — | — | — | 35 |
| 90 | — | — | — | — | 27 |

<pH Stability>

Each HMGR was dissolved in 20 mM buffer with various pH and 0.05% BSA to obtain approximately 0.4 U/ml solution. These enzyme solutions were treated for 10 minutes at the following temperature: HMGR-V at 72.5° C., HMGR-D at 60° C., HMGR-C at 65° C., HMGR-P at 65° C., and HMGR-A at 80° C. Then, a residual activity (%) was measured. The following buffers were used: acetic acid-sodium acetate at pH 4.0 to 6.0, potassium phosphate at pH 6.0 to 7.5, Tris-HCl at pH 7.0 to 10.0, and CAPS at pH 9.5 to 11.0. The results are shown in FIGS. 3 to 7. These enzyme solutions were stable at the following pH: HMGR-V at pH 6.0 to 8.0; HMGR-D at pH 5.5 to 8.5; HMGR-C at pH 4.0, pH 6.0 to 10.0 and pH 11.0; HMGR-P at pH 4.5 to 8.5; and HMGR-A at pH 4.0 and pH 6.0 to 11.0.

<Optimal pH>

Each HMGR was diluted with 10 mM Tris-HCl (pH 7.5) and 0.05% BSA at approximately 0.4 U/ml. HMGR activity of these enzyme solutions was measured in a reaction mixture containing 0.05% BSA, using Reagent B in which 50 mM Tris-HCl (pH 8.5) was replaced with 50 mM buffers at various pH. The relative activity (%) at each pH is shown in FIGS. 8 to 12. The following buffers were used: potassium phosphate at pH 6.0 to 7.5, Tris-HCl at pH 7.0 to 10.0, and CAPS at pH 9.5 to 11.0. The activity was the highest at pH 9.0 to 10.5 in all HMGR solutions. The optimal pH values are as follows: HMGR-V, pH 7.5 to 10.0; HMGR-D, pH 8.5 to 10.0; HMGR-C, pH 7.0 to 10.0; HMGR-P, pH 7.0 to 10.0; and HMGR-A, pH 7.0 to 10.5.

<Km Value: MVA>

The concentration of MVA in Reagent B was changed from 0.005 mM to 5 mM to determine the Km value of each HMGR. The Km values were as follows: HMGR-V, 0.36 mM; HMGR-D, 0.18 mM; HMGR-C, 0.66 mM; HMGR-P, 0.47 mM; and HMGR-A, 0.25 mM.

<Km Value: CoA>

BSA was added to Reagent B at 0.5%, the concentration of CoA was changed from 0.01 to 5 mM, and the Km value of each HMGR was determined. The Km values were as follows: HMGR-V, 0.066 mM; HMGR-D, 0.038 mM; HMGR-C, 0.073 mM; HMGR-P, 0.097 mM; and HMGR-A, 0.035 mM.

<Km Value: NAD>

BSA was added to Reagent B at 0.5%, the concentration of CoA was set at 0.5 mM, the concentrations of NAD were changed from 0.005 to 5 mM, and the Km value of each HMGR was determined. The Km values were as follows: HMGR-V, 0.19 mM; HMGR-D, 0.08 mM; HMGR-C, 0.26 mM; HMGR-P, 0.29 mM; and HMGR-A, 0.17 mM.

<Molecular Weight: Gel Filtration>

Using TSK gel G3000SWxL (Tosoh Corporation), the molecular weight of each HMGR was determined by gel filtration using 50 mM Pi-K (pH 7.5), 0.2 M sodium sulfate, and 0.05% sodium azide as mobile phases. The molecular weights were as follows: HMGR-V, 330,000; HMGR-D, 260,000; HMGR-C, 270,000; HMGR-P, 280,000; HMGR-A, 410,000.

<Molecular Weight: SDS-PAGE>

The molecular weight of each HMGR was determined by SDS-PAGE. The molecular weights were as follows: HMGR-V, 42,000; HMGR-D, 42,000; HMGR-C, 42,000; HMGR-P, 45,000; and HMGR-A, 40,000.

<Amino Acid Sequence>

The N terminal amino acid sequence of HMGR-V is shown in SEQ ID NO: 25, but the first amino acid is Met or Val. The N terminal amino acid sequence of HMGR-D is shown in SEQ ID NO: 26, but the first amino acid is Met, Val, or Thr, and the 24th amino acid is Asp or Ala. The N terminal amino acid sequence of HMGR-C is shown in SEQ ID NO: 27, but the first amino acid is Met, Ala, or Thr, the 23rd amino acid is Thr or Leu, and the 35th amino acid is Leu or Glu.

Example 26

Measurement of MVA in human plasma and serum by enzyme cycling method using HMGR derived from *Pseudomonas* sp. 1-MV (FERM BP-11063) that was expressed in *Escherichia coli* and MVK derived from *Saccharomyces cerevisiae* (NBRC1136) that was expressed in *Escherichia coli*

150 µL of Reagent Q1A or Q1B was added to 5 µL of a sample solution (distilled water, 50 nM MVA [100 nM D,L-MVA], Plasma 1, Plasma 2, Serum 1, or Serum 2), and the mixture was let stand at 37° C. for five minutes. Then, 50 µL of Reagent Q2 was added, and one minute after the addition, changes in absorbance at wavelength of 405 nm (sub-wavelength, 660 nm) over four minutes were measured. The results are shown in Table 28. The calculated values using the measured values after removal of MVK shows more accurate D-MVA concentrations because a blank value by reaction of HMGcoA present in the sample or non-specific reaction was subtracted. Measurement was performed using Automated Analyzer 7170S (Hitachi, Ltd.). The plasma and serum samples were purchased from Kohjin Bio Co., Ltd. (Plasma 1: normal human plasma (pooled) with sodium citrate; Plasma 2: normal human plasma (pooled) with heparin; Serum 1: normal human serum (pooled); Serum 2: normal human serum (individual subject))

TABLE 28

| sample | ReagentQ1A Δ405 [mABS] | ReagentQ1A D-MVA [nM] | ReagentQ1B Δ405 [mABS] | Calculation (Q1A − Q1B) Δ405 [mABS] | Calculation (Q1A − Q1B) D-MVA [nM] |
|---|---|---|---|---|---|
| DW | 13.15 | 0.0 | 10.25 | 2.90 | 0.0 |
| 50 nM D-MVA | 32.20 | 50.0 | 10.40 | 21.80 | 50.0 |
| Plasma 1 | 34.90 | 57.1 | 16.50 | 18.40 | 41.0 |
| Plasma 2 | 27.70 | 38.2 | 12.90 | 14.80 | 31.5 |
| Serum 1 | 64.40 | 134.5 | 11.15 | 53.25 | 133.2 |
| Serum 2 | 40.55 | 71.9 | 18.65 | 21.90 | 50.3 |

Example 27

Measurement of MVA in human urine by enzyme cycling method using HMGR derived from *Pseudomonas* sp. 1-MV (FERM BP-11063) that was expressed in *Escherichia coli* and MVK derived from *Saccharomyces cerevisiae* (NBRC1136) that was expressed in *Escherichia coli*

120 µL of Reagent R1 was added to 7.5 µL of a sample solution (distilled water, 50 nM MVA [100 nM D,L-MVA], Diluted Urine 1 [Urine 1 200-fold diluted with distilled water], Diluted Urine 2 [Urine 2 200-fold diluted with distilled water]), and the mixture was let stand at 37° C. for five minutes. Then, 30 µL of Reagent R2 was added, and then changes in absorbance at a wavelength of 410 nm over 10 minutes were measured. Measurement was performed using Automated Analyzer BM9020 (JEOL Ltd.). Urines 1 and 2 were collected from the same subject at 4:00 and 17:00 on the same day. Creatinine in the urine sample was measured using a creatinine measuring reagent (L Type Wako CRE.M: Wako Pure Chemical Industries, Ltd.). The results are shown in Tables 29 and 30. The value corrected with creatinine serves as an indicator with reduced influence of the concentration of urine.

TABLE 29

| sample | Δ405 [mABS] | D-MVA [nM] |
|---|---|---|
| DW | 27.8 | 0.0 |
| 50 nM D-MVA | 86.0 | 50.0 |
| Diluted urine 1 | 57.7 | 25.7 |
| Diluted urine 2 | 41.0 | 11.3 |

TABLE 30

| | D-MVA [nM] | Creatinine [mg/dL] | D-MVA/Cre [nM · dL/mg] |
|---|---|---|---|
| Urine 1 | 5137 | 243 | 21.1 |
| Urine 2 | 2268 | 120 | 18.9 |

Example 28

Measurement of MVA in food by enzyme cycling method using HMGR derived from *Pseudomonas* sp. 1-MV (FERM BP-11063) that was expressed in *Escherichia coli* and MVK derived from *Saccharomyces cerevisiae* (NBRC1136) that was expressed in *Escherichia coli*

80 µL of Reagent K1 (+) or K1 (−) was added to 16 µL of a sample solution (distilled water, MVA solution, Samples 1 to 12 in Table 33) at 37° C., the mixture was incubated for 1.7 minutes, 24 µL of Reagent K2 was further added, the mixture was incubated for further 3.3 minutes, 40 μL of reagent K3 was added, and the mixture was incubated for further 3.8 minutes. Then, 16 μL of Reagent K4 (+) or K4 (−) was added, and changes in absorbance at a wavelength of 410 nm over 22.0 minutes [mABS] were measured. Measurement was performed using an automated analyzer BM9020 (JEOL Ltd.). Combinations of reagents used for measurement and measured values are shown in Tables 31 and 32. The measured values MVA [nM] were obtained by drawing a calibration curve, using distilled water and D-MVA 100 nM (200 nM as D,L-MVA). When distilled water was measured, differences in absorbance [mABS] were noted among combinations of Reagents K1 (+), K2, K3, and K4 (+) and Reagents K1 (−), K2, K3, and K4 (−). This may be caused by MVA contained in reagents as explained in Example 19. The methods for preparing Samples 1 to 12 are shown in Table 33. The sample numbers in Table 33 correspond to the sample numbers in Tables 31 and 32.

TABLE 31

|  | DW | MVA 2.5 nM | MVA 5 nM | MVA 25 nM | MVA 50 nM | MVA 100 nM | sample 1 | sample 2 | sample 3 |
|---|---|---|---|---|---|---|---|---|---|
| K1 (+), K2, K3, K4 (+) [mABS] | 11.8 | 12.3 | 12.5 | 11.9 | 12.6 | 13.4 | 22.9 | 29.6 | 12.5 |
| K1 (−), K2, K3, K4 (−) [mABS] | 121.8 | 130.3 | 140.1 | 206.1 | 282.6 | 413.2 | 303.0 | 169.9 | 348.4 |
| delta [mABS] | 110.0 | 118.0 | 127.6 | 194.2 | 270.0 | 399.8 | 280.1 | 140.3 | 335.9 |
| Measured value MVA [nM] | 0.0 | 2.8 | 6.1 | 29.1 | 55.2 | 100.0 | 58.7 | 10.5 | 78.0 |

TABLE 32

|  | sample 4 | sample 5 | sample 6 | sample 7 | sample 8 | sample 9 | sample 10 | sample 11 | sample 12 |
|---|---|---|---|---|---|---|---|---|---|
| K1 (+), K2, K3, K4 (+) [mABS] | 25.6 | 16.7 | 13.1 | 13.3 | 16.4 | 15.6 | 9.1 | 13.4 | 12.6 |
| K1 (−), K2, K3, K4 (−) [mABS] | 235.1 | 128.8 | 404.3 | 363.9 | 195.2 | 221.6 | 129.2 | 198.6 | 246.0 |
| delta [mABS] | 209.5 | 112.1 | 391.2 | 350.6 | 178.8 | 206.0 | 120.1 | 185.2 | 233.4 |
| Measured value MVA [nM] | 34.3 | 0.7 | 97.0 | 83.0 | 23.7 | 33.1 | 3.5 | 25.9 | 42.6 |

TABLE 33

| sample | Product | Preparation method |
|---|---|---|
| 1 | Apple juice | Dilute 100% juice 25-fold with distilled water. |
| 2 | Pineapple juice | Dilute 100% juice 5-fold with distilled water. |
| 3 | Flour | Suspend 100 mg of flour in 1 mL of distilled water, centrifuge, and dilute the supernatant 20-fold. |
| 4 | Carrot | Suspend 500 mg of grated carrots in 12 mL of distilled water, centrifuge, and dilute the supernatant 5-fold with distilled water. |
| 5 | Black tea | Dilute black tea 5-fold with distilled water. |
| 6 | Japanese sake | Dilute Japanese sake 100-fold with distilled water. |
| 7 | Beer | Dilute beer 100-fold with distilled water. |
| 8 | Whiskey | Dilute whiskey 5-fold with distilled water. |
| 9 | Bread | Suspend 200 mg of bread in 1 mL of distilled water, centrifuge, and dilute the supernatant 5-fold with distilled water. |
| 10 | Rice | Suspend 200 mg of rice in 1 mL of distilled water, centrifuge, and dilute the supernatant 5-fold with distilled water. |
| 11 | Yogurt | Suspend 300 mg of yogurt in 1 mL of distilled water, centrifuge, and dilute the supernatant 5-fold with distilled water. |
| 12 | Salmon meat | Suspend 200 mg of salmon meat in 1 mL of distilled water, centrifuge, and dilute the supernatant 20-fold with distilled water. |

Example 29

Standard MVA measuring method (MVK method) and MVA reference material

D,L-Mevalonic acid lactone (Sigma M4667) was accurately weighed to prepare a 0.5 M solution, and this solution was accurately diluted to prepare 0.05, 0.1, 0.2, and 0.5 mM D,L-MVA solutions. D-Mevalonic acid lactone (Tokyo Chemical Industry M1347) was accurately weighed to prepare a 0.5 M solution, and this solution was accurately diluted to prepare 0.05, 0.1, 0.2, and 0.5 mM D-MVA solutions.

Two aqueous NADH solutions A and B were prepared. The 1-cm absorbances measured at 340 nm using a double monochromator spectrophotometer (Shimadzu UV-2550) were 1.0915 and 2.683.

To confirm precision of the automated analyzer BM9020 (JEOL Ltd.) at a measurement wavelength of 340 nm and a sub-wavelength of 658 nm, 75 μL of distilled water was added to 25 μL of aqueous NADH solution A or B at 37° C., absorbance Aa was measured, 75 μL of distilled water was further added 8.8 minutes later, and absorbance Ab was measured. The absorbance Aa and the absorbance Ab of aqueous solution A were 0.23602 and 0.13452, respectively. The absorbance Aa and the absorbance Ab of aqueous NADH solution B were 0.59107 and 0.33786, respectively. Device coefficients of BM9020 for these solutions were 0.86

(=0.23602/1.0915×25/[25+75]), 0.86 (=0.13425/1.0915×25/[25+75+75]), 0.88 (=0.59107/2.683×25/[25+75]), and 0.88 (=0.33786/2.683×25/[25+75+75]), with the mean of 0.87.

MVK derived from *Saccharomyces cerevisiae* (NBRC1136) that was expressed in *Escherichia coli* was used.

Figure 13:
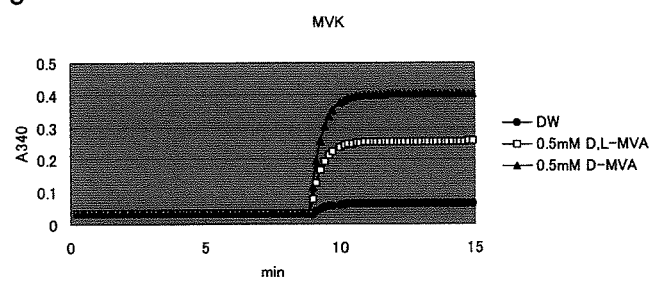
FIG. 13 is a graph showing results of the analysis of reaction time courses using the MVK method in Example 29.

75 µL of Reagent S1 was added to 25 µL of distilled water, a D,L-MVA solution, or a D-MVA solution at 37° C., 75 µL of Reagent S2 was added 8.8 minutes later, and absorbance [ABS] A1 before addition of S2 and absorbance [ABS] A2 at 6 minutes after addition of S2 were measured at a measurement wavelength of 340 nm using Automated Analyzer BM9020 (JEOL Ltd.). The reaction time courses when the samples were distilled water, 0.5 mM D,L-MVA, and 0.5 mM D-MVA are shown in FIG. 13.

From these results and the molar absorbance coefficient of NADH 6.3×1000 (l/[mol.cm]), produced NADH was calculated as follows:

Produced NADH(nmol)=($A2$×175−$A1$×100)/(6.3× 0.87).

The amount of NADH produced from D-MVA is difference between the value of produced NADH and the value from a blank reaction using a sample of distilled water. By this equation, the amount of D-MVA contained in D,L-MVA solution or D-MVA solution was determined. The results are shown in Table 34. The mean D-MVA content in D,L-Mevalonic acid lactone (Sigma M4667) was 0.50, and the mean D-MVA content in D-Mevalonic acid lactone (Tokyo Chemical Industry M1347) was 0.88. Thus, it is shown that an accurate amount of MVA can be measured by establishing the standard measuring method, and the MVA reference material can be prepared.

As the apparatus coefficient for Automated Analyzer BM9020 (JEOL Ltd.), 0.87, which was determined in Example 29, was used.

HMGR derived from *Pseudomonas* sp. 1-MV (FERM BP-11063) and expressed in *Escherichia coli* and HMGL derived from *Pseudomonas putida* KT2440 (ATCC47054) and expressed in *Escherichia coli* were used.

Figure 14:
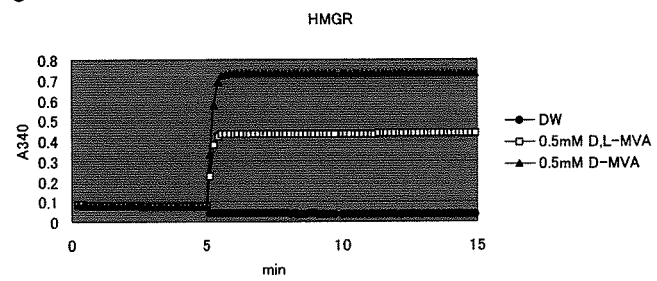
FIG. 14 is a graph showing results of the analysis of reaction time courses using the HMGR method in Example 30.

75 µL of Reagent T1 was added to 25 µL of distilled water, a D,L-MVA solution, or a D-MVA solution at 37° C., 75 µL of Reagent T2 was added 5 minutes later, absorbance [ABS] A1 before the addition of T2 and absorbance [ABS] A2 at 13 minutes after the addition of T2 were measured at a measurement wavelength 340 nm using an automated analyzer BM9020 (JEOL Ltd.). The reaction time courses when the samples were distilled water, 0.5 mM D,L-MVA, and 0.5 mM D-MVA are shown in FIG. 14.

From these results and the molar absorbance coefficient of NADH of 6.3×1000 (l/[mol.cm]), produced NADH was calculated as follows:

Produced NADH(nmol)=($A2$×175−$A1$×100)/(6.3× 0.87).

The amount of NADH produced from D-MVA is difference between the value of produced NADH and the value from a blank reaction using a sample of distilled water. By this equation, the amount of D-MVA contained in a D,L-MVA solution or a D-MVA solution was determined. The results are shown in Table 35. The mean D-MVA content in

TABLE 34

|  | distiled water | D,L-MVA | | | | D-MVA | | | |
| --- | --- | --- | --- | --- | --- | --- | --- | --- | --- |
|  |  | 0.05 mM | 0.1 mM | 0.2 mM | 0.5 mM | 0.05 mM | 0.1 mM | 0.2 mM | 0.5 mM |
| A1 | 0.03242 | 0.03258 | 0.03250 | 0.03247 | 0.03249 | 0.03248 | 0.03254 | 0.03261 | 0.03280 |
| A2 | 0.06444 | 0.08409 | 0.10358 | 0.14051 | 0.25678 | 0.09910 | 0.13427 | 0.20007 | 0.40341 |
| NADH(nmol) | 1.466 | 2.090 | 2.714 | 3.894 | 7.606 | 2.572 | 3.693 | 5.793 | 12.282 |
| NADH(nmol) derived from D-MVA |  | 0.624 | 1.248 | 2.428 | 6.140 | 1.106 | 2.227 | 4.327 | 10.816 |
| D-MVA content |  | 0.50 | 0.50 | 0.49 | 0.49 | 0.88 | 0.89 | 0.87 | 0.87 |

Example 30

Standard MVA measuring method (HMGR method) and MVA reference material

D-MVA solutions at various concentrations prepared in Example 29 were used.

D,L-Mevalonic acid lactone (Sigma M4667) was 0.50, and the mean D-MVA content in D-Mevalonic acid lactone (Tokyo Chemical Industry M1347) was 0.90. Thus, it is shown that an accurate amount of MVA can be measured by establishing the standard measuring method, and that the MVA reference material can be prepared.

TABLE 35

|  | distiled water | D,L-MVA | | | | D-MVA | | | |
| --- | --- | --- | --- | --- | --- | --- | --- | --- | --- |
|  |  | 0.05 mM | 0.1 mM | 0.2 mM | 0.5 mM | 0.05 mM | 0.1 mM | 0.2 mM | 0.5 mM |
| A1 | 0.07588 | 0.07575 | 0.07643 | 0.07571 | 0.07573 | 0.07581 | 0.07580 | 0.07586 | 0.07588 |
| A2 | 0.03996 | 0.07974 | 0.11890 | 0.19610 | 0.43355 | 0.11079 | 0.18304 | 0.32062 | 0.73029 |
| NADH(nmol) | −0.109 | 1.164 | 2.402 | 4.880 | 12.461 | 2.154 | 4.461 | 8.853 | 21.933 |
| NADH(nmol) derived from D-MVA |  | 1.272 | 2.510 | 4.988 | 12.569 | 2.263 | 4.570 | 8.961 | 22.041 |
| D-MVA content |  | 0.51 | 0.50 | 0.50 | 0.50 | 0.91 | 0.91 | 0.90 | 0.88 |

Preparation Example 1

Media

The media used in the above-mentioned Examples are described below.

Medium A

Medium A was prepared by adding 3% A2 and 0.5% A3 to A1.

TABLE 36

| A1 | |
|---|---|
| 0.7% | Yeast extract |
| 1 mg/L | thiamine |
| 2 mg/ml | riboflavin |
| 2 mg/L | niconinic acid |
| 2 mg/L | calcium panthothenate |
| 2 mg/L | pyridoxine HCl |
| 0.1 mg/L | biotin |
| 1 mg/L | p-aminobenzoic acid |
| 0.1 mg/L | folic acid |
| (Adjusted to pH 5.5 then autoclaved) | |
| A2 | |
| 128 g/L | Na2HPO4—7H2O |
| 30 g/L | KH2PO4 |
| 5 g/L | NaCl |
| 10 g/L | NH4Cl |
| (Adjusted to pH 5.5 then autoclaved) | |
| A3 | |
| 5% | D,L-mevalonic acid |
| (Sterilized by filtration) | |

Medium B

Medium B was prepared by adding 3% B2 and 0.5% B3 to B1.

TABLE 37

| B1 | |
|---|---|
| 0.7% | Yeast extract |
| 1 mg/L | thiamine |
| 2 mg/ml | riboflavin |
| 2 mg/L | niconinic acid |
| 2 mg/L | calcium panthothenate |
| 2 mg/L | pyridoxine HCl |
| 0.1 mg/L | biotin |
| 1 mg/L | p-aminobenzoic acid |
| 0.1 mg/L | folic acid |
| (Adjusted to pH 7 then autoclaved) | |
| B2 | |
| 128 g/L | Na2HPO4—7H2O |
| 30 g/L | KH2PO4 |
| 5 g/L | NaCl |
| 10 g/L | NH4Cl |
| (Adjusted to pH 7 then autoclaved) | |
| B3 | |
| 5% | D,L-mevalonic acid |
| (Sterilized by filtration) | |

Medium C

Medium C was prepared by adding 3% C2 and 0.5% C3 to C1.

TABLE 38

| C1 | |
|---|---|
| 0.7% | Yeast extract |
| 1 mg/L | thiamine |

TABLE 38-continued

| | |
|---|---|
| 2 mg/ml | riboflavin |
| 2 mg/L | niconinic acid |
| 2 mg/L | calcium panthothenate |
| 2 mg/L | pyridoxine HCl |
| 0.1 mg/L | biotin |
| 1 mg/L | p-aminobenzoic acid |
| 0.1 mg/L | folic acid |
| (Adjusted to pH 9 then autoclaved) | |
| C2 | |
| 128 g/L | Na2HPO4—7H2O |
| 30 g/L | KH2PO4 |
| 5 g/L | NaCl |
| 10 g/L | NH4Cl |
| (Adjusted to pH 9 then autoclaved) | |
| C3 | |
| 5% | D,L-mevalonic acid |
| (Sterilized by filtration) | |

Preparation Example 2

Reagents

Compositions of the reagents used in the above-mentioned Examples are shown below:

TABLE 39

| Reagent A | |
|---|---|
| 50 mM | Tris-HCl(pH 8.5) |
| 0.005% | ntro blue tetrazolium choloride |
| 0.2 mM | coenzymeA |
| 0.1% | triton X-100 |
| 1 mM | NAD |
| 1 mM | NADP |
| 5 U/ml | Diaphorase(Manufactured by Toyobo Co., Ltd.) |
| 5 mM | D,L-mevalonic acid |

TABLE 40

| Reagent B | |
|---|---|
| 50 mM | Tris-HCl(pH 8.5) |
| 0.005% | ntro blue tetrazolium choloride |
| 0.2 mM | coenzymeA |
| 0.1% | triton X-100 |
| 1 mM | NAD |
| 5 U/ml | Diaphorase(Manufactured by Toyobo Co., Ltd.) |
| 5 mM | D,L-mevalonic acid |

TABLE 41

| Reagent C | |
|---|---|
| 50 mM | Tris-HCl(pH 7.5) |
| 0.005% | ntro blue tetrazolium choloride |
| 5 mM | Glucose |
| 1 mM | MgCl2 |
| 1 mM | NAD |
| 1 mM | ATP |
| 5 U/ml | ADP-dependent Hexokinase (ADP-HKP II: Manufactured by Asahi Kasei Pharma Corporation) |
| 5 U/ml | Glucose-6-phosphate dehydrogenase (Manufactured by Toyobo Co., Ltd.) |
| 5 U/ml | Diaphorase (Manufactured by Toyobo Co., Ltd.) |
| 2 mM | D,L-mevalonic acid |

TABLE 42

| | Reagent Cb |
|---|---|
| 50 mM | Tris-HCl(pH 7.5) |
| 0.005% | ntro blue tetrazolium choloride |
| 5 mM | Glucose |
| 1 mM | MgCl2 |
| 1 mM | NAD |
| 1 mM | ATP |
| 5 U/ml | ADP-dependent Hexokinase (ADP-HKP II: Manufactured by Asahi Kasei Pharma Corporation) |
| 5 U/ml | Glucose-6-phosphate dehydrogenase (Manufactured by Toyobo Co., Ltd.) |
| 5 U/ml | Diaphorase (Manufactured by Toyobo Co., Ltd.) |

TABLE 43

| | Reagent D1 |
|---|---|
| 25 mM | Tris-HCl(pH 9.0) |
| 0.25 mM | NADH |
| 6.25 U/ml | 3-Hydroxybutyrate Dehydrogenase (3-HBDH II: Manufactured by Asahi Kasei Pharma Corporation) |

TABLE 44

| | Reagent D2 |
|---|---|
| 0.75 mM | D,L-HMGCoA |

TABLE 45

| | Reagent E1 |
|---|---|
| 50 mM | Glycine-NaOH(pH 10.0) |
| 1 mM | T-NAD |
| 0.2 mM | NADH |

TABLE 46

| | Reagent E2 |
|---|---|
| 50 mM | Glycine-NaOH(pH 10.0) |
| 1 mM | T-NAD |
| 0.2 mM | NADH |
| 1 mM | CoA |

TABLE 47

| | Reagent E3 |
|---|---|
| 50 mM | Glycine-NaOH(pH 10.0) |
| 1 mM | T-NAD |
| 0.2 mM | NADH |
| 1 mM | CoA |
| 1 mM | ATP |
| 1 mM | MgCl2 |

TABLE 48

| | Reagent E4 |
|---|---|
| 50 mM | Glycine-NaOH(pH 10.0) |
| 1 mM | T-NAD |
| 0.2 mM | NADH |
| 1 mM | CoA |
| 1 mM | ATP |

TABLE 48-continued

| | Reagent E4 |
|---|---|
| 1 mM | MgCl2 |
| 1 U/ml | MVK |

TABLE 49

| | Reagent E5 |
|---|---|
| 50 mM | Glycine-NaOH(pH 10.0) |
| 1 mM | T-NAD |
| 0.2 mM | NADH |
| 1 mM | CoA |
| 1 U/ml | HMGL |

TABLE 50

| | Reagent E11 |
|---|---|
| 10 mM | Tris-HCl(pH 8.0) |
| 400 U/ml | HMGR |

TABLE 51

| | Reagent E12 |
|---|---|
| 10 mM | Tris-HCl(pH 8.0) |

TABLE 52

| | Reagent F1 |
|---|---|
| 50 mM | Glycine-NaOH(pH 10.0) |
| 1 mM | T-NAD |
| 57 U/ml | HMGR |

TABLE 53

| | Reagent F2 |
|---|---|
| 50 mM | Glycine-NaOH(pH 10.0) |
| 0.2 mM | NADH |

TABLE 54

| | Reagent G1 |
|---|---|
| 50 mM | Glycine-NaOH(pH 10.0) |
| 1 mM | T-NAD |
| 0.2 mM | NADH |
| 32 U/ml | HMGR |

TABLE 55

| | Reagent G2 |
|---|---|
| 50 mM | Glycine-NaOH(pH 10.0) |
| 1 mM | T-NAD |
| 0.2 mM | NADH |
| 63 U/ml | HMGR |

TABLE 56

| Reagent H1 | |
|---|---|
| 20 mM | Glycine-NaOH(pH 9.0) |
| 2 mM | ATP |
| 2 mM | MgCl2 |

TABLE 57

| Reagent H2 | |
|---|---|
| 20 mM | Glycine-NaOH(pH 9.0) |
| 2 mM | ATP |
| 2 mM | MgCl2 |
| 2 U/ml | MVK |

TABLE 58

| Reagent J1(+) | |
|---|---|
| 20 mM | Glycine-NaOH(pH 10.5) |
| 2 mM | ATP |
| 2 mM | MgCl2 |
| 2 U/ml | MVK |

TABLE 59

| Reagent J1(−) | |
|---|---|
| 20 mM | Glycine-NaOH(pH 10.5) |
| 2 mM | ATP |
| 2 mM | MgCl2 |

TABLE 60

| Reagent J2 | |
|---|---|
| 0.222M | NaOH |

TABLE 61

| Reagent J3 | |
|---|---|
| 200 mM | Glycine-NaOH |
| 44.5 mM | Citric acid |
| 4 mM | CoA |
| 4 mM | T-NAD |
| 160 U/ml | HMGR |
| pH 5.7 | |

TABLE 62

| Reagent J4 | |
|---|---|
| 50 mM | Glycine-NaOH(pH 10.0) |
| 1.8 mM | NADH |

TABLE 63

| Reagent K1(+) | |
|---|---|
| 20 mM | Glycine-NaOH(pH 10.5) |
| 2 mM | ATP |
| 2 mM | MgCl2 |
| 2 U/ml | MVK |

TABLE 64

| Reagent K1(−) | |
|---|---|
| 20 mM | Glycine-NaOH(pH 10.5) |
| 2 mM | ATP |
| 2 mM | MgCl2 |

TABLE 65

| Reagent K2 | |
|---|---|
| 200 mM | Glycine-NaOH(pH 10.0) |

TABLE 66

| Reagent K3 | |
|---|---|
| 50 mM | Glycine-NaOH(pH 10.0) |
| 4 mM | CoA |
| 4 mM | T-NAD |
| 50 U/ml | HMGR |

TABLE 67

| Reagent K4(+) | |
|---|---|
| 50 mM | Glycine-NaOH(pH 10.0) |
| 50 mM | EDTA |
| 1.8 mM | NADH |

TABLE 68

| Reagent K4(−) | |
|---|---|
| 50 mM | Glycine-NaOH(pH 10.0) |
| 50 mM | EDTA |
| 1.8 mM | NADH |
| 10 U/ml | MVK |

TABLE 69

| Reagent L1 | |
|---|---|
| 20 mM | Tris-HCl(pH 9.0) |
| 11 U/ml | HMGL |

TABLE 70

| Reagent L2 | |
|---|---|
| 20 mM | Tris-HCl(pH 9.0) |

TABLE 71

| Reagent M1(+) | |
|---|---|
| 10 mM | Tris-HCl(pH 9.0) |
| 0.4 U/ml | HMGL |

TABLE 72

| Reagent M(−) | |
| --- | --- |
| 10 mM | Tris-HCl(pH 9.0) |

TABLE 73

| Reagent M2 | |
| --- | --- |
| 0.222M | NaOH |

TABLE 74

| Reagent M3 | |
| --- | --- |
| 200 mM | Glycine-NaOH |
| 44.5 mM | Citric acid |
| 4 mM | CoA |
| 4 mM | T-NAD |
| 50 U/ml | HMGR |
| pH 5.7 | |

TABLE 75

| Reagent M4 | |
| --- | --- |
| 50 mM | Glycine-NaOH(pH 10.0) |
| 1.8 mM | NADH |

TABLE 76

| Reagent N1 | |
| --- | --- |
| 50 mM | Glycine-NaOH(pH 10.0) |
| 1 mM | T-NAD |
| 0.2 mM | NADH |
| 1 mM | CoA |

TABLE 77

| Reagent P1(+) | |
| --- | --- |
| 50 mM | Tris-HCl(pH 8.5) |
| 1 mM | T-NAD |
| 1 mM | CoA |
| 0.01 mM | MVA |

TABLE 78

| Reagent P1(−) | |
| --- | --- |
| 50 mM | Tris-HCl(pH 8.5) |
| 1 mM | T-NAD |
| 1 mM | CoA |

TABLE 79

| Reagent P2 | |
| --- | --- |
| 50 mM | Tris-HCl(pH 8.5) |
| 2 mM | NADH |

TABLE 80

| Reagent Q1A | |
| --- | --- |
| 50 mM | Glycine-NaOH |
| 0.18 mM | NADH |
| 30 mM | NaHCO3 |
| 0.7 mM | MgCl2 |
| 0.7 mM | ATP |
| 0.07% | Tween80 |
| 0.05% | NaN3 |
| pH 9.4 | |

TABLE 81

| Reagent Q1B | |
| --- | --- |
| 50 mM | Glycine-NaOH |
| 0.18 mM | NADH |
| 30 mM | NaHCO3 |
| 0.7 mM | MgCl2 |
| 0.7 mM | ATP |
| 0.07% | Tween80 |
| 0.05% | NaN3 |
| 0.8 U/ml | MVK |
| pH 9.4 | |

TABLE 82

| Reagent Q2 | |
| --- | --- |
| 100 mM | HEPES |
| 6 mM | EDTA |
| 2.4 mM | CoA |
| 30 mM | T-NAD |
| 67 U/ml | HMGR |
| 0.02% | ProClin300 |
| pH 6.0 | |

TABLE 83

| Reagent R1 | |
| --- | --- |
| 100 mM | Glycine-NaOH(pH 8.5) |
| 1.84 mM | T-NAD |
| 1.23 mM | CoA |
| 20 U/ml | HMGR |

TABLE 84

| Reagent R2 | |
| --- | --- |
| 989 mM | Glycine-NaOH(pH 9.5) |
| 1.13 mM | NADH |

TABLE 85

| Reagent S1 | |
| --- | --- |
| 10 mM | Glycine-NaOH(pH 10.5) |
| 5 mM | Glucose |
| 1 mM | MgCl2 |
| 1 mM | NAD |
| 1 mM | ATP |
| 0.5 U/ml | MVK |
| 10 U/ml | ADP-dependent Hexokinase (ADP-HKP II: Manufactured by Asahi Kasei Pharma Corporation) |

TABLE 86

| | Reagent S2 |
|---|---|
| 10 mM | Tris-HCl(pH 8.5) |
| 5 U/ml | Glucose-6-phosphate dehydogenase(Manufactured by Toyobo Co., Ltd.) |

TABLE 87

| | Reagent T1 |
|---|---|
| 50 mM | Glycine-NaOH(pH 10.5) |
| 2 mM | NAD |
| 2 mM | CoA |
| 5 U/ml | HMGL |

TABLE 88

| | Reagent T2 |
|---|---|
| 10 mM | Tris-HCl(pH 8.5) |
| 5 U/ml | HMGR |

This application is based on Japanese Patent Application No. 2009-009177 filed on Jan. 19, 2009, and the content thereof is hereby incorporated by reference into this application.

INDUSTRIAL APPLICABILITY

According to the present invention, MVA and/or HMG-CoA in a biological sample which is an indicator of the amount of a cholesterol synthesized in the body or CoA in a biological sample which is an indicator of lipid metabolism in the body can be measured conveniently with ultra-high-sensitivity and high precision. The above-mentioned measurement can be performed for many specimens using a general-purpose automated analyzer. Therefore, many specimens can be accurately measured in routine clinical tests and the like, and thus the present invention has industrial applicability in diagnoses of pathological conditions and the like.

FREE TEXT FOR SEQUENCE LISTING

SEQ ID NO: 1 is the amino acid sequence of HMGR derived from *Pseudomonas* sp. 1-MV (FERN BP-11063).

SEQ ID NO: 2 is the amino acid sequence of HMGR derived from *Pseudomonas mevalonii*.

SEQ ID NO: 3 is the amino acid sequence of HMGR derived from *Archaeoglobus fulgidus* (NBRC100126).

SEQ ID NO: 4 is the nucleotide sequence of POP promoter.

SEQ ID NO: 5 is the nucleotide sequence of the MVK gene of *Saccharomyces cerevisiae* (NBRC1136).

SEQ ID NO: 6 is the amino acid sequence of HMGL derived from *Pseudomonas mevalonii*.

SEQ ID NO: 7 is the amino acid sequence of HMGL derived from *Pseudomonas putida* KT2440 (ATCC47054).

SEQ ID NO: 8 is the nucleotide sequence of 16S rDNA of *Pseudomonas* sp. 1-MV (FERN BP-11063).

SEQ ID NO: 9 is the nucleotide sequence of 16S rDNA of *Variovorax* sp. 5-MV (FERN BP-11064).

SEQ ID NO: 10 is the nucleotide sequence of 16S rDNA of *Delftia* sp. 12-MV (FERN BP-11065).

SEQ ID NO: 11 is the nucleotide sequence of 16S rDNA of *Comamonas* sp. 25-MV (FERN BP-11066).

SEQ ID NO: 12 is the nucleotide sequence of the HMGR gene derived from *Pseudomonas* sp. 1-MV (NBRC-11063).

SEQ ID NO: 13 is the nucleotide sequence of HMGR gene derived from *Pseudomonas mevalonii*.

SEQ ID NO: 14 is the nucleotide sequence of a forward primer for amplification of HMGR derived from *Pseudomonas* sp. 1-MV (FERM BP-11063).

SEQ ID NO: 15 is the nucleotide sequence of a reverse primer for amplification of HMGR derived from *Pseudomonas* sp. 1-MV (FERM BP-11063).

SEQ ID NO: 16 is the nucleotide sequence of a forward primer for amplification of HMGR derived from *Archaeoglobus fulgidus* (NBRC100126).

SEQ ID NO: 17 is the nucleotide sequence of a reverse primer for amplification of HMGR derived from *Archaeoglobus fulgidus* (NBRC100126).

SEQ ID NO: 18 is the nucleotide sequence of a forward primer for amplification of the first half of MVK derived from *Saccharomyces cerevisiae* (NBRC1136).

SEQ ID NO: 19 is the nucleotide sequence of a reverse primer for amplification of the first half of MVK derived from *Saccharomyces cerevisiae* (NBRC1136).

SEQ ID NO: 20 is the nucleotide sequence of a forward primer for amplification of the last half of MVK derived from *Saccharomyces cerevisiae* (NBRC1136).

SEQ ID NO: 21 is the nucleotide sequence of a reverse primer for amplification of the last half of MVK derived from *Saccharomyces cerevisiae* (NBRC1136).

SEQ ID NO: 22 is the nucleotide sequence of a forward primer for amplification of HMGL derived from *Pseudomonas putida* KT2440.

SEQ ID NO: 23 is the nucleotide sequence of a reverse primer for amplification of HMGL derived from *Pseudomonas putida* KT2440.

SEQ ID NO: 24 is the nucleotide sequence of POP promoter and a cloning site linked thereto.

SEQ ID NO: 25 is the N terminal amino acid sequence of HMGR derived from *Variovorax* sp. 5-MV (FERM BP-11064).

SEQ ID NO: 26 is the N terminal amino acid sequence of HMGR derived from *Delftia* sp. 12-MV (FERM BP-11065).

SEQ ID NO: 27 is the N terminal amino acid sequence of HMGR derived from *Comamonas* sp. 25-MV (FERM BP-11066).

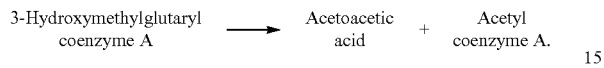

The invention claimed is:

1. A method for measuring a concentration of an analyte in a test solution wherein the analyte is i) mevalonic acid and/or 3-hydroxymethylglutaryl coenzyme A, or ii) coenzyme A, the method comprising the following steps (p) and (q):

(p) a step of allowing an enzyme that catalyzes a reaction represented by Reaction Formula 1':

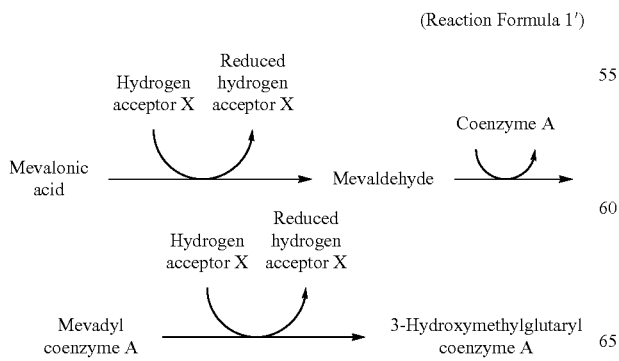

(Reaction Formula 1')

and an enzyme that catalyzes a reaction represented by Reaction Formula 2':

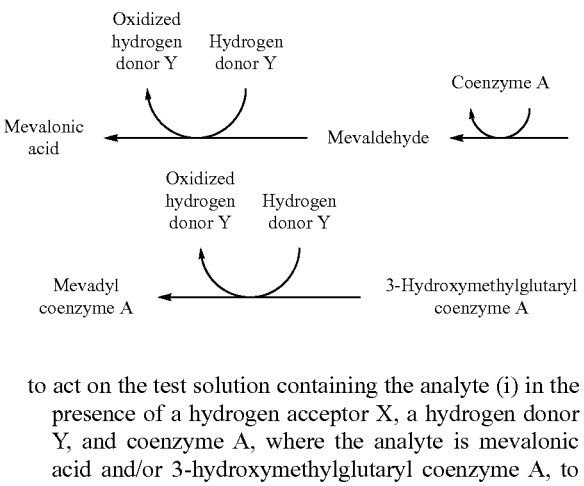

(Reaction Formula 2')

to act on the test solution containing the analyte (i) in the presence of a hydrogen acceptor X, a hydrogen donor Y, and coenzyme A, where the analyte is mevalonic acid and/or 3-hydroxymethylglutaryl coenzyme A, to produce both a reduced hydrogen acceptor X and an oxidized hydrogen donor Y, wherein the hydrogen donor Y and the reduced hydrogen acceptor X are not the same or (ii) in the presence of a hydrogen acceptor X, a hydrogen donor Y, and mevalonic acid, where the analyte is coenzyme A, to produce both a reduced hydrogen acceptor X and an oxidized hydrogen donor Y, wherein the hydrogen donor Y and the reduced hydrogen acceptor X are not the same; and (q) a step of measuring an amount of: a reduced hydrogen acceptor X that is produced; or an oxidized hydrogen donor Y that is produced; or a hydrogen acceptor X that is decreased; or a hydrogen donor Y that is decreased.

2. The method according to claim 1, wherein the concentration of the analyte is lower than 30 nM, and the step of measuring the amount of: the reduced hydrogen acceptor X that is produced; or the oxidized hydrogen donor Y that is produced; or the hydrogen acceptor X that is decreased; or the hydrogen donor Y that is decreased, is performed by a colorimetric analysis.

3. The method according to claim 1, wherein the hydrogen acceptor X is selected from a group of oxidized nicotinamide adenine dinucleotides.

4. The method according to claim 1, wherein the hydrogen donor Y is selected from a group of reduced nicotinamide adenine dinucleotides.

5. The method according to claim 3, wherein the oxidized nicotinamide adenine dinucleotides are selected from the group consisting of an oxidized nicotinamide adenine dinucleotide, an oxidized nicotinamide adenine dinucleotide phosphate, an oxidized thionicotinamide adenine dinucleotide, an oxidized thionicotinamide adenine dinucleotide phosphate, an oxidized acetyl nicotinamide adenine dinucleotide, and an oxidized acetyl nicotinamide adenine dinucleotide phosphate, and combinations thereof.

6. The method according to claim 4, wherein the reduced nicotinamide adenine dinucleotides are selected from the group consisting of a reduced nicotinamide adenine dinucleotide, a reduced nicotinamide adenine dinucleotide phosphate, reduced thionicotinamide adenine dinucleotide, a reduced thionicotinamide adenine dinucleotide phosphate, a reduced acetyl nicotinamide adenine dinucleotide, and a reduced acetyl nicotinamide adenine dinucleotide phosphate, and combinations thereof.

7. The method according to claim 1,
wherein the concentration of the analyte is lower than 100 nM;
the hydrogen acceptor X is an oxidized thionicotinamide adenine dinucleotide or an oxidized thionicotinamide adenine dinucleotide phosphate;
the hydrogen donor Y is a reduced nicotinamide adenine dinucleotide or a reduced nicotinamide adenine dinucleotide phosphate, and
the step of measuring the amount of: the reduced hydrogen acceptor X that is produced; or the oxidized hydrogen donor Y that is produced; or the hydrogen acceptor X that is decreased; or the hydrogen donor Y that is decreased, is performed by a colorimetric analysis.

8. The method according to claim 1, wherein the enzyme that catalyzes the reaction represented by Reaction Formula 1' is hydroxymethylglutaryl coenzyme A reductase.

9. The method according to claim 1, wherein the enzyme that catalyzes the reaction represented by Reaction Formula 2' is hydroxymethylglutaryl coenzyme A reductase.

10. The method according to claim 8, wherein the hydroxymethylglutaryl coenzyme A reductase is derived from the genus of *Pseudomonas, Variovorax, Delftia, Comamonas*, or *Archaeoglobus*.

11. The method according to claim 1, wherein the enzyme that catalyzes the reaction(s) represented by Reaction Formula 1' and/or Reaction Formula 2' is:
(i) a protein having an amino acid sequence represented by any of SEQ ID NOS: 1 to 3; or
(ii) a protein having an amino acid sequence which includes deletion, addition, and/or substitution of one or several amino acids in the amino acid sequence represented by any one of SEQ ID NOS: 1 to 3 and having an activity of catalyzing the reaction(s) represented by Reaction Formula 1' and/or Reaction Formula 2'.

12. The method according to claim 1, wherein the test solution contains mevalonic acid and 3-hydroxymethylglutaryl coenzyme A, the analyte is 3-hydroxymethylglutaryl coenzyme A, and the method further comprises the following step (o) before the step (p):
(o) a step of removing mevalonic acid from the test solution.

13. The method according to claim 12, wherein the step (o) is performed by an enzymatic reaction.

14. The method according to claim 13, wherein the enzymatic reaction is a mevalonate kinase reaction.

15. The method according to claim 12, wherein the step (o) is performed by a mevalonate kinase reaction, and then the step (p) is performed without performing an isolation procedure.

16. The method according to claim 15, wherein the mevalonate kinase is:
(i) a protein having an amino acid sequence encoded by a nucleotide sequence of SEQ ID NO: 5; or
(ii) a protein having an amino acid sequence which includes deletion, addition, and/or substitution one or several amino acids in the amino acid sequence encoded by a nucleotide sequence of SEQ ID NO: 5 and having an activity of catalyzing a reaction represented by Reaction Formula 21:

(Reaction Formula 21)

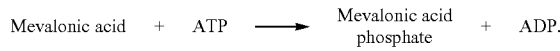

17. The method according to claim 1, wherein the test solution contains mevalonic acid and 3-hydroxymethylglutaryl coenzyme A, the analyte is mevalonic acid, and the method further comprises the following step (o') before the step (p):
(o') a step of removing 3-hydroxymethylglutaryl coenzyme A from the test solution.

18. The method according to claim 17, wherein the step (o') is performed by an enzymatic reaction.

19. The method according to claim 18, wherein the enzymatic reaction is a hydroxymethylglutaryl coenzyme A lyase reaction.

20. The method according to claim 17, wherein the step (o') is performed by a hydroxymethylglutaryl coenzyme A lyase reaction, and then the step (p) is performed without performing an isolation procedure.

21. The method according to claim 20, wherein the hydroxymethylglutaryl coenzyme A lyase is:
 (i) a protein having an amino acid sequence of SEQ ID NO: 7; or
 (ii) a protein having an amino acid sequence which includes deletion, addition, and/or substitution of one or several amino acids in the amino acid sequence of SEQ ID NO: 7 and having an activity of catalyzing a reaction represented by Reaction Formula 22

(Reaction Formula 22)

SEQUENCE LISTING

```
<160> NUMBER OF SEQ ID NOS: 27

<210> SEQ ID NO 1
<211> LENGTH: 428
<212> TYPE: PRT
<213> ORGANISM: Pseudomonas sp.

<400> SEQUENCE: 1
```

-continued

```
Met Ser Ile Asp Ser Arg Leu Pro Asn Phe Arg Ser Leu Ser Pro Val
1               5                   10                  15

Gln Arg Leu Glu His Leu Gln Gln Leu Leu Gln Leu Pro Ala Asp Asp
                20                  25                  30

Val Ala Leu Leu Arg Asp Ala Gly Ala Leu Pro Leu Asp Ile Ala Asp
            35                  40                  45

Gly Met Ile Glu Asn Val Ile Gly Lys Phe Glu Leu Pro Tyr Ala Val
        50                  55                  60

Ala Ser Asn Phe Gln Ile Asn Gly Arg Asp Val Val Pro Leu Val
65                  70                  75                  80

Val Glu Glu Pro Ser Val Val Ala Ala Ser Phe Met Ala Lys Leu
                85                  90                  95

Ala Arg Asp Ala Gly Gly Phe Met Thr Ser Ser Leu Pro Leu Met
            100                 105                 110

Arg Ala Gln Val Gln Ile Val Asp Ile Ala Asp Pro Tyr Asn Ala Arg
        115                 120                 125

Leu Ser Leu Met Arg Arg Lys Glu Glu Ile Ile Glu Leu Ala Asn Arg
    130                 135                 140

Lys Asp Gln Leu Leu Asn Lys Leu Gly Gly Cys Arg Asp Ile Glu
145                 150                 155                 160

Val His Thr Phe Ala Gln Ser Pro Arg Gly Pro Met Leu Val Ala His
            165                 170                 175

Leu Ile Val Asp Val Arg Asp Ala Met Gly Ala Asn Thr Val Asn Thr
        180                 185                 190

Met Ala Glu Ala Val Ala Pro Leu Met Glu Glu Ile Thr Gly Gly Lys
    195                 200                 205

Val Arg Leu Arg Ile Leu Ser Asn Leu Ala Asp Leu Arg Leu Ala Arg
210                 215                 220

Ala Gln Val Arg Ile Ala Pro Gln Leu Leu Thr Thr Ser Glu Tyr Lys
225                 230                 235                 240

Gly Glu Asp Val Ile Glu Gly Ile Leu Asp Ala Tyr Asn Phe Ala Val
            245                 250                 255

Val Asp Pro Tyr Arg Ala Ala Thr His Asn Lys Gly Ile Met Asn Gly
        260                 265                 270

Ile Asp Pro Leu Ile Val Ala Thr Gly Asn Asp Trp Arg Ala Val Glu
    275                 280                 285

Ala Gly Ala His Ala Tyr Ala Cys Arg Asp Gly His Tyr Gly Ser Leu
    290                 295                 300

Thr Thr Trp Glu Lys Asp Gly Asn Gly His Leu Val Gly Thr Leu Glu
305                 310                 315                 320

Met Pro Met Pro Val Gly Leu Val Gly Gly Ala Thr Lys Thr His Pro
            325                 330                 335

Leu Ala Gln Leu Ser Leu Arg Ile Leu Gly Val Lys Thr Ala Gln Glu
        340                 345                 350

Leu Ala Glu Ile Ala Val Ala Val Gly Leu Ala Gln Asn Leu Gly Ala
    355                 360                 365

Leu Arg Ala Leu Ser Thr Glu Gly Ile Gln Arg Gly His Met Ala Leu
370                 375                 380

His Ala Arg Asn Ile Ala Leu Ser Ala Gly Ala Arg Gly Glu Glu Val
385                 390                 395                 400

Asp Trp Leu Val Lys Arg Met Val Glu Ala Arg Asp Val Arg Ala Asp
            405                 410                 415
```

Asn Ala Ala Gln Leu Leu Lys Gln Lys Arg Ala Leu
            420                 425

<210> SEQ ID NO 2
<211> LENGTH: 428
<212> TYPE: PRT
<213> ORGANISM: Pseudomonas mevalonii

<400> SEQUENCE: 2

Met Ser Leu Asp Ser Arg Leu Pro Ala Phe Arg Asn Leu Ser Pro Ala
1               5                   10                  15

Ala Arg Leu Asp His Ile Gly Gln Leu Leu Gly Leu Ser His Asp Asp
            20                  25                  30

Val Ser Leu Leu Ala Asn Ala Gly Ala Leu Pro Met Asp Ile Ala Asn
        35                  40                  45

Gly Met Ile Glu Asn Val Ile Gly Thr Phe Glu Leu Pro Tyr Ala Val
    50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ser Tyr Met Ala Lys Leu
            85                  90                  95

Ala Arg Ala Asn Gly Gly Phe Thr Thr Ser Ser Ala Pro Leu Met
            100                 105                 110

His Ala Gln Val Gln Ile Val Gly Ile Gln Asp Pro Leu Asn Ala Arg
            115                 120                 125

Leu Ser Leu Leu Arg Arg Lys Asp Glu Ile Ile Glu Leu Ala Asn Arg
    130                 135                 140

Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175

Leu Ile Val Asp Val Arg Asp Ala Met Gly Ala Asn Thr Val Asn Thr
            180                 185                 190

Met Ala Glu Ala Val Ala Pro Leu Met Glu Ala Ile Thr Gly Gly Gln
    195                 200                 205

Val Arg Leu Arg Ile Leu Ser Asn Leu Ala Asp Leu Arg Leu Ala Arg
210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
            260                 265                 270

Ile Asp Pro Leu Ile Val Ala Thr Gly Asn Asp Trp Arg Ala Val Glu
    275                 280                 285

Ala Gly Ala His Ala Tyr Ala Cys Arg Ser Gly His Tyr Gly Ser Leu
290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
            340                 345                 350

Leu Ala Glu Ile Ala Val Ala Val Gly Leu Ala Gln Asn Leu Gly Ala
    355                 360                 365

```
Met Arg Ala Leu Ala Thr Glu Gly Ile Gln Arg Gly His Met Ala Leu
        370                 375                 380

His Ala Arg Asn Ile Ala Val Val Ala Gly Ala Arg Gly Asp Glu Val
385                 390                 395                 400

Asp Trp Val Ala Arg Gln Leu Val Glu Tyr His Asp Val Arg Ala Asp
                405                 410                 415

Arg Ala Val Ala Leu Leu Lys Gln Lys Arg Gly Gln
            420                 425

<210> SEQ ID NO 3
<211> LENGTH: 436
<212> TYPE: PRT
<213> ORGANISM: Archaeoglobus fulgidus

<400> SEQUENCE: 3

Met Gln Val Leu Arg Leu Asp Arg Arg His Tyr Lys Ser Gly Lys Ile
1               5                   10                  15

Arg Arg Ala Met Ser Ser Arg Ile Pro Gly Phe Tyr Lys Leu Ser Val
            20                  25                  30

Glu Glu Arg Leu Lys Lys Val Ala Glu Phe Ala Gly Leu Ser Asp Glu
        35                  40                  45

Glu Val Lys Ala Val Leu Ser Gln Gly Leu Pro Leu Asp Val Ala Asp
    50                  55                  60

Arg Met Ile Glu Asn Val Ile Gly Thr Phe Glu Leu Pro Leu Gly Ile
65                  70                  75                  80

Ala Thr Asn Phe Leu Ile Asp Gly Lys Asp Tyr Leu Ile Pro Met Ala
                85                  90                  95

Ile Glu Glu Pro Ser Val Val Ala Ala Ser Asn Ala Ala Arg Met
            100                 105                 110

Ala Arg Glu Ser Gly Gly Phe Thr Thr Asp Tyr Thr Gly Ser Leu Met
        115                 120                 125

Ile Gly Gln Ile Gln Val Thr Lys Leu Leu Asn Pro Asn Ala Ala Lys
    130                 135                 140

Phe Glu Val Leu Arg Gln Lys Asp Glu Ile Ile Glu Arg Ala Asn Glu
145                 150                 155                 160

Cys Asp Pro Met Leu Val Asn Leu Gly Gly Cys Lys Asp Ile Glu
                165                 170                 175

Ala Arg Val Ile Asp Thr Ile Met Gly Lys Met Leu Ile Val His Leu
            180                 185                 190

Ile Val Asp Val Lys Asp Ala Met Gly Ala Asn Ala Val Asn Thr Met
        195                 200                 205

Cys Glu Lys Val Ala Pro Phe Ile Glu Arg Ile Thr Gly Gly Lys Val
    210                 215                 220

Tyr Leu Arg Ile Ile Ser Asn Leu Ala Ala Tyr Arg Leu Ala Arg Ala
225                 230                 235                 240

Lys Ala Val Phe Asp Lys Asp Val Ile Gly Gly Glu Val Val Glu
                245                 250                 255

Gly Ile Met Leu Ala Tyr Ala Phe Ala Ala Asp Pro Phe Arg Cys
            260                 265                 270

Ala Thr His Asn Lys Gly Ile Met Asn Gly Ile Ser Ala Leu Met Ile
        275                 280                 285

Ala Thr Gly Asn Asp Phe Arg Ala Ile Glu Ala Gly Ala His Ser Tyr
    290                 295                 300

Ala Ala Ile Gly Gly Tyr Lys Pro Leu Thr Thr Tyr Glu Val Asp Arg
```

```
                305                 310                 315                 320
Lys Gly Asn Leu Val Gly Thr Ile Glu Ile Pro Met Ala Val Gly Val
                325                 330                 335

Ile Gly Gly Ala Thr Lys Val Asn Pro Leu Ala Lys Ile Ser Leu Lys
                340                 345                 350

Ile Leu Gly Val Asn Thr Ala Glu Glu Leu Ala Arg Val Ala Ala Ala
                355                 360                 365

Leu Gly Leu Ala Gln Asn Phe Ala Ala Leu Arg Ala Leu Ala Thr Glu
        370                 375                 380

Gly Ile Gln Arg Gly His Met Glu Leu His Ala Arg Asn Leu Ala Ile
385                 390                 395                 400

Met Ala Gly Ala Thr Gly Asp Glu Val Asp Arg Val Val Glu Ile Met
                405                 410                 415

Val Arg Asp Gly Lys Ile Arg Leu Asp Tyr Ala Lys Glu Val Leu Glu
                420                 425                 430

Arg Leu Arg Ser
        435

<210> SEQ ID NO 4
<211> LENGTH: 202
<212> TYPE: DNA
<213> ORGANISM: Aerococcus viridans

<400> SEQUENCE: 4
aaaagttctt gatttataag ggtttctgga cttcttactg tactagtaca atttcgcccc      60
ttgtaccatt tttctgatac agaaacaata ttgtactgaa aaaagggtat ttttggctaa    120
ttatggacct cacaaaggat atttgtggca attcattgga ataagctgtt ttaagtgcta    180
ttatttcaat tgtgatattt tt                                              202

<210> SEQ ID NO 5
<211> LENGTH: 1332
<212> TYPE: DNA
<213> ORGANISM: Saccharomyces cerevisiae

<400> SEQUENCE: 5
atgtcattac cgttcttaac ttctgcaccg ggaaaggtta ttattttttgg tgaacactct     60 gctgtgtaca caagcctgc cgtcgctgct agtgtgtctg cgttgagaac ctacctgcta    120
ataagcgagt catctgcacc agatactatt gaattggact cccggacat agctttaat     180 cataagtggt ccatcaatga tttcaatgcc atcaccgagg atcaagtaaa ctcccaaaaa    240
ttggccaagg ctcaacaagc caccgatggc ttgtctcagg aactcgttag tcttttggat    300
ccgttgttag ctcaactatc cgaatccttc cactaccatg cagcgttttg tttcctgtat    360
atgtttgttt gcctatgccc ccatgccaag aatattaagt tttctttaaa gtctacttta    420
cccatcggtg ctgggttggg ctcaagcgcc tctatttctg tatcactggc cttagctatg    480
gcctacttgg gggggttaat aggatctaat gacttggaaa agctgtcaga aaacgataag    540
catatagtga atcaatgggc cttcataggt gaaaagtgta ttcacggtac cccttcagga    600
atagataacg ctgtggccac ttatggtaat gccctgctat ttgaaaaaga ctcacataat    660
ggaacaataa acacaaacaa ttttaagttc ttagatgatt cccagccat tccaatgatc    720 ctaacctata ctagaattcc aaggtctaca aaagatcttg ttgctcgcgt tcgtgtgttg    780
gtcaccgaga aatttcctga agttatgaag ccaattcttg atgccatggg tgaatgtgcc    840
ctacaaggct tagatcat gactaagtta agtaaatgta aggcaccga tgacgaggct    900
```

-continued

```
gtagaaacta ataatgaact gtatgaacaa ctattggaat tgataagaat aaatcatgga    960
ctgcttgtct caatcggtgt ttctcatcct ggattagaac ttattaaaaa tctgagcgat   1020
gatttgagaa ttggctccac aaaacttacc ggtgctggtg gcggcggttg ctctttgact   1080
ttgttacgaa gagacattac tcaagagcaa attgacagct tcaaaaagaa attgcaagat   1140
gattttagtt acgagacatt tgaaacagac ttgggtggga ctggctgctg tttgttaagc   1200
gcaaaaaatt tgaataaaga tcttaaaatc aaatccctag tattccaatt atttgaaaat   1260
aaaactacca caaagcaaca aattgacgat ctattattgc caggaaacac gaatttacca   1320
tggacttcat aa                                                      1332
```

<210> SEQ ID NO 6
<211> LENGTH: 301
<212> TYPE: PRT
<213> ORGANISM: Pseudomonas mevalonii

<400> SEQUENCE: 6

```
Met Gln Ala Val Lys Val Phe Glu Val Gly Pro Arg Asp Gly Leu Gln
1               5                   10                  15
Asn Glu Arg Gln Pro Leu Ser Val Ala Ala Arg Val Gly Leu Ile Gly
            20                  25                  30
Glu Leu Ala Gly Thr Gly Leu Arg His Ile Glu Ala Gly Ala Phe Val
        35                  40                  45
Ser Pro Arg Trp Val Pro Gln Met Ala Gly Ser Asp Glu Val Leu Arg
    50                  55                  60
Gln Leu Pro Ser Asn Asp Gly Val Ser Tyr Thr Ala Leu Val Pro Asn
65                  70                  75                  80
Arg Gln Gly Phe Glu Ala Ala Gln Arg Ala Gly Cys Arg Glu Val Ala
                85                  90                  95
Val Phe Ala Ala Ala Ser Glu Ala Phe Ser Arg Asn Asn Ile Asn Cys
            100                 105                 110
Ser Ile Asp Glu Ser Phe Glu Arg Phe Thr Pro Val Leu Arg Ala Ala
        115                 120                 125
Asn Glu Ala Ser Ile Arg Val Arg Gly Tyr Val Ser Cys Val Leu Gly
    130                 135                 140
Cys Pro Phe Ser Gly Ala Val Ala Pro Glu Ala Val Ala Lys Val Ala
145                 150                 155                 160
Arg Arg Leu Tyr Glu Leu Gly Cys Tyr Glu Ile Ser Leu Gly Asp Thr
                165                 170                 175
Ile Gly Ala Gly Arg Pro Asp Glu Thr Ala Gln Leu Phe Glu Leu Cys
            180                 185                 190
Ala Arg Gln Leu Pro Val Ala Ala Leu Ala Gly His Phe His Asp Thr
        195                 200                 205
Trp Gly Met Ala Ile Ala Asn Val His Ala Ala Leu Ala Gln Gly Val
    210                 215                 220
Arg Thr Phe Asp Ser Ser Val Ala Gly Leu Gly Gly Cys Pro Tyr Ser
225                 230                 235                 240
Pro Gly Ala Ser Gly Asn Val Ala Thr Glu Asp Leu Leu Tyr Leu Leu
                245                 250                 255
His Gly Leu Gly Tyr Ser Thr Gly Val Asp Leu Glu Ala Val Ala Gln
            260                 265                 270
Val Gly Val Arg Ile Ser Ala Gln Leu Gly Thr Ala Asn Arg Ser Arg
        275                 280                 285
```

Ala Gly Leu Ala Leu Ala Ala Arg Ser Ala Arg Glu His
    290                 295                 300

<210> SEQ ID NO 7
<211> LENGTH: 299
<212> TYPE: PRT
<213> ORGANISM: Pseudomonas putida

<400> SEQUENCE: 7

Met Ser Leu Pro Lys His Val Arg Leu Glu Val Gly Pro Arg Asp
1               5                   10                  15

Gly Leu Gln Asn Glu Ala Gln Pro Ile Ser Val Ala Asp Lys Val Arg
                20                  25                  30

Leu Val Asn Asp Leu Thr Glu Ala Gly Leu Ala Tyr Ile Glu Val Gly
            35                  40                  45

Ser Phe Val Ser Pro Lys Trp Val Pro Gln Met Ala Gly Ser Ala Glu
    50                  55                  60

Val Phe Ala Gly Ile Gln Gln Arg Pro Gly Val Thr Tyr Ala Ala Leu
65                  70                  75                  80

Ala Pro Asn Leu Arg Gly Phe Glu Asp Ala Leu Ala Ala Gly Val Lys
                85                  90                  95

Glu Val Ala Val Phe Ala Ala Ala Ser Glu Ala Phe Ser Gln Arg Asn
                100                 105                 110

Ile Asn Cys Ser Ile Ser Glu Ser Leu Lys Arg Phe Glu Pro Ile Met
            115                 120                 125

Asp Ala Ala Arg Ser His Gly Met Arg Val Arg Gly Tyr Val Ser Cys
    130                 135                 140

Val Leu Gly Cys Pro Tyr Glu Gly Lys Val Ser Ala Glu Gln Val Ala
145                 150                 155                 160

Pro Val Ala Arg Ala Leu His Asp Met Gly Cys Tyr Glu Val Ser Leu
                165                 170                 175

Gly Asp Thr Ile Gly Thr Gly Thr Ala Gly Asp Thr Arg Arg Leu Phe
            180                 185                 190

Glu Val Val Ser Ala Gln Val Pro Arg Glu Gln Leu Ala Gly His Phe
    195                 200                 205

His Asp Thr Tyr Gly Gln Ala Leu Ala Asn Val Tyr Ala Ser Leu Leu
    210                 215                 220

Glu Gly Ile Ser Val Phe Asp Ser Ser Val Ala Gly Leu Gly Gly Cys
225                 230                 235                 240

Pro Tyr Ala Lys Gly Ala Thr Gly Asn Ile Ala Ser Glu Asp Val Val
                245                 250                 255

Tyr Leu Leu Gln Gly Leu Gly Ile Glu Thr Gly Ile Asp Leu Gly Leu
            260                 265                 270

Leu Ile Ala Ala Gly Gln Arg Ile Ser Gly Val Leu Gly Arg Asp Asn
    275                 280                 285

Gly Ser Arg Val Ala Arg Ala Cys Ser Ala Gln
    290                 295

<210> SEQ ID NO 8
<211> LENGTH: 1528
<212> TYPE: DNA
<213> ORGANISM: Pseudomonas sp.

<400> SEQUENCE: 8
gagtttgatc ctggctcaga ttgaacgctg gcggcaggcc taacacatgc aagtcgagcg      60
gtagagaraa gcttgctttyt cttgagagcg gcggacgggt gagtaatgcc taggaatctg     120

```
cctggtagtg ggggataacg tccggaaacg gacgctaata ccgcatacgt cctacgggag      180
aaagcagggg accttcgggc cttgcgctat cagatgagcc taggtcggat tagctagttg      240
gtgaggtaat ggctcaccaa ggcgacgatc cgtaactggt ctgagaggat gatcagtcac      300
actggaactg agacacggtc cagactccta cgggaggcag cagtggggaa tattggacaa      360
tgggcgaaag cctgatccag ccatgccgcg tgtgtgaaga aggtcttcgg attgtaaagc      420
actttaagtt ggggaggaagg gcagtaagtt aataccttgc tgttttgacg ttaccgacag      480
aataagcacc ggctaactct gtgccagcag ccgcggtaat acagagggtg caagcgttaa      540
tcggaattac tgggcgtaaa gcgcgcgtag gtggtttgtt aagttggatg tgaaagcccc      600
gggctcaacc tgggaactgc attcaaaact gacaagctag agtatggtag agggtggtgg      660
aatttcctgt gtagcggtga atgcgtaga tataggaagg aacaccagtg gcgaaggcga      720
ccacctggac tgatactgac actgaggtgc gaaagcgtgg ggagcaaaca ggattagata      780
ccctggtagt ccacgccgta aacgatgtca actagccgtt ggggaccttg agtctttagt      840
ggcgcagcta acgcattaag ttgaccgcct ggggagtacg gccgcaaggt taaaactcaa      900
atgaattgac gggggcccgc acaagcggtg gagcatgtgg tttaattcga agcaacgcga      960
agaaccttac caggccttga catccaatga actttccaga gatggattgg tgccttcggg     1020
agcattgaga caggtgctgc atggctgtcg tcagctcgtg tcgtgagatg ttgggttaag     1080
tcccgtaacg agcgcaaccc ttgtccttag ttaccagcac gttatggtgg gcactctaag     1140
gagactgccg gtgacaaacc ggaggaaggt ggggatgacg tcaagtcatc atggccctta     1200
cggcctgggc tacacacgtg ctacaatggt cggtacagag ggttgccaag ccgcgaggtg     1260
gagctaatcc cacaaaaccg atcgtagtcc ggatcgcagt ctgcaactcg actgcgtgaa     1320
gtcggaatcg ctagtaatcg cgaatcagaa tgtcgcggtg aatacgttcc cgggccttgt     1380
acacaccgcc cgtcacacca tgggagtggg ttgcaccaga agtagctagt ctaaccttcg     1440
ggaggacggt taccacggtg tgattcatga ctggggtgaa gtcgtaacaa ggtagccgta     1500
ggggaacctg cggctggatc acctcctt                                        1528
```

<210> SEQ ID NO 9
<211> LENGTH: 1526
<212> TYPE: DNA
<213> ORGANISM: Variovorax sp.

<400> SEQUENCE: 9

```
gagtttgatc ctggctcaga ttgaacgctg gcggcatgcc ttacacatgc aagtcgaacg       60
gcagcgcggg agcaatcctg gcggcgagtg gcgaacgggt gagtaataca tcggaacgtg      120
cccaatcgtg ggggataacg cagcgaaagc tgtgctaata ccgcatacga tctacggatg      180
aaagcagggg accgcaaggc cttgcgcgaa tggagcggcc gatggcagat taggtagttg      240
gtgaggtaaa ggctcaccaa gccttcgatc tgtagctggt ctgagaggac gaccagccac      300
actgggactg agacacggcc cagactccta cgggaggcag cagtggggaa ttttggacaa      360
tgggcgcaag cctgatccag ccatgccgcg tgcaggatga aggccttcgg gttgtaaact      420
gcttttgtac ggaacgaaac ggccttttct aataaagagg ctaatgacg gtaccgtaag      480 aataagcacc ggctaactac gtgccagcag ccgcggtaat acgtagggtg caagcgttaa      540
tcggaattac tgggcgtaaa gcgtgcgcag gcggtgatgt aagacagttg tgaaatcccc      600
gggctcaacc tgggaactgc atctgtgact gcatcgctgg agtacggcag aggggatgg      660
```

```
aattccgcgt gtagcagtga aatgcgtaga tatgcggagg aacaccgatg gcgaaggcaa      720 tccectgggc ctgtactgac gctcatgcac gaaagcgtgg ggagcaaaca ggattagata      780
ccctggtagt ccacgcccta acgatgtca  actggttgtt gggtcttcac tgactcagta      840
acgaagctaa cgcgtgaagt tgaccgcctg ggagtacgg  ccgcaaggtt gaaactcaaa      900
ggaattgacg gggacccgca caagcggtgg atgatgtggt ttaattcgat gcaacgcgaa      960
aaaccttacc cacctttgac atgtacggaa tttgccagag atggcttagt gctcgaaaga     1020
gagccgtaac acaggtgctg catggctgtc gtcagctcgt gtcgtgagat gttgggttaa     1080
gtcccgcaac gagcgcaacc cttgtcatta gttgctacat tcagttgggc actctaatga     1140
gactgccggt gacaaaccgg aggaaggtgg ggatgacgtc aagtcctcat ggcccttata     1200 ggtgggcta  cacacgtcat acaatggctg gtacaaaggg ttgccaaccc gcgaggggga     1260
gctaatccca taaaaccagt cgtagtccgg atcgcagtct gcaactcgac tgcgtgaagt     1320
cggaatcgct agtaatcgtg gatcagaatg tcacggtgaa tacgttcccg ggtcttgtac     1380
acaccgcccg tcacaccatg ggagcgggtt ctgccagaag tagttagctt aaccgcaagg     1440
agggcgatta ccacggcagg gttcgtgact ggggtgaagt cgtaacaagg tagccgtatc     1500
ggaaggtgcg gctggatcac ctcctt                                          1526

<210> SEQ ID NO 10
<211> LENGTH: 1524
<212> TYPE: DNA
<213> ORGANISM: Delftia sp.

<400> SEQUENCE: 10
gagtttgatc ctggctcaga ttgaacgctg gcggcatgcc ttacacatgc aagtcgaacg       60
gtaacaggtc ttcggacgct gacgagtggc gaacgggtga gtaatacatc ggaacgtgcc      120
cagtcgtggg ggataactac tcgaaagagt agctaatacc gcatacgatc tgaggatgaa      180 agcggggac  cttcgggcct cgcgcgattg agcggccga  tggcagatta ggtagttggt      240
gggataaaag cttaccaagc cgacgatctg tagctggtct gagaggacga ccagccacac      300
tgggactgag acacggccca gactcctacg ggaggcagca gtggggaatt ttggacaatg      360
ggcgaaagcc tgatccagca atgccgcgtg caggatgaag gccttcgggt tgtaaactgc      420 tttttgtacgg aacgaaaaag cttctcctaa tacgagaggc ccatgacggt accgtaagaa     480
taagcaccgg ctaactacgt gccagcagcc gcggtaatac gtagggtgcg agcgttaatc      540
ggaattactg ggcgtaaagc gtgcgcaggc ggttatgtaa  acagatgtg aaatccccgg      600 gctcaacctg gaactgcat  ttgtgactgc atggctagag tacggtagag ggggatggaa      660
ttccgcgtgt agcagtgaaa tgcgtagata tgcggaggaa caccgatggc gaaggcaatc      720
ccctggacct gtactgacgc tcatgcacga aagcgtgggg agcaaacagg attagatacc      780
ctggtagtcc acgccctaaa cgatgtcaac tggttgttgg gaattagttt tctcagtaac      840
gaagctaacg cgtgaagttg accgcctggg gagtacggcc gcaaggttga aactcaaagg      900
aattgacggg acccgcaca  agcggtggat gatgtggttt aattcgatgc aacgcgaaaa      960
accttaccca cctttgacat ggcaggaagt tccagagatg gattcgtgc  tcgaaagaga     1020 acctgcacac aggtgctgca tggctgtcgt cagctcgtgt cgtgagatgt tgggttaagt     1080
cccgcaacga gcgcaaccct tgtcattagt tgctacattt agttgggcac tctaatgaga     1140
ctgccggtga caaaccggag gaaggtgggg atgacgtcaa gtcctcatgg cccttatagg     1200
tggggctaca cacgtcatac aatggctggt acagagggtt gccaaccgc  gaggggagc      1260
```

```
taatcccata aaaccagtcg tagtccggat cgcagtctgc aactcgactg cgtgaagtcg    1320
gaatcgctag taatcgcgga tcagcatgcc gcggtgaata cgttcccggg tcttgtacac    1380
accgcccgtc acaccatggg agcgggtctc gccagaagta ggtagcctaa ccgcaaggag    1440
ggcgcttacc acggcggggt tcgtgactgg ggtgaagtcg taacaaggta gccgtatcgg    1500
aaggtgcggc tggatcacct cctt                                          1524
```

<210> SEQ ID NO 11
<211> LENGTH: 1524
<212> TYPE: DNA
<213> ORGANISM: Comamonas sp.

<400> SEQUENCE: 11

```
gagtttgatc ctggctcaga ttgaacgctg gcggcatgct ttacacatgc aagtcgaacg      60
gtaacaggtc ttcggatgct gacgagtggc gaacgggtga gtaatacatc ggaacgtgcc     120
tagtagtggg ggataactac tcgaaagagt agctaatacc gcatgagatc tacgatgaa     180 agcaggggac cttcgggcct tgtgctacta gagcggctga tggcagatta ggtagttggt     240
ggggtaaagg cttaccaagc ctgcgatctg tagctggtct gagaggacga ccagccacac     300
tgggactgag acacggccca gactcctacg ggaggcagca gtggggaatt ttggacaatg     360
ggcgaaagcc tgatccagca atgccgcgtg caggatgaag ccctcgggt tgtaaactgc     420 ttttgtacgg aacgaaaagc ctggggctaa tatccccggg tcatgacggt accgtaagaa     480
taagcaccgg ctaactacgt gccagcagcc gcggtaatac gtagggtgca agcgttaatc     540
ggaattactg ggcgtaaagc gtgcgcaggc ggttttgtaa cagtggtg aaatccccgg      600 gctcaacctg gaactgcca ttgtgactgc aaggctagag tgcggcagag ggggatggaa      660
ttccgcgtgt agcagtgaaa tgcgtagata tgcggaggaa caccgatggc gaaggcaatc    720
ccctgggcct gcactgacgc tcatgcacga aagcgtgggg agcaaacagg attagatacc    780
ctggtagtcc acgccctaaa cgatgtcaac tggttgttgg gtcttaactg actcagtaac    840
gaagctaacg cgtgaagttg accgcctggg gagtacggcc gcaaggttga aactcaaagg    900
aattgacggg gacccgcaca agcggtggat gatgtggttt aattcgatgc aacgcgaaaa    960
accttaccca cctttgacat ggcaggaact taccagagat ggtttggtgc tcgaaagaga   1020
acctgcacac aggtgctgca tggctgtcgt cagctcgtgt cgtgagatgt tgggttaagt   1080
cccgcaacga gcgcaaccct tgccattagt tgctacattc agttgagcac tctaatggga   1140
ctgccggtga caaccggag gaaggtgggg atgacgtcaa gtcctcatgg cccttatagg    1200
tggggctaca cacgtcatac aatggctggt acaaagggtt gccaacccgc gaggggagc    1260 taatcccata aagccagtcg tagtccggat cgcagtctgc aactcgactg cgtgaagtcg   1320
gaatcgctag taatcgtgga tcagaatgtc acggtgaata cgttcccggg tcttgtacac   1380
accgcccgtc acaccatggg agcgggtctc gccagaagta ggtagcctaa ccgcaaggag   1440
ggcgcttacc acggcggggt tcgtgactgg ggtgaagtcg taacaaggta gccgtatcgg   1500
aaggtgcggc tggatcacct cctt                                         1524
```

<210> SEQ ID NO 12
<211> LENGTH: 1287
<212> TYPE: DNA
<213> ORGANISM: Pseudomonas sp.

<400> SEQUENCE: 12

```
atgagtatcg attcgcgcct tccgaatttc gcagcctgt ccctgtcca gcgcctcgag    60 cacctgcaac aactgctgca attacccgcc gatgacgtcg ccctgctgcg tgatgctggc   120
gccctgccgc tggacatcgc cgacggcatg atcgagaacg taatcggcaa gttcgaactg   180
ccttacgcgg tggccagcaa cttccagatc aatggccgcg acgtggtcgt gccgctggtg   240
gtcgaggaac cctcggtggt cgccgccgcg tcgttcatgg ccaagctggc gcgcgatgct   300
ggcggcttca tgacctccag cagcctgccg ctgatgcgcg cccaggtgca gatcgtcgac   360
atcgccgacc cgtacaacgc cgcctgagc ctgatgcgcc gcaaggaaga gatcatcgaa   420
ctggccaacc gcaaggacca gttgctcaac aaactcggcg cggctgccg ggacatcgaa   480 gtccacacct tcgcccagag cccacggggg ccgatgctgg tggcgcacct gatcgtcgac   540
gtgcgcgatg ccatgggcgc caacacggtc aacaccatgg ccgaagccgt ggcgccgttg   600
atggaagaaa tcacgggcgg caaggtgcgt ctgcggatcc tatcgaacct ggccgacctg   660
cgcctggccc gggcccaggt gcgcattgcc ccgcagctgc tgaccacttc gaatacaag    720 ggcgaagacg tgatcgaggg cattctcgat gcctacaact ttgccgtggt cgaccgtac   780 cgcgccgcca cccacaacaa gggcatcatg aacggcatcg acccgctgat cgtcgccacc   840
ggcaacgact ggcgcgccgt ggaagccggg gcccacgcct atgcctgtcg cgatgggcac   900
tatggctcgc tgaccaccctg ggagaaggac ggcaacggcc acctggtcgg cacctggaa   960 atgcccatgc cggtcggcct ggtcggtggc gccaccaaga cccacccgct ggcgcaactg  1020
tcgctgcgca tcctcggtgt gaagaccgcc caggaactgg cggaaatcgc cgtggccgtg  1080
ggcctggcgc agaacctcgg cgcactgcgg gcgctgtcca ccgaaggcat ccagcgtggg  1140
cacatggcgc tgcacgcacg caacatcgcc ctgtcggccg ggcccgcgg cgaggaagtc  1200 gattggctgg tcaagcgcat ggtcgaggcc cgcgacgtgc gcgctgacaa cgccgcgcaa  1260
ctgctcaagc aaaagcgcgc gctgtga                                      1287
```

<210> SEQ ID NO 13
<211> LENGTH: 1287
<212> TYPE: DNA
<213> ORGANISM: Pseudomonas mevalonii

<400> SEQUENCE: 13

```
atgagcctcg attcccgcct gcccgctttc cgtaacctgt ccctgccgc gcgcctggac    60 cacatcggcc agttgctcgg cctgagccac gacgatgtca gcctgctggc caacgccggt   120
gccctgccga tggacatcgc caacggcatg atcgaaaacg tcatcggcac cttcgagctg   180
ccctatgccg tggccagcaa cttccagatc aatggccgtg atgtgctggt gccgctggtg   240
gtggaagagc cctcgatcgt cgccgctgct tcgtacatgg ccaagctggc ccgtgccaac   300
ggcggcttca ccacctccag cagcgccccg ctgatgcatg cccaggtaca gatcgtcggc   360
atacaggacc cgctcaatgc acgcctgagc ctgctgcgcc gcaaagacga aatcattgaa   420
ctggccaacc gcaaggacca gttgctcaac agcctcggcg cggctgccg cgacatcgaa   480 gtgcacacct tcgccgatac cccgcgtggc ccgatgctgg tggcgcacct gatcgtcgat   540
gtacgcgatg ccatgggcgc caacaccgtc aataccatgg ccgaggccgt tgcgccgctg   600
atggaagcca tcaccggggg ccaggtacgc ctgcgcattc tgtccaacct ggccgacctg   660
cgcctggcca gggcccaggt gcggattact ccgcagcaac tggaaacggc cgaattcagt   720
ggcgaggcag tgatcgaagg catcctcgac gcctacgcct cgctgcggt cgaccettac   780 cgcgcggcca cccacaacaa gggcatcatg aatggcatcg acccactgat cgtcgccact   840
```

```
ggcaacgact ggcgtgcagt ggaagccggc gcccatgcgt atgcctgccg cagtggtcac    900
tacggctcgc tgaccacctg ggaaaaggac aacaacggcc atttggtcgg caccctggaa    960
atgccgatgc ccgtaggcct ggtcggcggc gccaccaaaa cccatccgct ggcgcaactg   1020
tcgctgcgca tcctcggcgt gaaaacagcc caggcgctcg ctgagattgc cgtggccgta   1080
ggcctggcgc aaaacctcgg ggccatgcgc gccctggcca ccgaaggcat ccagcgcggc   1140
cacatggccc tgcatgcgcg caatattgcc gtggtggcgg gcgcccgagg cgatgaggtg   1200
gactgggttg cccggcagtt ggtggaatac cacgacgtgc gcgccgaccg cgccgtagca   1260
ctgctgaaac aaaagcgcgg ccaatga                                       1287
```

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer (FW) for amplifying HMGR derived from
      Pseudomonas sp.

<400> SEQUENCE: 14

```
ggctctagag gaataacacc atgagtatcg attcgcgcct                            40
```

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer (RV) for amplifying HMGR derived from
      Pseudomonas sp.

<400> SEQUENCE: 15

```
ggcgagctct cacagcgcgc gcttttgctt gagcag                                36
```

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer (FW) for amplifying HMGR derived from
      Archaeoglobus flugidus

<400> SEQUENCE: 16

```
ggtctagagg aataacacca tgcaggttct tagactcgac                            40
```

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer (RV) for amplifying HMGR derived from
      Archaeoglobus flugidus flugidus

<400> SEQUENCE: 17

```
ccgagctctc agcttcttaa cctctccaga acctccttg                             39
```

<210> SEQ ID NO 18
<211> LENGTH: 48
<212> TYPE: DNA
<213> ORGANISM: Artificial Sequence
<220> FEATURE:

<223> OTHER INFORMATION: Description of Artificial Sequence: Synthetic
primer (FW) for amplifying anterior half of MVK
derived from Saccharomyces cerevisiae

<400> SEQUENCE: 18
ggctctagag gaataacacc atgtcattac cgttcttaac ttctgcac        48

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
primer (RV) for amplifying anterior half of MVK
derived from Saccharomyces cerevisiae

<400> SEQUENCE: 19
cacccatggc atcaagaatt ggcttcat        28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
primer (FW) for amplifying posterior half of
MVK derived from Saccharomyces cerevisiae

<400> SEQUENCE: 20
atgaagccaa ttcttgatgc catgggtg        28

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
primer (RV) for amplifying posterior half of
MVK derived from Saccharomyces cerevisiae

<400> SEQUENCE: 21
ggcgagctct tatgaagtcc atggtaaatt cgtgtttcc        39

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
primer (FW) for amplifying HMGL derived from
Pseudomonas putida

<400> SEQUENCE: 22
ggctctagag gaataacacc atgtccttgc ccaaacacgt ccgcc        45

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
primer (RV) for amplifying HMGL derived from
Pseudomonas putida

<400> SEQUENCE: 23
ggcgagctcc tattgtgcgc tgcacgcccg tgctacccg        39

```
<210> SEQ ID NO 24
<211> LENGTH: 294
<212> TYPE: DNA
<213> ORGANISM: Artificial Sequence
<220> FEATURE:
<223> OTHER INFORMATION: Description of Artificial Sequence: Synthetic
      POP promoter polynucleotide flanked with artificial
      cloning sites

<400> SEQUENCE: 24
aagcttgggc tgcaggtcga aaaagttctt gatttataag ggtttctgga cttcttactg      60
tactagtaca atttcgcccc ttgtaccatt tttctgatac agaaacaata ttgtactgaa     120
aaaagggtat ttttggctaa ttatggacct cacaaaggat atttgtggca attcattgga     180
ataagctgtt ttaagtgcta ttatttcaat tgtgatattt tttcgactct agaggaataa     240
caccatggcc gtcgacgcta gcatgcatgg atcccgggta ccgagctcga attc           294

<210> SEQ ID NO 25
<211> LENGTH: 36
<212> TYPE: PRT
<213> ORGANISM: Variovorax sp.
<220> FEATURE:
<221> NAME/KEY: MUTAGEN
<222> LOCATION: (1)..(1)
<223> OTHER INFORMATION: Met or Val
<220> FEATURE:
<221> NAME/KEY: MUTAGEN
<222> LOCATION: (3)..(3)
<223> OTHER INFORMATION: Any amino acid

<400> SEQUENCE: 25

Xaa Ala Xaa Ser Arg Ile Pro Asn Phe Arg Ala Leu Thr Pro Ala Gln
1               5                   10                  15

Arg Leu Glu His Leu Ala Arg Ala Ala Ser Leu Ala Ala Asp Glu Thr
            20                  25                  30

Ala Leu Val Asp
        35

<210> SEQ ID NO 26
<211> LENGTH: 26
<212> TYPE: PRT
<213> ORGANISM: Delfitia sp.
<220> FEATURE:
<221> NAME/KEY: MUTAGEN
<222> LOCATION: (1)..(1)
<223> OTHER INFORMATION: Met, Val or Thr
<220> FEATURE:
<221> NAME/KEY: MUTAGEN
<222> LOCATION: (3)..(3)
<223> OTHER INFORMATION: Any amino acid
<220> FEATURE:
<221> NAME/KEY: MUTAGEN
<222> LOCATION: (19)..(19)
<223> OTHER INFORMATION: Any amino acid
<220> FEATURE:
<221> NAME/KEY: MUTAGEN
<222> LOCATION: (23)..(23)
<223> OTHER INFORMATION: Any amino acid
<220> FEATURE:
<221> NAME/KEY: MUTAGEN
<222> LOCATION: (24)..(24)
<223> OTHER INFORMATION: Asp or Ala
<220> FEATURE:
<221> NAME/KEY: MUTAGEN
<222> LOCATION: (25)..(25)
<223> OTHER INFORMATION: Any amino acid

<400> SEQUENCE: 26

Xaa Ala Xaa Ser Arg Leu Pro Asn Phe Arg Ala Asp Thr Pro Ala Gln
```

```
1               5                  10                 15
Arg Arg Xaa Phe Leu Ala Xaa Xaa Xaa Gly
            20                 25
```

```
<210> SEQ ID NO 27
<211> LENGTH: 36
<212> TYPE: PRT
<213> ORGANISM: Comamonas sp.
<220> FEATURE:
<221> NAME/KEY: MUTAGEN
<222> LOCATION: (1)..(1)
<223> OTHER INFORMATION: Met, Ala or Thr
<220> FEATURE:
<221> NAME/KEY: MUTAGEN
<222> LOCATION: (3)..(3)
<223> OTHER INFORMATION: Any amino acid
<220> FEATURE:
<221> NAME/KEY: MUTAGEN
<222> LOCATION: (23)..(23)
<223> OTHER INFORMATION: Thr or Leu
<220> FEATURE:
<221> NAME/KEY: MUTAGEN
<222> LOCATION: (25)..(25)
<223> OTHER INFORMATION: Any amino acid
<220> FEATURE:
<221> NAME/KEY: MUTAGEN
<222> LOCATION: (28)..(28)
<223> OTHER INFORMATION: Any amino acid
<220> FEATURE:
<221> NAME/KEY: MUTAGEN
<222> LOCATION: (31)..(32)
<223> OTHER INFORMATION: Any amino acid
<220> FEATURE:
<221> NAME/KEY: MUTAGEN
<222> LOCATION: (35)..(35)
<223> OTHER INFORMATION: Leu or Glu

<400> SEQUENCE: 27

Xaa Val Xaa Ser Arg Leu Pro Asn Phe Arg Ala Leu Thr Pro Ala Gln
1               5                  10                 15

Arg Trp Glu His Val Ala Xaa Ala Xaa Asn Leu Xaa Ala Arg Xaa Xaa
            20                 25                 30

Asn Glu Xaa Glu
        35
```